US011484341B2

(12) United States Patent
Muse et al.

(10) Patent No.: US 11,484,341 B2
(45) Date of Patent: Nov. 1, 2022

(54) SAFETY SHIELDS FOR ELONGATED INSTRUMENTS AND RELATED SYSTEMS AND METHODS

(71) Applicant: Piper Access, LLC, Salt Lake City, UT (US)

(72) Inventors: Jay Muse, Salt Lake City, UT (US); Ryan S. VanDyke, Layton, UT (US)

(73) Assignee: Piper Access, LLC, Salt Lake City, UT (US)

( * ) Notice: Subject to any disclaimer, the term of this patent is extended or adjusted under 35 U.S.C. 154(b) by 431 days.

(21) Appl. No.: 15/914,964

(22) Filed: Mar. 7, 2018

(65) Prior Publication Data

US 2018/0256209 A1    Sep. 13, 2018

Related U.S. Application Data

(60) Provisional application No. 62/525,663, filed on Jun. 27, 2017, provisional application No. 62/600,857, filed on Mar. 7, 2017.

(51) Int. Cl.
*A61B 17/34* (2006.01)
*A61B 17/16* (2006.01)
*A61B 17/00* (2006.01)

(52) U.S. Cl.
CPC ...... *A61B 17/3496* (2013.01); *A61B 17/1617* (2013.01); *A61B 17/3472* (2013.01);
(Continued)

(58) Field of Classification Search
CPC ............ A61B 17/3169; A61B 17/3494; A61B 2017/347; A61B 2090/0801;
(Continued)

(56) References Cited

U.S. PATENT DOCUMENTS

| 1,436,707 A | 11/1922 | Gaschke |
| 2,317,648 A | 4/1943 | Siqveland |

(Continued)

FOREIGN PATENT DOCUMENTS

| CA | 2207561 | 6/1997 |
| DE | 102007005963 A1 | 8/2008 |

(Continued)

OTHER PUBLICATIONS

PCT International Searching Authority, Notification of Transmittal of the International Search Report and the Written Opinion of the International Searching Authority for International Application No. PCT/US17/57270, dated Jan. 12, 2018, 12 pages.

(Continued)

*Primary Examiner* — Sarah A Simpson
(74) *Attorney, Agent, or Firm* — Med Venture Management, LLC; Daniel C. Higgs

(57) ABSTRACT

A system for intraosseous access can include an elongated instrument that is positioned within a cannula portion of a cannula assembly. The system can include a shield that is coupled with both the elongated instrument and the cannula assembly when in an unlocked state. The shield can permit proximal movement of the elongated instrument relative thereto when in the unlocked state. The shield can automatically transition to a locked state to attach to a distal end of the elongated instrument to restrict access to a distal tip of the elongated instrument.

18 Claims, 50 Drawing Sheets

(52) U.S. Cl.
CPC ...... *A61B 17/3476* (2013.01); *A61B 17/3494* (2013.01); *A61B 17/1633* (2013.01); *A61B 2017/00398* (2013.01); *A61B 2017/00477* (2013.01); *A61B 2017/00876* (2013.01); *A61B 2017/347* (2013.01)

(58) Field of Classification Search
CPC ...... A61B 2017/00398; A61B 17/3476; A61B 17/3472; A61B 17/3496; A61M 25/0612; A61M 25/0618
See application file for complete search history.

(56) References Cited

U.S. PATENT DOCUMENTS

| | | | |
|---|---|---|---|
| 4,275,721 A | 6/1981 | Olson |
| 4,321,914 A | 3/1982 | Begovac et al. |
| 4,356,828 A | 11/1982 | Jamshidi |
| 4,469,109 A | 9/1984 | Mehl |
| 4,593,681 A | 6/1986 | Soni |
| 4,736,742 A | 4/1988 | Alexson et al. |
| 4,755,170 A | 7/1988 | Golden |
| 4,755,173 A | 7/1988 | Konopka et al. |
| 4,758,225 A | 7/1988 | Cox et al. |
| 4,889,529 A | 12/1989 | Haindl |
| 4,929,241 A | 5/1990 | Kulli |
| 4,944,677 A | 7/1990 | Alexandre |
| 4,952,207 A | 8/1990 | Lemieux |
| 4,964,854 A | 10/1990 | Luther |
| 4,969,870 A | 11/1990 | Kramer et al. |
| 4,978,344 A | 12/1990 | Dombrowski et al. |
| 5,040,542 A | 8/1991 | Gray |
| 5,042,558 A | 8/1991 | Hussey et al. |
| 5,049,136 A | 9/1991 | Johnson |
| 5,053,017 A | 10/1991 | Chamuel |
| 5,073,169 A | 12/1991 | Raiken |
| 5,120,321 A | 6/1992 | Oksman et al. |
| 5,122,114 A | 6/1992 | Miller et al. |
| 5,135,504 A | 8/1992 | McLees |
| 5,137,520 A | 8/1992 | Maxson et al. |
| 5,183,468 A | 2/1993 | McLees |
| 5,207,697 A | 5/1993 | Carusillo et al. |
| 5,215,528 A | 6/1993 | Purdy et al. |
| 5,263,939 A | 11/1993 | Wortrich |
| 5,271,744 A | 12/1993 | Kramer et al. |
| 5,279,591 A | 1/1994 | Simon |
| 5,300,045 A | 4/1994 | Plassche, Jr. |
| 5,304,151 A | 4/1994 | Kuracina |
| 5,312,351 A | 5/1994 | Gerrone |
| 5,312,364 A | 5/1994 | Jacobs |
| 5,322,517 A | 6/1994 | Sircom et al. |
| 5,328,482 A | 7/1994 | Sircom et al. |
| 5,332,398 A | 7/1994 | Miller et al. |
| 5,334,158 A | 8/1994 | McLees |
| 5,344,408 A | 9/1994 | Partika |
| 5,348,544 A | 9/1994 | Sweeney et al. |
| 5,354,283 A | 10/1994 | Bark et al. |
| 5,357,974 A | 10/1994 | Baldridge |
| 5,364,367 A | 11/1994 | Banks et al. |
| 5,366,446 A | 11/1994 | Tal et al. |
| 5,368,046 A | 11/1994 | Scarfone et al. |
| 5,375,588 A | 12/1994 | Yoon |
| 5,405,348 A | 4/1995 | Anspach, Jr. et al. |
| 5,423,766 A | 6/1995 | Di Cesare |
| 5,431,655 A | 7/1995 | Melker et al. |
| 5,449,370 A | 9/1995 | Vaitekunas |
| 5,451,210 A | 9/1995 | Kramer et al. |
| 5,458,658 A | 10/1995 | Sircom |
| 5,472,427 A | 12/1995 | Rammler |
| 5,533,974 A | 7/1996 | Gaba |
| 5,554,154 A | 9/1996 | Rosenberg |
| 5,556,411 A | 9/1996 | Taoda et al. |
| 5,558,651 A | 9/1996 | Crawford et al. |
| 5,562,633 A | 10/1996 | Wozencroft |
| 5,571,133 A | 11/1996 | Yoon |
| 5,584,810 A | 12/1996 | Brimhall |
| 5,591,188 A | 1/1997 | Waisman |
| 5,601,559 A | 2/1997 | Melker et al. |
| 5,662,610 A | 9/1997 | Sircom |
| 5,667,509 A | 9/1997 | Westin |
| 5,683,378 A | 11/1997 | Christy |
| 5,697,907 A | 12/1997 | Gaba |
| 5,779,708 A | 7/1998 | Wu |
| 5,807,275 A | 9/1998 | Jamshidi |
| 5,882,337 A | 3/1999 | Bogert et al. |
| 6,001,080 A | 12/1999 | Kuracina et al. |
| 6,004,294 A | 12/1999 | Brimhall et al. |
| 6,071,284 A | 6/2000 | Fox |
| 6,077,244 A | 6/2000 | Botich et al. |
| 6,117,108 A | 9/2000 | Woehr et al. |
| 6,132,401 A | 10/2000 | Van Der Meyden et al. |
| 6,135,769 A | 10/2000 | Kwan |
| 6,183,442 B1 | 2/2001 | Athanasiou et al. |
| 6,228,088 B1 | 5/2001 | Miller et al. |
| 6,247,928 B1 | 6/2001 | Meller et al. |
| 6,273,715 B1 | 8/2001 | Meller et al. |
| 6,287,278 B1 | 9/2001 | Woehr et al. |
| 6,443,927 B1 | 9/2002 | Cook |
| 6,443,929 B1 | 9/2002 | Kuracina et al. |
| 6,585,704 B2 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,626,887 B1 | 9/2003 | Wu |
| 6,629,959 B2 | 10/2003 | Kuracina et al. |
| 6,652,486 B2 | 11/2003 | Bialecki et al. |
| 6,652,490 B2 | 11/2003 | Howell |
| 6,699,242 B2 | 3/2004 | Heggeness |
| 6,749,588 B1 | 6/2004 | Howell et al. |
| 6,761,726 B1 | 7/2004 | Findlay et al. |
| 6,796,962 B2 | 9/2004 | Ferguson et al. |
| 6,814,734 B2 | 11/2004 | Chappuis et al. |
| 6,860,871 B2 | 3/2005 | Kuracina et al. |
| 6,875,219 B2 | 4/2005 | Arramon et al. |
| 6,902,546 B2 | 6/2005 | Ferguson |
| 6,984,213 B2 | 1/2006 | Horner et al. |
| 7,004,927 B2 | 2/2006 | Ferguson et al. |
| 7,008,402 B2 | 3/2006 | Ferguson et al. |
| 7,070,580 B2 | 7/2006 | Nielsen |
| 7,179,244 B2 | 2/2007 | Smith et al. |
| 7,226,434 B2 | 6/2007 | Carlyon et al. |
| 7,264,613 B2 | 9/2007 | Woehr et al. |
| 7,341,573 B2 | 3/2008 | Ferguson et al. |
| 7,354,422 B2 | 4/2008 | Riesenberger et al. |
| 7,357,784 B2 | 4/2008 | Ferguson |
| 7,413,562 B2 | 8/2008 | Ferguson et al. |
| 7,458,954 B2 | 12/2008 | Ferguson et al. |
| 7,524,306 B2 | 4/2009 | Botich et al. |
| 7,588,559 B2 | 9/2009 | Aravena et al. |
| 7,601,139 B2 | 10/2009 | Woehr et al. |
| 7,611,485 B2 | 11/2009 | Ferguson |
| 7,618,395 B2 | 11/2009 | Ferguson |
| 7,670,328 B2 | 3/2010 | Miller |
| 7,699,808 B2 | 4/2010 | Marrs et al. |
| 7,699,850 B2 | 4/2010 | Miller |
| 7,749,225 B2 | 7/2010 | Chappuis et al. |
| 7,811,260 B2 | 10/2010 | Miller et al. |
| 7,815,642 B2 | 10/2010 | Miller |
| 7,850,620 B2 | 12/2010 | Miller et al. |
| 7,935,080 B2 | 5/2011 | Howell et al. |
| 7,967,792 B2 | 6/2011 | Bierman |
| 7,972,339 B2 | 7/2011 | Nassiri et al. |
| 8,038,664 B2 | 10/2011 | Miller et al. |
| 8,043,229 B2 | 10/2011 | Mulvihill et al. |
| 8,096,973 B2 | 1/2012 | Snow et al. |
| 8,142,365 B2 | 3/2012 | Miller |
| 8,206,355 B2 | 6/2012 | Thorne |
| 8,211,070 B2 | 7/2012 | Woehr et al. |
| 8,246,584 B2 | 8/2012 | Aravena et al. |
| 8,486,024 B2 | 7/2013 | Steube |
| 8,506,568 B2 | 8/2013 | Miller |
| 8,591,467 B2 | 11/2013 | Walker et al. |
| 8,628,497 B2 | 1/2014 | Finnestad et al. |
| 8,641,715 B2 | 2/2014 | Miller |

(56) References Cited

U.S. PATENT DOCUMENTS

| | | | |
|---|---|---|---|
| 8,656,929 | B2 | 2/2014 | Miller et al. |
| 8,668,698 | B2 | 3/2014 | Miller et al. |
| 8,684,978 | B2 | 4/2014 | Miller et al. |
| 8,715,287 | B2 | 5/2014 | Miller |
| 8,844,112 | B2 | 9/2014 | Snow et al. |
| 8,845,584 | B2 | 9/2014 | Ferguson et al. |
| 8,864,714 | B2 | 10/2014 | Harding et al. |
| 8,876,826 | B2 | 11/2014 | Miller |
| 8,926,563 | B2 | 1/2015 | Steube |
| 8,944,069 | B2 | 2/2015 | Miller et al. |
| 8,974,410 | B2 | 3/2015 | Miller et al. |
| 8,979,802 | B2 * | 3/2015 | Woehr .............. A61M 25/0618 604/164.08 |
| 8,992,535 | B2 | 3/2015 | Miller |
| 9,072,543 | B2 | 7/2015 | Miller et al. |
| 9,220,483 | B2 | 12/2015 | Frankhouser et al. |
| 9,295,487 | B2 | 3/2016 | Miller et al. |
| 9,314,228 | B2 | 4/2016 | Miller |
| 9,314,270 | B2 | 4/2016 | Miller |
| 9,393,031 | B2 | 7/2016 | Miller |
| 9,399,119 | B2 | 7/2016 | Kuracina et al. |
| 9,399,120 | B2 * | 7/2016 | Burkholz .......... A61M 25/0618 |
| 9,408,632 | B2 | 8/2016 | Erskine |
| 9,414,815 | B2 | 8/2016 | Miller et al. |
| 9,433,400 | B2 * | 9/2016 | Miller ................ A61B 17/3476 |
| 9,439,667 | B2 | 9/2016 | Miller |
| 9,439,702 | B2 | 9/2016 | Arthur et al. |
| 9,451,968 | B2 | 9/2016 | Miller et al. |
| 9,451,983 | B2 | 9/2016 | Windolf |
| 9,539,398 | B2 | 1/2017 | Ferguson et al. |
| 9,545,243 | B2 | 1/2017 | Miller et al. |
| 9,889,255 | B2 | 2/2018 | Sonderegger et al. |
| 10,980,522 | B2 | 4/2021 | Muse |
| 11,013,901 | B2 | 5/2021 | Muse et al. |
| 11,191,550 | B2 | 12/2021 | Muse |
| 2001/0011164 | A1 | 8/2001 | Bierman |
| 2002/0123724 | A1 | 9/2002 | Douglas et al. |
| 2003/0225344 | A1 | 12/2003 | Miller |
| 2003/0225411 | A1 | 12/2003 | Miller |
| 2004/0059317 | A1 | 3/2004 | Hermann |
| 2004/0220497 | A1 | 11/2004 | Findlay et al. |
| 2005/0027263 | A1 * | 2/2005 | Woehr .............. A61M 25/0618 604/263 |
| 2005/0033235 | A1 | 2/2005 | Flint |
| 2005/0101933 | A1 | 5/2005 | Marrs et al. |
| 2005/0107743 | A1 | 5/2005 | Fangrow, Jr. |
| 2005/0165404 | A1 | 7/2005 | Miller |
| 2005/0245878 | A1 | 11/2005 | Mernoe et al. |
| 2006/0015066 | A1 | 1/2006 | Turieo et al. |
| 2006/0025723 | A1 | 2/2006 | Ballarini |
| 2006/0106402 | A1 | 5/2006 | McLucas |
| 2007/0049945 | A1 | 3/2007 | Miller |
| 2007/0270775 | A1 | 11/2007 | Miller et al. |
| 2008/0140014 | A1 | 6/2008 | Miller et al. |
| 2008/0215056 | A1 * | 9/2008 | Miller ................ A61B 17/1628 606/80 |
| 2008/0221580 | A1 | 9/2008 | Miller et al. |
| 2009/0054808 | A1 | 2/2009 | Miller |
| 2009/0093830 | A1 | 4/2009 | Miller |
| 2009/0118639 | A1 | 5/2009 | Moos et al. |
| 2009/0204024 | A1 | 8/2009 | Miller |
| 2009/0306697 | A1 | 12/2009 | Fischvogt |
| 2010/0152616 | A1 | 6/2010 | Beyhan et al. |
| 2010/0298784 | A1 | 11/2010 | Miller |
| 2011/0028976 | A1 | 2/2011 | Miller |
| 2011/0082387 | A1 | 4/2011 | Miller et al. |
| 2012/0046620 | A1 * | 2/2012 | Woehr .................. A61M 5/158 604/263 |
| 2013/0030370 | A1 | 1/2013 | Walker et al. |
| 2013/0096561 | A1 | 4/2013 | Miller et al. |
| 2014/0025009 | A1 * | 1/2014 | Erskine ............. A61M 25/0606 604/164.08 |
| 2014/0100528 | A1 | 4/2014 | Finnestad et al. |
| 2014/0142577 | A1 | 5/2014 | Miller |
| 2014/0276471 | A1 | 9/2014 | Emery et al. |
| 2014/0277028 | A1 | 9/2014 | Voic |
| 2014/0343454 | A1 | 11/2014 | Miller et al. |
| 2015/0127006 | A1 | 5/2015 | Miller |
| 2015/0230823 | A1 | 8/2015 | Morgan et al. |
| 2015/0231364 | A1 * | 8/2015 | Blanchard ....... A61M 25/09041 604/164.08 |
| 2015/0342756 | A1 | 12/2015 | Bays et al. |
| 2015/0351797 | A1 | 12/2015 | Miller et al. |
| 2015/0366569 | A1 | 12/2015 | Miller |
| 2016/0022282 | A1 | 1/2016 | Miller et al. |
| 2016/0058432 | A1 | 3/2016 | Miller |
| 2016/0066954 | A1 | 3/2016 | Miller et al. |
| 2016/0183974 | A1 | 6/2016 | Miller |
| 2016/0184509 | A1 | 6/2016 | Miller et al. |
| 2016/0206346 | A1 | 7/2016 | Miller |
| 2017/0007271 | A1 | 1/2017 | Miller et al. |
| 2017/0311981 | A1 | 11/2017 | Real et al. |
| 2018/0125465 | A1 | 5/2018 | Muse et al. |
| 2018/0256209 | A1 | 9/2018 | Muse et al. |
| 2018/0256870 | A1 | 9/2018 | Muse et al. |
| 2019/0282244 | A1 | 9/2019 | Muse |
| 2021/0196249 | A1 | 7/2021 | Muse |
| 2021/0236788 | A1 | 8/2021 | Muse et al. |

FOREIGN PATENT DOCUMENTS

| | | |
|---|---|---|
| EP | 0548612 A1 | 6/1993 |
| EP | 2849656 B1 | 5/2013 |
| EP | 2967508 B1 | 1/2016 |
| EP | 3568083 B1 | 4/2021 |
| FR | 2481930 | 11/1981 |
| FR | 2522973 A2 | 9/1983 |
| FR | 2885512 A1 | 11/2006 |
| JP | 2000140125 A | 12/1998 |
| NL | 9401085 A | 6/1994 |
| WO | 200213893 A1 | 2/2002 |
| WO | 2008065646 A1 | 6/2008 |
| WO | 2013173360 A1 | 11/2013 |
| WO | 2014144239 A1 | 9/2014 |
| WO | 2018075694 A1 | 4/2018 |
| WO | 20180165334 A1 | 9/2018 |
| WO | 20180165339 A1 | 9/2018 |
| WO | 20190164990 A1 | 8/2019 |

OTHER PUBLICATIONS

Prometheus Medical Ltd., Prometheus PIN, Undated, Downloaded from https://www.prometheusmedical.co.uk/equipment/prometheus-equipment-intraosseous-access/prometheus-pin on Aug. 10, 2017, 2 pages.

United States Patent and Trademark Office, Office Action in U.S. Appl. No. 15/787,671, dated Feb. 27, 2020, 12 pages.

United States Patent and Trademark Office, Notice of Allowance in U.S. Appl. No. 15/787,671, dated Sep. 16, 2020, 18 pages.

United States Patent and Trademark Office, Notice of Allowance in U.S. Appl. No. 15/787,671, dated Dec. 31, 2020, 53 pages.

United States Patent and Trademark Office, Office Action in U.S. Appl. No. 15/915,606, dated Sep. 23, 2020, 10 pages.

* cited by examiner

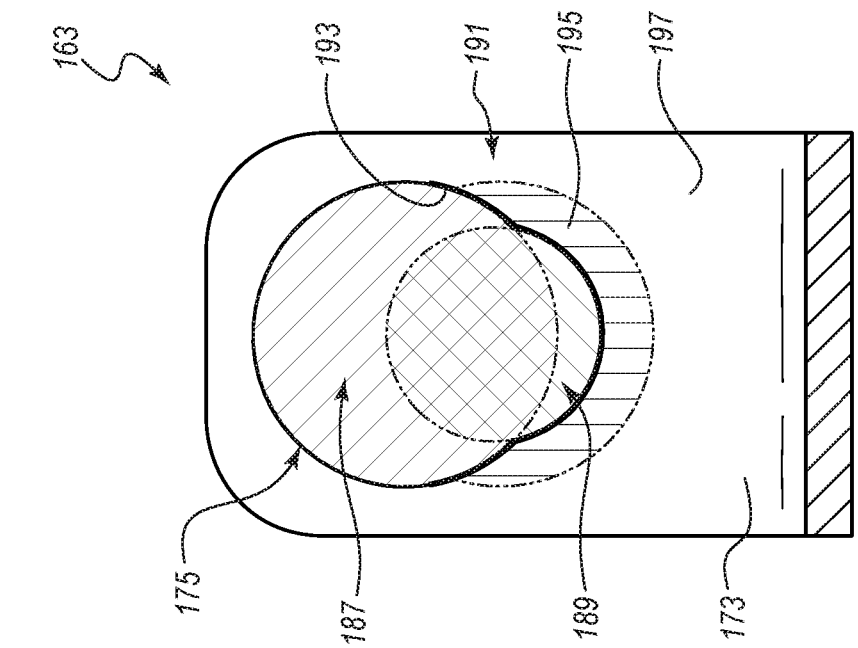
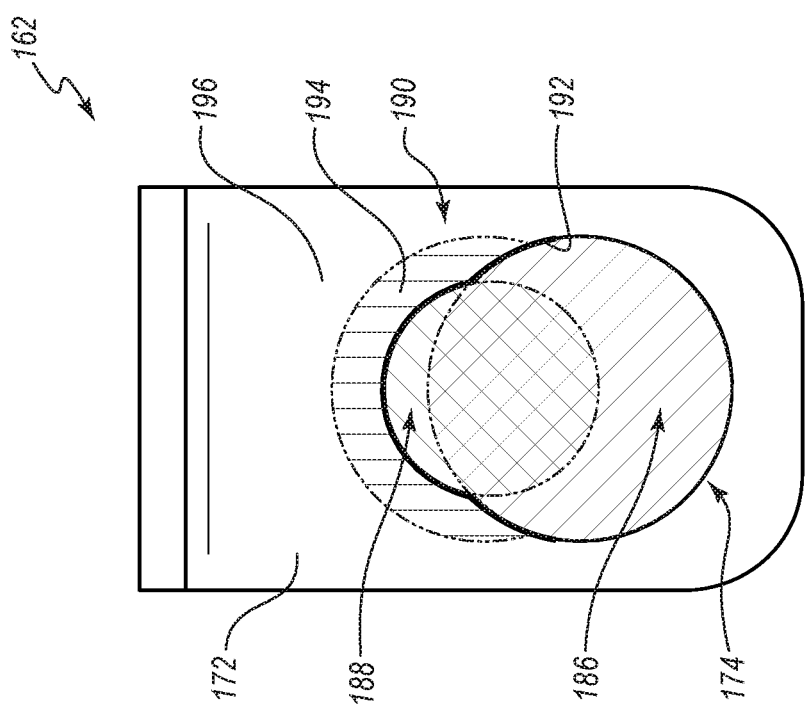

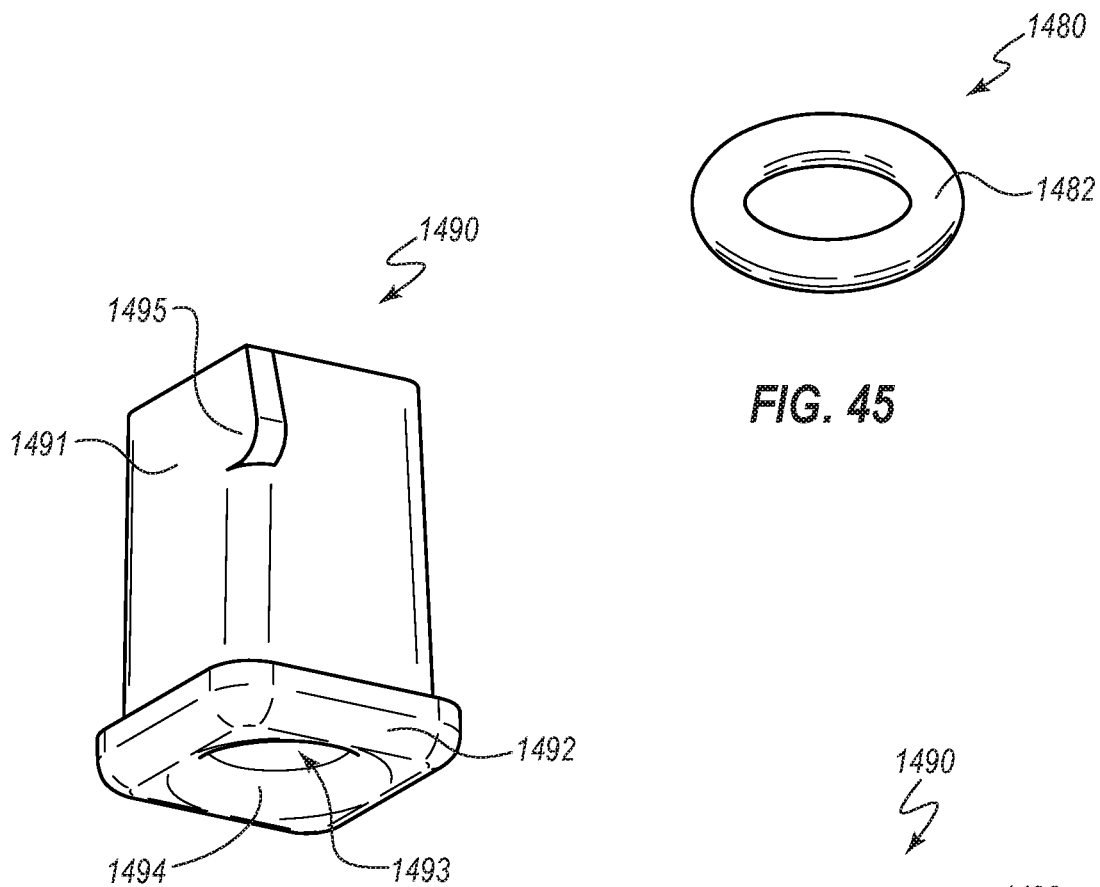
FIG. 45
FIG. 46A
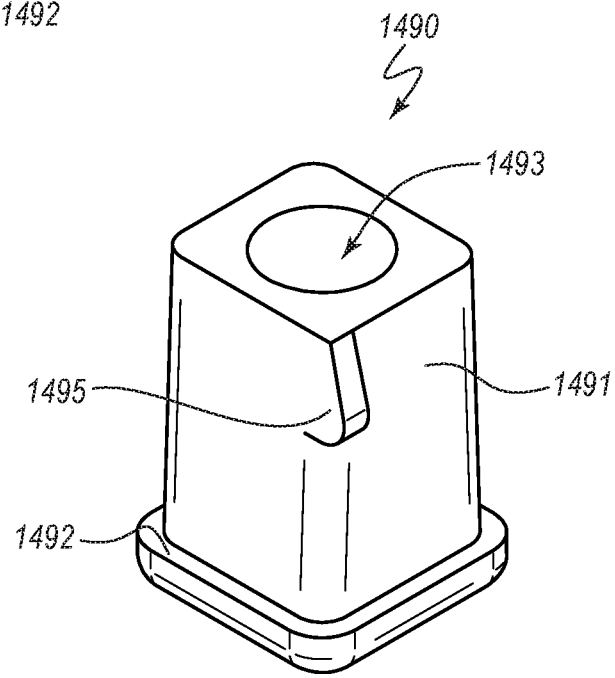
FIG. 46B

SAFETY SHIELDS FOR ELONGATED INSTRUMENTS AND RELATED SYSTEMS AND METHODS

CROSS-REFERENCE TO RELATED APPLICATIONS

This application claims the benefit under 35 U.S.C. § 119(e) of U.S. Provisional Patent Application No. 62/600,857, titled NEEDLE TIP CAPTURE MECHANISM, filed on Mar. 7, 2017, and U.S. Provisional Patent Application No. 62/525,663, titled SAFETY SHIELDS FOR ELONGATED INSTRUMENTS AND RELATED SYSTEMS AND METHODS, filed on Jun. 27, 2017, the entire contents of each of which are hereby incorporated by reference herein.

TECHNICAL FIELD

Certain embodiments described herein relate generally to safety shields for elongated medical instruments, and further embodiments relate more particularly to safety shields for protecting the distal tips of elongated instruments, such as those used in intraosseous access procedures.

BACKGROUND

Many devices, systems, and methods have been developed to cover distal tips of elongated medical instruments, such as needles, after those instruments have been used with a patient. Such devices, systems, and methods can protect a practitioner from inadvertent sticks, which might otherwise result in the contraction of bloodborne illnesses. Known devices, systems, and methods, however, suffer from one or more drawbacks that can be resolved, remedied, ameliorated, or avoided by certain embodiments described herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 8 is a top plan view of an arm portion of the shield;

FIG. 9 is a cross-sectional view of another arm portion of the shield taken along the view line 9-9 in FIG. 7;

FIG. 45 is a perspective view of a retainer portion of the shield of FIG. 43;

FIG. 46A is a perspective view of a guide portion of the shield of FIG. 43;

FIG. 46B is another perspective view of the guide portion of the shield of FIG. 43.

DETAILED DESCRIPTION

Figure 1:
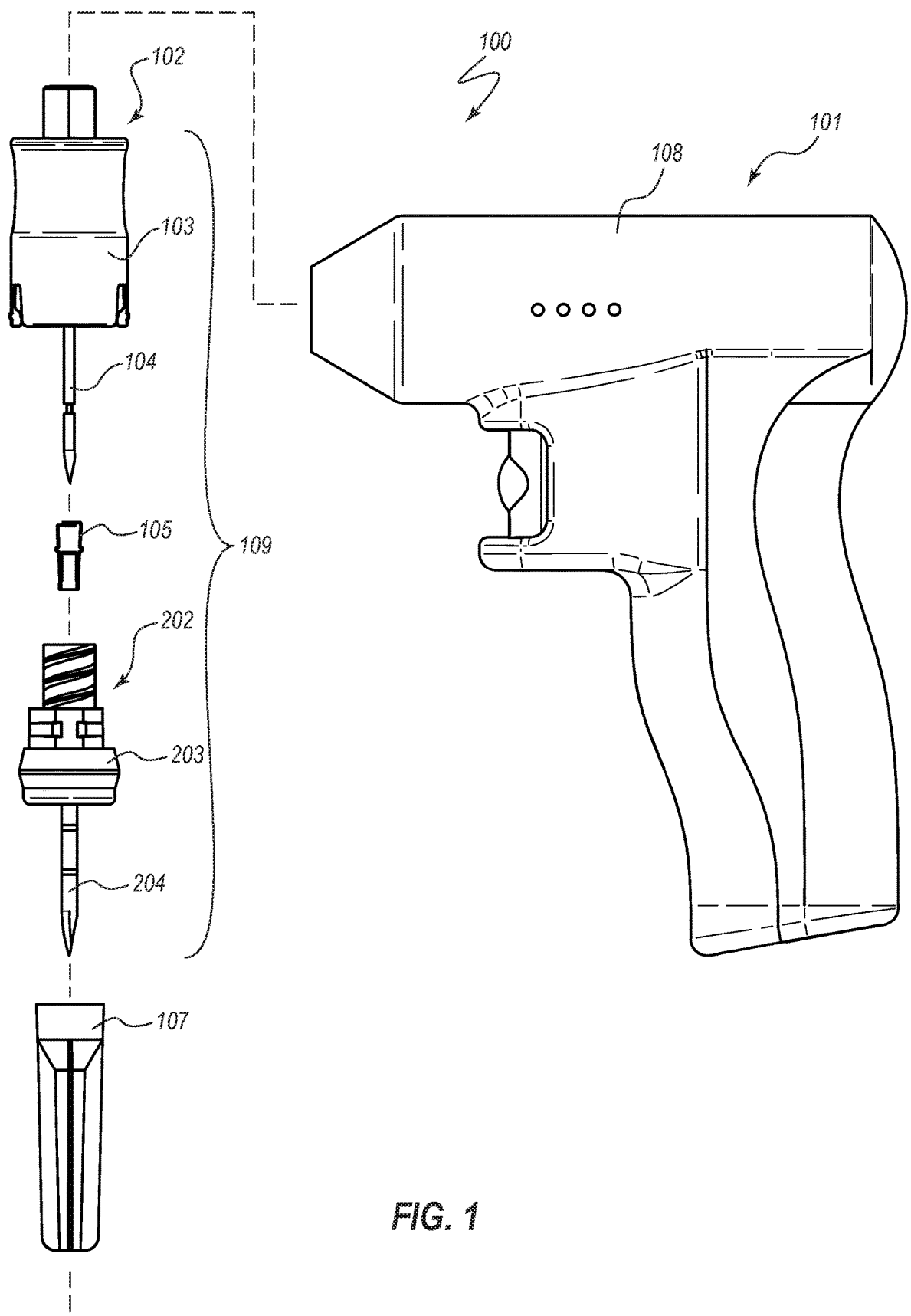
FIG. 1 is an exploded elevation view of an embodiment of an intraosseous access system that includes an automated driver.

The present disclosure relates generally to safety shields for elongated medical instruments. Some embodiments relate more particularly to safety shields for protecting the distal tips of elongated instruments used in intraosseous access procedures. As used herein, the term "elongated medical instrument" is a broad term used in its ordinary sense that includes, for example, such devices as needles, cannulas, trocars, obturators, stylets, etc. Although certain embodiments are particularly well-suited for intraosseous access applications for at least the reasons discussed herein and/or for reasons that are otherwise apparent from the present disclosure, and although the embodiments depicted in the drawings are discussed in the context of such applications, the present disclosure is not so limited. For example, embodiments may be used in other contexts, such as for shielding needles that may be removed from hubs (e.g., catheter hubs) after providing vascular or other access to a patient. For example, while some embodiments are disclosed herein in the context of achieving intraosseous access, in which the vasculature of a patient is accessed via a bone, or via which a biopsy sample is remove, certain of such embodiments can be used in other systems that are introduced into a patient.

For purposes of illustration, much of the disclosure herein pertains to creating a conduit or communication passageway to an interior of a bone structure by drilling through or otherwise penetrating hard, compact bone tissue to gain access to soft bone marrow. Once access to the soft bone marrow is achieved, any variety of suitable procedures can be performed, such as, for example, infusion, aspiration, or extraction of bone marrow or other components of the bone. Numerous situations can benefit from providing access to bone marrow in manners such as disclosed herein, such as, for example, when other methods of accessing a vein with an IV needle are difficult or in emergent situations, such as heart attack, burns, drug overdoses, etc., when rapid access to the marrow may be desired.

Certain embodiments are particularly useful with bone penetrating devices, systems, and methods. In particular, certain embodiments disclosed herein can be used with systems for drilling through or otherwise being inserted into or penetrating hard, compact bone tissue to gain access to soft bone marrow.

Certain prior systems and methods for providing access to a bone rely on a penetrator assembly that includes an outer penetrator and an inner trocar operable by a drill to penetrate the compact bone to gain access to the bone marrow. Once access to the bone has been achieved, the trocar is removed from the outer penetrator and a distal tip of the trocar is left in an exposed state. During insertion, however, the trocar may come into contact with and retain thereon, e.g., blood-borne pathogens or other bodily fluid- or bodily matter-borne pathogens. The exposed distal tip of the trocar is thus a safety hazard, as it could cause inadvertent sticks yielding undesired infections.

Certain embodiments disclosed herein can be advantageous over such prior systems and methods for at least their resolution of the foregoing problem. For example, certain embodiments of access systems are disclosed that include a multi-member insertion assembly that includes a shield. For example, the access systems may include a needle or cannula and one of an obturator or a trocar that is inserted into a lumen of the needle or cannula. The needle or cannula and said one of the obturator or the trocar may be rotated (e.g., in unison at high rotational speeds) to penetrate through skin and underlying bone. Once insertion is achieved, the needle or cannula may be left in place in the bone to provide a fluid channel into the bone, and the obturator or trocar can be removed from the needle or cannula. The shield can automatically lock to a distal end of the obturator or trocar as it is removed from the needle or cannula. The locked shield can inhibit or prevent inadvertent contact with the distal tip of the obturator or trocar. These and/or other advantages of various embodiments disclosed herein will be apparent from the discussion that follows.

FIG. 1 is an exploded elevation view of an embodiment of an intraosseous access system 100. In various embodiments, the system includes a driver 101 and an access assembly 109. The driver 101 can be used to rotate the access assembly 109 into a bone of a patient. In various embodiments, the driver 101 can be automated or manual. In the illustrated embodiment, the driver 101 is an automated driver 108. For example, the automated driver 108 can be a drill that achieves high rotational speeds.

The intraosseous access system 100 can further include an obturator assembly 102, a shield 105, and a needle assembly 202, which may be referred to, collectively, as the access assembly 109. The access assembly 109 may also be referred to as an access system. The obturator assembly 102 is referred to as such herein for convenience. In the illustrated embodiment, the obturator assembly 102 includes an obturator 104. However, in various other embodiments, the obturator 104 may be replaced with a different elongated medical instrument, such as, for example, a trocar, a needle, or a stylet, and/or may be referred to by a different name, such as one or more of the foregoing examples. Accordingly, the obturator assembly 102 may be referred to more generally as an elongated medical instrument assembly. In like manner, the obturator 104 may be referred to more generally as an elongated medical instrument.

In the illustrated embodiment, the obturator assembly 102 includes a coupling hub 103 that is attached to the obturator 104 in any suitable manner. The coupling hub 103 can be configured to interface with the driver 101, as further discussed below. The coupling hub 103 may alternatively be referred to as an obturator hub 103 or, more generally, as an elongated instrument hub 103.

In the illustrated embodiment, the shield 105 is configured to couple with the obturator 104. The coupling can permit relative movement between the obturator 104 and the shield 105, such as sliding, translating, or other axial movement, when the shield 105 is in a first operational mode, and can prevent the same variety of movement when the shield 105 is transitioned to a second operational mode. For example, as further discussed below, the shield 105 may couple with the obturator 104 in a manner that permits longitudinal translation when the obturator 104 maintains the shield 105 in an unlocked state, and when the obturator 104 is moved to a position where the obturator 104 no longer maintains the shield in the unlocked state, the shield 105 may automatically transition to a locked state in which little or no translational movement is permitted between the shield 105 and the obturator 104. Stated otherwise, the shield 105 may be longitudinally locked to a fixed or substantially fixed longitudinal orientation relative to the obturator 104 at which the shield 105 inhibits or prevents inadvertent contact with a distal tip of the obturator, as further discussed below.

With continued reference to FIG. 1, the needle assembly 202 is referred to as such herein for convenience. In the illustrated embodiment, the needle assembly 202 includes a needle 204. However, in various other embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In the illustrated embodiment, the needle assembly 202 includes a needle hub 203 that is attached to the needle 204 in any suitable manner. The needle hub 203 can be configured to couple with the coupling hub 103 and may thereby be coupled with the driver 101, as further discussed below. The needle hub 203 may alternatively be referred to as a cannula hub 203.

In the illustrated embodiment, the shield 105 is configured to couple with the needle hub 203. The coupling can prevent relative axial movement between the needle hub 203 and the shield 105, such as sliding, translating, or the like, when the shield 105 is in the first operational mode, and can permit the shield 105 to decouple from the needle hub 203 when the shield 105 is transitioned to the second operational mode. For example, as further discussed below, the shield 105 may couple with the needle hub 203 so as to be maintained at a substantially fixed longitudinal position relative thereto when the obturator 104 maintains the shield 105 in the unlocked state, and when the obturator 104 is moved to a position where the obturator 104 no longer maintains the shield in the unlocked state, the shield 105 may automatically transition to a locked state relative to the obturator 104 in which the shield 105 also decouples from the needle hub 203.

As further discussed below, the shield 105 can be coupled with the obturator 104, the obturator 104 can be inserted into the needle 204, and the obturator hub 103 can be coupled to the needle hub 203 to assemble the access assembly 109. In the illustrated embodiment, a cap 107 may be provided to cover at least a distal portion of the needle 204 and the obturator 103 prior to use of the access assembly 109. For example, as further discussed below, in the illustrated embodiment, a proximal end of the cap 107 can be coupled to the obturator hub 103.

Figure 2:
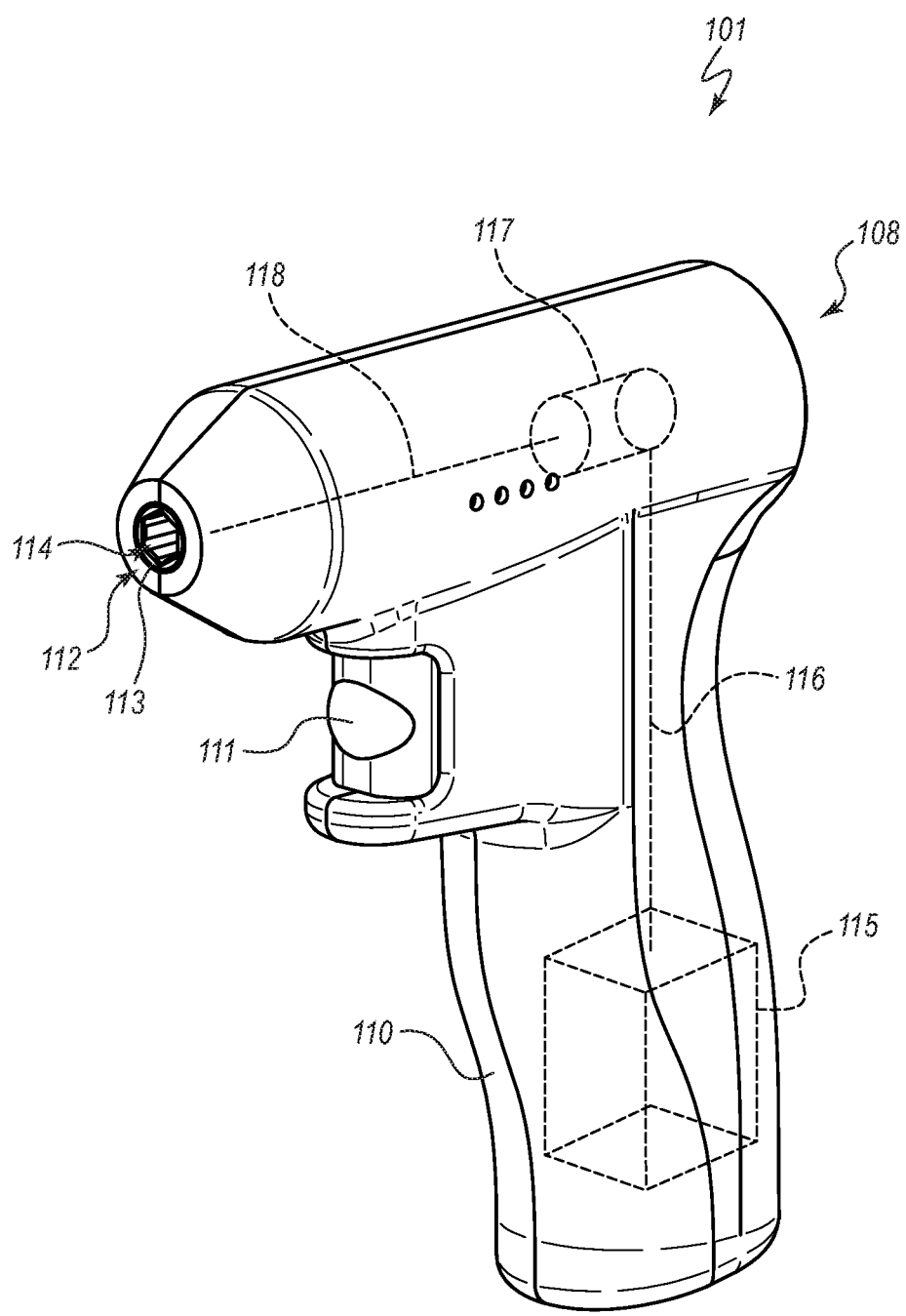
FIG. 2 is a perspective view of the automated driver of the intraosseous access system of FIG. 1.

With reference to FIG. 2, the automated driver 108 may take any suitable form. The driver 108 may include a handle 110 that may be gripped by a single hand of a user. The driver 108 may further include an actuator 111 of any suitable variety via which a user may selectively actuate the driver 108 to effect rotation of a coupling interface 112. For example, the actuator 111 may comprise a button, as shown, or a switch or other mechanical or electrical element for actuating the driver 108. In the illustrated embodiment, the coupling interface 112 is formed as a socket 113 that defines a cavity 114. The coupling interface 112 can be configured to couple with the coupling hub 103 (see FIG. 1).

The automated driver 108 can include an energy source 115 of any suitable variety that is configured to energize the rotational movement of the coupling interface 112. For example, in some embodiments, the energy source 115 may comprise one or more batteries that provide electrical power for the automated driver 108. In other embodiments, the energy source 115 can comprise a spring (e.g., a coiled spring) or other biasing member that may store potential energy that may be released upon actuation of the actuator 111.

The energy source 115 may be coupled with the coupling interface 112 in any suitable manner. For example, in the illustrated embodiment, the automated driver 108 includes an electrical, mechanical, or electromechanical coupling 116 to a gear assembly 117. In some embodiments, the coupling 116 may include an electrical motor that generates mechanical movement from electrical energy provided by an electrical energy source 116. In other embodiments, the coupling 116 may include a mechanical linkage that mechanically transfers rotational energy from a mechanical (e.g., spring-based) energy source 115 to the gear assembly 117. The automated driver 108 can include a mechanical coupling 118 of any suitable variety to couple the gear assembly 117 with the coupling interface 112. In other embodiments, the gear assembly 117 may be omitted.

In various embodiments, the automated driver 108 can rotate the coupling interface 112, and thereby, can rotate the access assembly 109 at rotational speeds significantly greater than can be achieved by manual rotation of the access assembly 109. For example, in various embodiments, the automated driver 108 can rotate the access assembly 109 at speeds no less than 300, 400, 500, 750, 1,000, 1,250, 1,500, or 1,750 rotations per minute.

Figure 3:
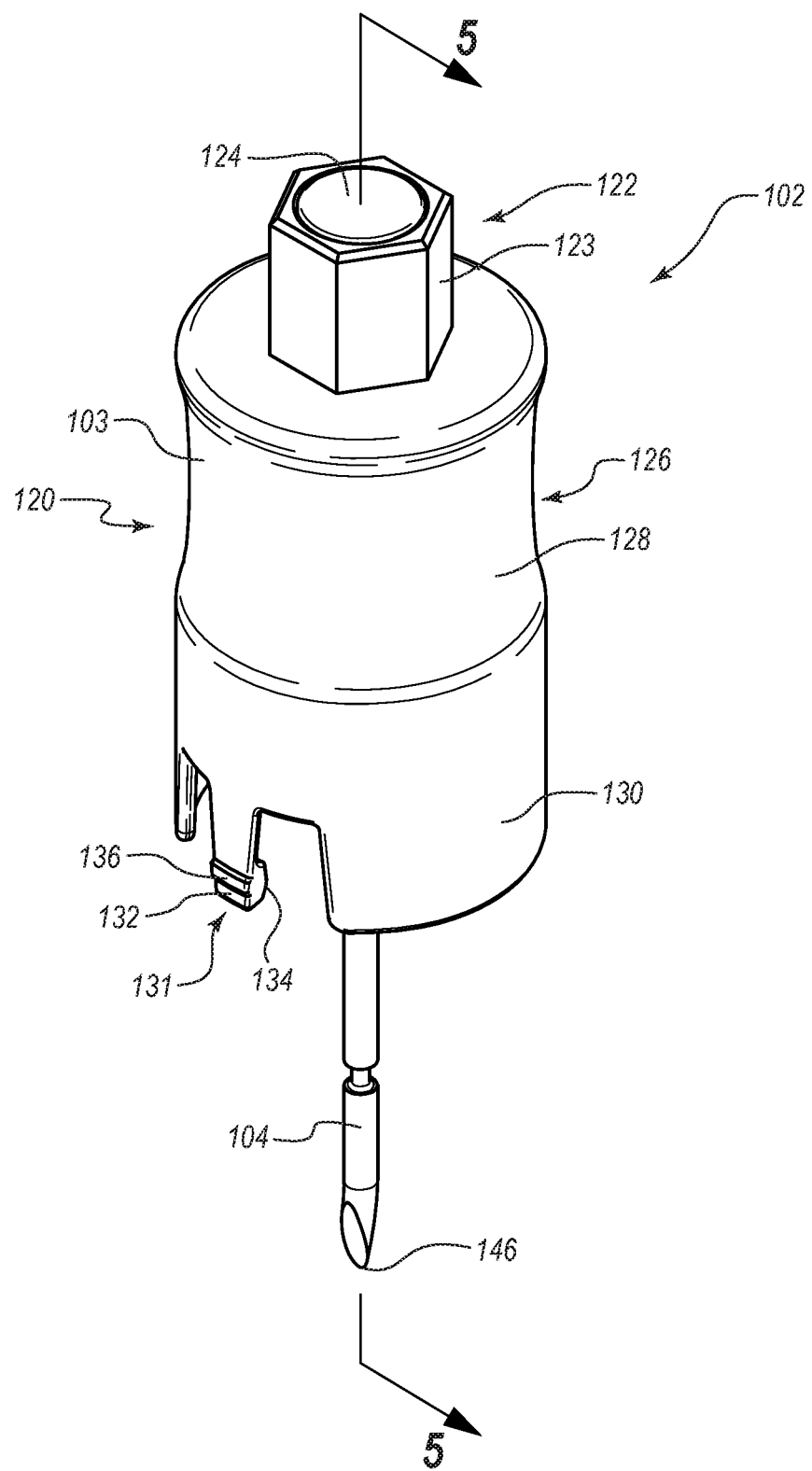
FIG. 3 is a perspective view of an embodiment of an obturator assembly portion of the intraosseous access system of FIG. 1.
Figure 4:
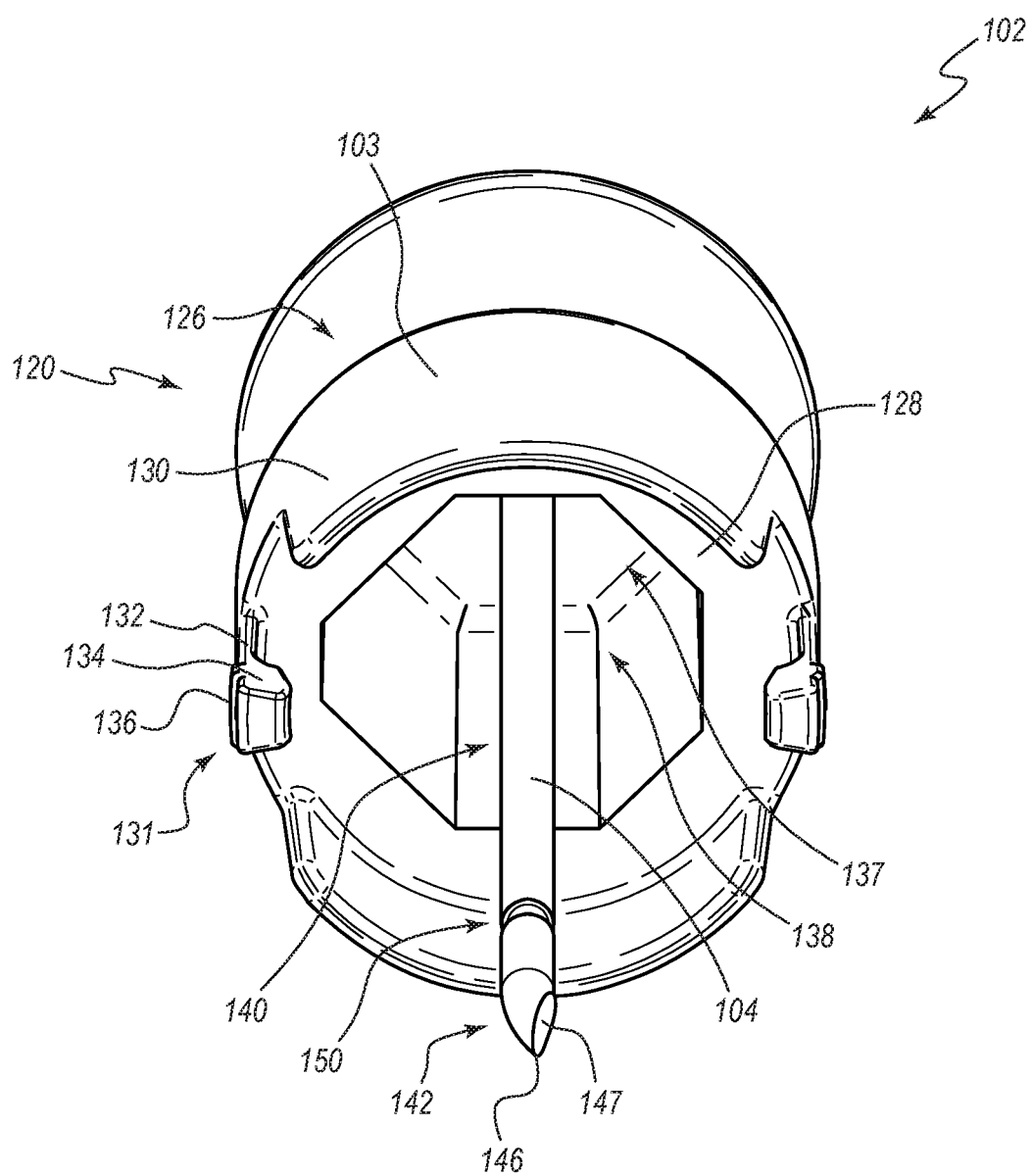
FIG. 4 is a further perspective view of the obturator assembly of FIG. 3.
Figure 5:
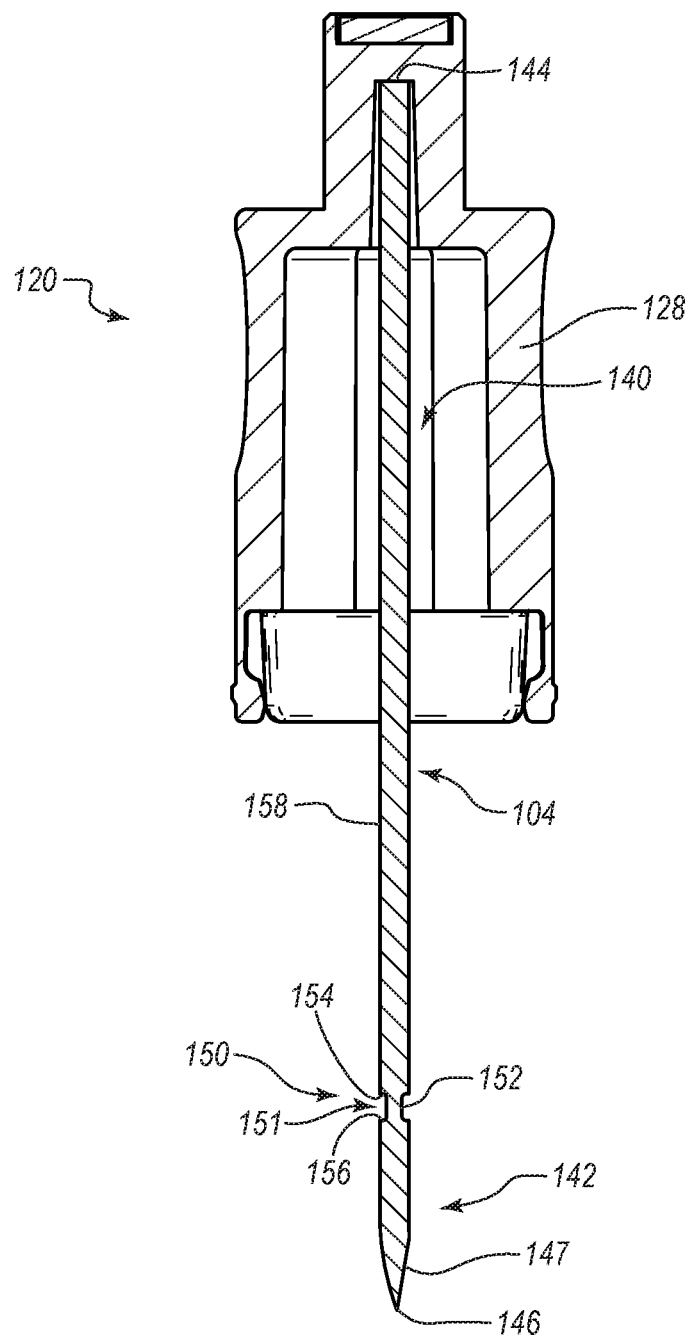
FIG. 5 is a cross-sectional view of the obturator assembly taken along the view line 5-5 in FIG. 3.

With reference to FIGS. 3-5, the obturator assembly 102, which includes the coupling hub 103 and the obturator 104, is shown in greater detail. In the illustrated embodiment, the obturator hub 103 includes a body or housing 120. A proximal end of the housing 120 can be coupled with (e.g., may be attached to or may itself define) a coupling interface 122 for coupling with the coupling interface 112 of the driver 101. In the illustrated embodiment, the coupling interface 122 is formed as a shaft 123 that is configured to be received within the cavity 114 of the socket 113 of the automated driver 108. In particular, the shaft 123 can interface with the socket 113 so as to be rotated thereby. In the illustrated embodiment, the shaft 123 defines a hexagonal cross-section that complements a hexagonal cross-section of the socket 113. Any other suitable arrangement is contemplated. In further embodiments, the socket 113, and the shaft 123 may be reversed, in that the driver 101 may include a shaft and the coupling hub 103 may define a socket for receiving the shaft of the driver 101.

The coupling interface 122 of the coupling hub 103 may further include a magnetic member 124, which may facilitate coupling with and/or may strengthen a coupling between the coupling interfaces 122, 112 of the coupling hub 103 and the driver 101, respectively. In various embodiments, the magnetic member 124 may include, for example, one or more of a ferromagnetic material and a ferromagnet. In some embodiments, the socket 113 may include a similar magnetic member that magnetically couples with the magnetic member 124. In other embodiments, the socket 113 itself may be formed as the magnetic member. For example, in some embodiments, the magnetic member 124 may comprise a magnet and the socket 113 may include a complementary magnetic member (not shown) at the base of the cavity 114. In other embodiments, the magnetic member 124 may comprise a magnet and the socket 113 may be formed of a magnetic material which the magnetic member 124 is attracted. In other embodiments, the magnetic member 124 may be omitted.

The body or housing 120 may further define a grip 126 that may facilitate manipulation of the coupling hub 103. For example, in the illustrated embodiment, the grip 126 is formed as an indented region of a sidewall 128 that spans a full perimeter of the housing 120.

The illustrated coupling hub 103 includes a skirt 130 that extends distally from a central portion of the housing 120. In the illustrated embodiment, the skirt 130 is defined by a distal portion of the sidewall 128. The skirt 130 can include one or more mechanical coupling members 131 that are configured to selectively couple the coupling hub 103 to the needle hub 203. In the illustrated embodiment, the skirt 130 includes two such mechanical coupling members 131 at opposite sides thereof. In particular, the illustrated embodiment includes two resilient arms or projections 132 that are capable of resiliently deforming in a lateral or radial direction. Each arm can include a snap interface, inward protrusion, or catch 134 at an internal side thereof that can interface with the needle hub 203 to achieve the coupling configuration.

In the illustrated embodiment, the obturator hub 103 further includes a pair of outward protrusions 136 (see also FIG. 4) that can assist in coupling the cap 107 to the obturator hub 103. For example, in some embodiments, the cap 107 can define an inner diameter only slightly larger than an outer diameter of the skirt 130. The outward protrusions 136 can slightly deform a proximal end of the cap 107 from a substantially cylindrical shape to a more oblong shape, which may enhance a grip of the cap 107 against the skirt 130. Any other suitable connection arrangement for the cap 107 is contemplated.

With reference to FIG. 4, the sidewall 128 can further define a coupling interface 137 configured to couple the coupling hub 103 to the needle hub 203 in a manner that causes the coupling hub 103 to rotate in unison with the needle hub 203. In the illustrated embodiment, the coupling interface 137 is formed as a socket 138 into which a shaft portion of the needle hub 203 can be received. The socket 138 can define a keyed shape that permits the coupling hub 103 to be coupled to the needle hub 203 in only one unique rotational or angular orientation. In particular, in the illustrated embodiment, the socket 138 defines an elongated right octagonal prism of which five contiguous sides are substantially identically sized, two enlarged sides that extend from the ends of the five contiguous sides are lengthened relative to the five contiguous sides, and an eighth shorted side that extends between the two enlarged sides is shorter than the five contiguous sides. Any other suitable keying configuration is contemplated. As further discussed below, a keyed interface such as just described can ensure that the obturator 104 and the needle 204 are coupled to each other in a manner that may be desired, in some embodiments, such as to ensure that distal faces of both components are substantially parallel to each other and/or to ensure that a distal face of the obturator 104 is fully recessed relative to a distal face of the needle 204.

With reference to FIGS. 4 and 5, in some embodiments, the obturator 104 extends between a proximal end 140 and a distal end 142. The proximal end 140 of the obturator 104 has a proximal tip 144 at an extremity thereof, and the distal end 142 of the obturator 104 has a distal tip 146 at an extremity thereof. In the illustrated embodiment, the housing 120 of the coupling hub 103 substantially encompasses the proximal end 140 of the obturator 104.

The distal end 142 of the obturator 104 includes a distal face 147. The distal face 147 may be substantially planar and may be at an angle relative to a longitudinal axis of the obturator 104. In some embodiments, the distal face 147 may be formed as a back bevel. In some embodiments, the distal end 142 of the obturator 104 may be configured to be recessed relative to a distal face of the needle 204

In the illustrated embodiment, the obturator 104 may further include a recess 150. The recess 150 may be at a position that is between the proximal end 140 and the distal end 142 of the obturator. Stated otherwise, the recess 150 may be positioned proximally relative to the distal tip 146 of the obturator 104. The recess 150 may be of any suitable variety, such as a groove, track, or any other suitable region of indentation or of reduced diameter or reduced thickness, as compared with, for example, a portion of the obturator 104 that is proximal to the recess 150. The recess 150 may or may not extend fully about a longitudinal axis of the obturator 104.

With reference to FIG. 5, in the illustrated embodiment, the recess 150 is defined as a groove 151 that extends fully about the longitudinal axis of the obturator. The groove 151 includes a base surface 152, or inner surface or base wall, that is recessed relative to portions of the obturator 104 that are positioned proximally and distally adjacent to the recess 150. The groove 151 further includes a proximal face 154 and a distal face 156, which may also be referred to as sidewalls. In the illustrated embodiment, each of the proximal and distal faces 154, 156 is substantially planar and extends substantially orthogonally relative to a longitudinal axis of the obturator 104. The faces 154, 156 may each be shaped substantially as an annulus. As further discussed below, the faces 154, 156 can delimit movement of the shield 105 after it has been transitioned to the locked state.

Figure 6:
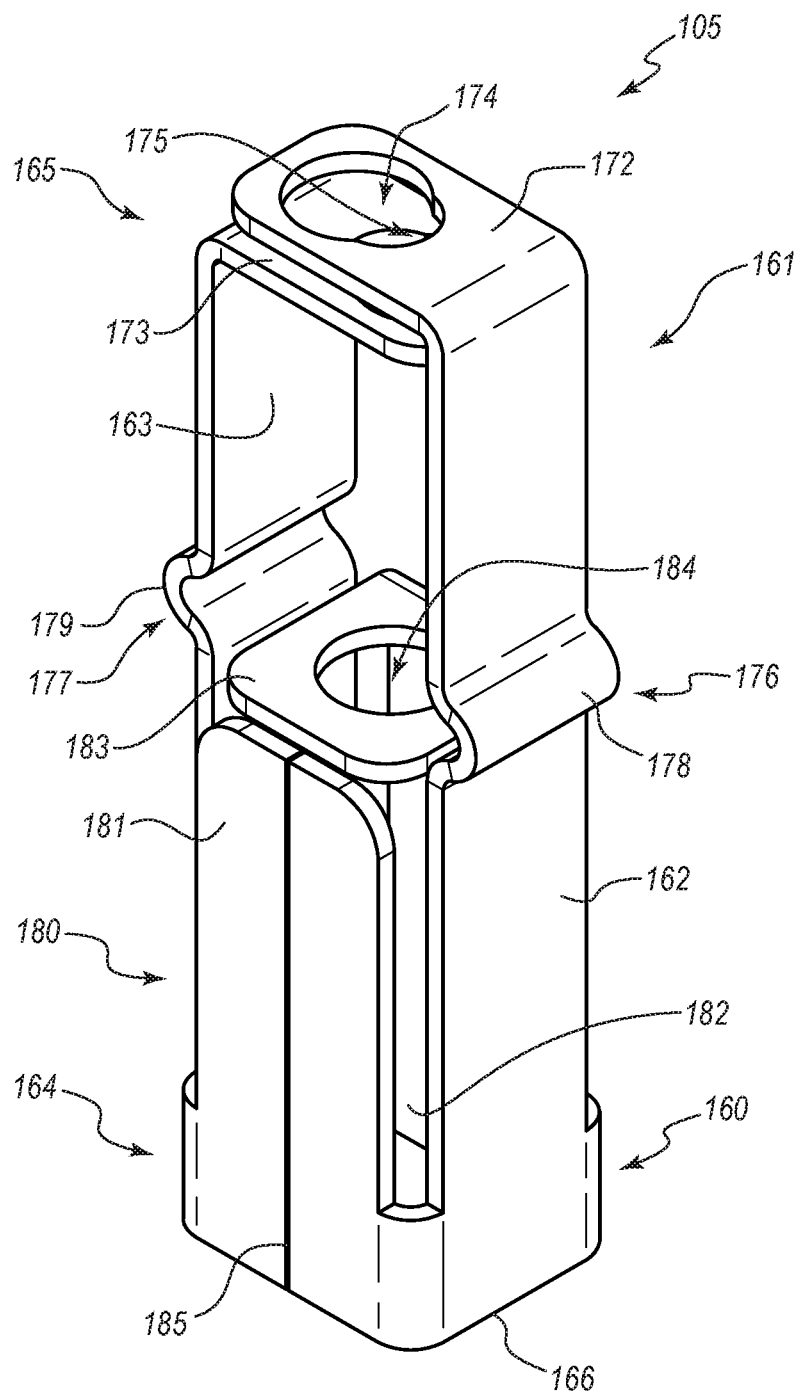
FIG. 6 is a perspective view of an embodiment of a shield portion of the intraosseous access system of FIG. 1.
Figure 7:
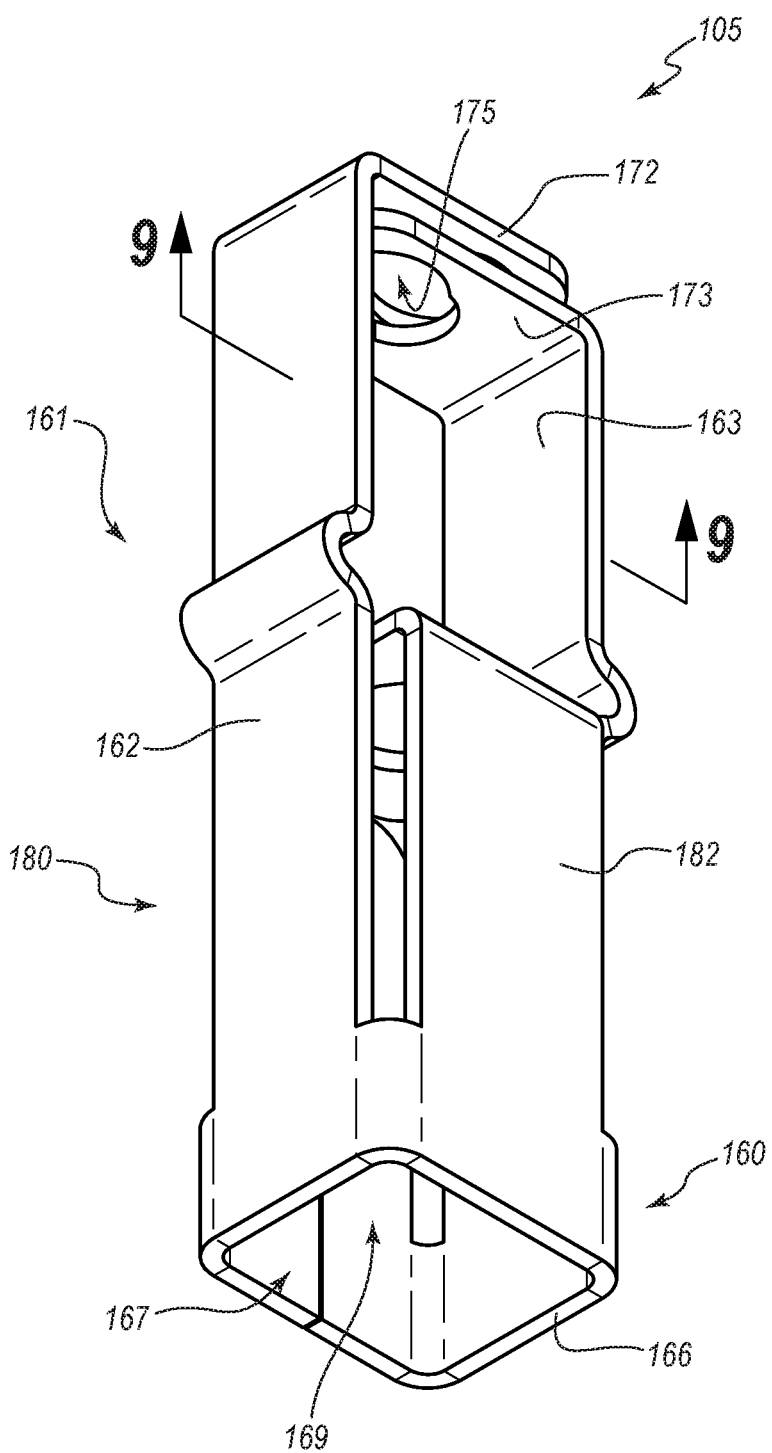
FIG. 7 is another perspective view of the shield of FIG. 6.

FIGS. 6 and 7 depict different perspective views of an illustrative embodiment of the shield 105, which may also be referred to as, for example, a safety shield, guard, clip, cover, or stick-prevention element. The shield 105 includes a body 161 that can be shaped in a desired form. In the illustrated embodiment, the body 161 comprises a single sheet of cut and folded metal (e.g., stainless steel). Although the illustrated shield 105 is formed entirely of a single, unitary, monolithic piece of material, other embodiments can include multiple separate components (e.g., as discussed below with respect to further illustrated embodiments).

In the illustrated embodiment, the shield 105 includes a collar 160 and a pair of arms 162, 163. The arms 162, 163 extend proximally from a proximal end of the collar 160. In the illustrated embodiment, the arms 162, 163 are resiliently flexible members. The arms 162, 163 may be formed such that they are in a natural, resting, non-deflected, nondisplaced, nondeformed, undistorted, unflexed, or relaxed state when in the low-profile orientation depicted in FIG. 6, or are at least closer to such a low-energy state than they are when moved to an outwardly displaced state, such as that depicted in FIGS. 10 and 11. For example, the arms 162, 163 may be deformed, displaced, flexed, or deflected laterally or radially outwardly away from a longitudinal axis of the shield 105 to achieve an orientation such as that depicted in FIGS. 10 and 11, which may give rise to an internal bias that naturally urges or otherwise influences the arms 162, 163 back toward their natural state and/or toward a lower energy state, which bias may thus be directed laterally or radially inwardly toward the longitudinal axis.

In other embodiments, the arms 162, 163 may provide little or no inward bias, or may even be biased outwardly. In such embodiments, other sources of inward bias may be provided. Illustrative examples are discussed further with respect to FIG. 43.

The shield 105 can define a distal end 164 and a proximal end 165. In the illustrated embodiment, the collar 160 is positioned at the distal end 164 of the shield. The illustrated collar 160 defines a substantially rectangular transverse cross-section, although other configurations are contemplated. The collar 160 can define a distal tip 166 or distal edge of the shield 105. In the illustrated embodiment, the distal tip 166 includes a substantially planar face.

The collar 160 can define a distal opening 167 through which the obturator can pass. In various embodiments, the distal opening 167 may define a fixedly open configuration. Stated otherwise, in some embodiments, the opening 167 is configured to remain open even after the distal tip 146 of the obturator 104 has been drawn into the shield 105. In other terms, the collar 160 may be substantially nondeformable or may define a single shape throughout full operation of the shield 105.

As further discussed below, in some embodiments, the collar 160 is capable of inhibiting or preventing undesired contact with the distal tip 146 of the obturator 104, although the distal opening 167 remains open when the shield 105 is locked onto the obturator 104. For example, the distal opening 167 may be sized to prevent the skin of a user or other individual from entering into a cavity 169 of the shield 105 to a sufficient distance to come into contact with the distal tip 146 of the obturator 104.

In the illustrated embodiment, the cavity 169 is generally defined by the collar 160, distal ends of the arms 162, 163, and a plurality of panels 181, 182, 183. Stated otherwise, a cage 180 may be defined by the collar 160, the arms 162, 163, and the panels 181, 182, 183. The cage 180 can prevent inadvertent contact with the distal tip 146 of the obturator 104 when the distal tip 146 has been drawn into the cavity 169 and is being retained therein. In the illustrated embodiment, the panel 183 is a lateral projection at a proximal end of the panel 182. The panel 183 can define a passageway 184 through which the obturator 104 can pass. The panel 183 may also be referred to as a guide.

In the illustrated embodiment, at the proximal end 165 of the shield 105, the arms 162, 163 define lateral extensions 172, 173, respectively, which may extend in opposite directions. The lateral extensions 172, 173 can define openings 174, 175 through which the obturator 104 can pass. The openings 174, 175 are discussed further below.

In some embodiments, one or more of the arms 162, 163 can define one or more connection interfaces 176, 177, respectively, that can engage the needle hub 203, as discussed further below. In the illustrated embodiment, the connection interfaces 176, 177 are directed outwardly so as to engage the needle hub 203 when the arms are deformed or distorted outwardly, and further, are held in this outward orientation by the larger diameter portion of the obturator 104. In the illustrated embodiment, the connection interfaces 176, 177 are formed as outwardly directed protrusions 178, 179. For example, in the illustrated embodiment, the protrusions 178, 179 are formed as outward bends in the arms 162, 163, respectively. The connection interfaces 176, 177 can be said to define contact regions that can interface with contact regions of the needle hub 203 in manners such as further described below. For example, the proximal surfaces of the protrusions 178, 179 can be configured to contact an underside, or proximal end, of an annular groove defined by the needle hub 203 to engage the shield 105 with the needle hub 203.

In various embodiments, the shield 105 may be formed of a unitary monolithic piece of material, or stated otherwise, may have a single-piece construction. For example, in some embodiments, the shield 105 may be formed of a single piece of sheet metal that has been folded and/or bent into the configuration depicted in FIGS. 5 and 6. For example, in the illustrated embodiment, the shield 105 is folded into a substantially rectangular form at four primary bends, one at each corner of the collar 160. Three additional bends yield each of the lateral extensions 172, 173, 183. In some embodiments, the additional bends (in some instances, three bends each) yield the outward protrusions 178, 179. Upon folding or bending the single sheet of metal, opposite edges of the sheet may be in contact or in close proximity with each other along a seam 185.

In other embodiments, the shield 105 may be injection molded, 3D-printed, or formed in any other suitable manner. In other or further embodiments, the shield 105 may be formed of multiple pieces that are joined together.

FIGS. 8 and 9 depict enlarged views of the lateral extensions 172, 173 of the arms 162, 163. The openings 174, 175 defined by the lateral extensions 172, 173 each can include two separate regions through which different portions of the obturator 104 can be received. Each opening 174, 175 can include a passageway or passage region 186, 187, respectively, that is sufficiently large to permit passage therethrough of a relatively larger portion of the obturator 104 that is proximal to the recess 150. Each opening 174, 175 can further include a receptacle, constriction, or constriction region 188, 189 that is smaller than the passage region 186, 187, respectively. Each receptacle or constriction region 188, 189 can receive a portion of the recess 150 of the obturator 104 (see FIG. 5). In the illustrated embodiment, each of the regions 186, 187, 188, 189 is substantially circular. The passage regions 186, 187 may be sized substantially the same as each other, and the constriction regions 188, 189 may likewise be sized substantially the same as each other, and a diameter of the passage regions 186, 187 may be larger than a diameter of the constriction regions 188, 189. A diameter of the passage regions 186 can be slightly larger than a diameter of the proximal end 140 of the obturator 104 to permit passage of the proximal portion 140 therethrough. The openings 174, 175 can substantially resemble oppositely directed rounded keyholes. In the illustrated embodiment, the openings 174, 175 each fully encompass the obturator 104.

Each of the lateral extensions 172, 173 can define a contact region 190, 191 that borders a portion of the opening 174, 175, respectively. Each contact region 191, 192 may include multiple contact surfaces. In the illustrated embodiment, each contact region 190, 191 includes an inwardly directed (e.g., radially directed) contact surface 192, 193, respectively, which are depicted by weighted lines. The contact surfaces 192, 193 are oriented to contact or abut, or closely approximate without touching, differently sized outer surfaces of the obturator 104, depending on the relative orientation of the shield 105 and the obturator 104. In particular, with continued reference to FIGS. 8 and 9, and with additional reference to FIG. 17B, when the shield 105 is positioned over proximal portions of the obturator 104 that define a larger outer diameter, the portions of the contact surfaces 192, 193 that border the passage regions 186, 187 contact the outer surface of the obturator 104. Further, with reference to FIGS. 8 and 9, and with additional reference to FIG. 17B, when the obturator 104 is moved proximally relative to the shield 105 to a position where the lateral extensions 172, 173 of the shield 105 are approximately even with the groove 151 of the obturator, the arms 162, 163 spring inward and the portions of the contact surfaces 192, 193 that border the constriction regions 188, 189 can, in some embodiments, contact the base surface 152 of the groove 151. In other embodiments, the surfaces 192, 193 may instead come into close proximity to the base surface 152 of the groove 151, but might not come into contact therewith. Thus, in some embodiments, the contact surfaces 192, 193 contact a portion of the obturator 104 in each of the unlocked and locked conditions, whereas in other embodiments, the contact surfaces 192, 193 contact an outer surface of the obturator 104 when the shield 105 is in the unlocked condition—thereby maintaining the shield 105 in the unlocked condition—but the contact surfaces 192, 193 do not contact the obturator 104 (e.g., do not contact the groove 151) when the shield 105 is in the locked condition.

Stated otherwise, the contact surface 192 can include two opposing portions that each border the passage region 186. These opposing portions of the contact surface 192 can contact the outer surface of a relatively larger proximal portion of the obturator 104 when the obturator 104 extends fully through the shield 105. (See FIGS. 5 and 17A). Upon retraction of the obturator 104 through the shield 105, the opposing portions of the contact surface 192 can slide along the proximal portion of the obturator, and can maintain the arm 162 in the deflected orientation (see FIG. 17B). Further proximal withdrawal of the obturator 104 relative to the shield 105 can orient the contact surface 192 over the recess 150 (see FIGS. 5 and 17C). Due to the internal bias of the arm 162, the arm 162 can naturally move inward. The inward movement can, in some embodiments, bring a portion of the contact surface 192 that bridges the opposing portions described above and that borders the constriction region 188 into contact with the base surface 151 of the recess 150. In other embodiments, the bridge portion of the contact surface 192 is instead brought into close proximity to the base surface 151 of the recess 150, but does not touch the base surface 151. The contact surface 193 can function in the same manner as the contact surface 192, as just described, but in the opposite direction.

Each contact region 190, 191 may further include a contact surface or contact face 194, 195 that is configured to contact or abut one of the proximal or distal faces 154, 156 of the groove 151 of the obturator 104 (see FIGS. 5 and 17C), respectively. The contact faces 194, 195 may also be referred to as proximal and distal faces 194, 195, respectively. In certain embodiments, when the bridge portion of the contact surface 192 is brought into contact with or close proximity to the base surface 152 of the recess 150, the contact face 194 can be in contact with or in close proximity to the proximal face 154 of the recess 150 (see FIG. 17C). Cooperation between the contact face 194 of the arm 162 and the proximal face 154 of the recess 150 can delimit movement of the shield 105 in the proximal direction, relative to the obturator 104. In like manner, when the bridge portion of the contact surface 193 is brought into contact with or close proximity to the base surface 152 of the recess 150, the contact face 195 can be in contact with or in close proximity to the distal face 156 of the recess 150 (see FIG. 17C). Cooperation between the contact face 195 of the arm 163 and the distal face 156 of the recess 150 can delimit movement of the shield 105 in the distal direction, relative to the obturator 104.

When the shield 105 is in the unlocked state, the passageways 186, 187 can be substantially aligned with each other, or stated otherwise, may be only slightly misaligned due to a small amount of clearance between the inner diameter of the passageways 186, 187 and the outer diameter of the proximal portion of the obturator 104, which can permit the passageways 186, 187 to move in opposite directions by a small amount to achieve contact with the obturator 104. Conversely, the constrictions 188, 189 can be misaligned when the shield 105 is in the unlocked state. When the shield 105 transitions to the locked state, the constrictions 188, 189 can be brought into substantial alignment with each other, or stated otherwise, may be moved into an only slightly misaligned orientation due to a small amount of clearance between the inner diameter of the constrictions 188, 189 and the base surface 152 of the recess 150. Conversely, the passageways 186, 187 move out of substantial alignment, or stated otherwise become misaligned, when the shield 105 transitions to the locked state.

Figure 10:
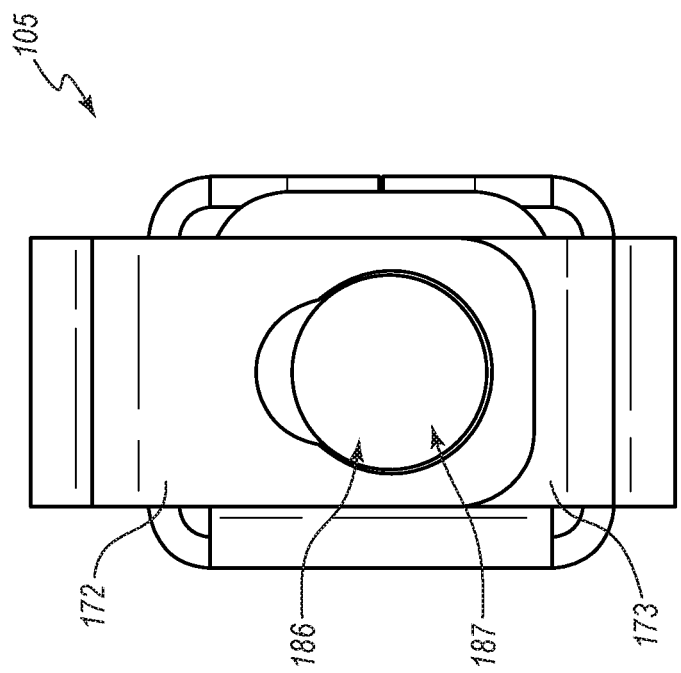
FIG. 10 is a top plan view of the shield.

FIG. 10 is a top plan view of the shield 105 when in the unlocked state. This image depicts the general alignment of the passageways 186, 187 of the lateral extensions 172, 173 when the shield 105 is in this operational state.

Figure 11:
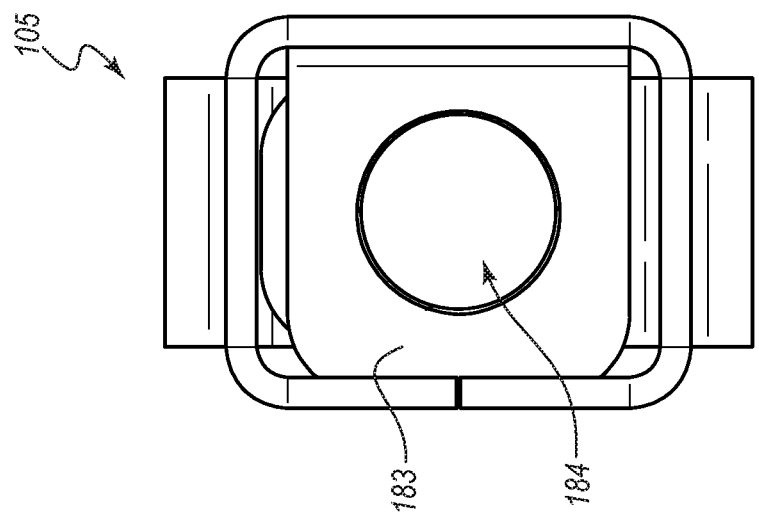
FIG. 11 is a bottom plan view of the shield.

FIG. 11 is a bottom plan view of the shield 105 when in the unlocked state. FIGS. 10 and 11 depict that, in addition to being generally aligned with each other, the passageways 186, 187 can be aligned with the passageway 184 of the guide 183 when the shield 105 is in the unlocked state. When the shield 105 transitions to the locked state, the passageway 184 of the guide 183 can be aligned with the constrictions 188, 189 as these latter regions come into alignment with each other. The guide 183 thus can help stabilize the shield 105 relative to the obturator 104 or, stated otherwise, can inhibit or prevent rotation of the shield 105 about any axes that are orthogonal to a longitudinal axis of the obturator 104, when the shield is in, and is transitioned from one to the other of, the unlocked state and the locked state. Stated otherwise, the guide 183 can help maintain a longitudinal alignment of the shield 105 and the obturator 104. Such longitudinal alignment can, for example, prevent the distal tip 166 of the shield 105 from catching on the distal wall 156 of the groove 151 as the obturator 104 is drawn proximally through the shield 105. Stated in yet another manner, the guide 183 can restrict lateral movement of the shield 105.

Figure 12:
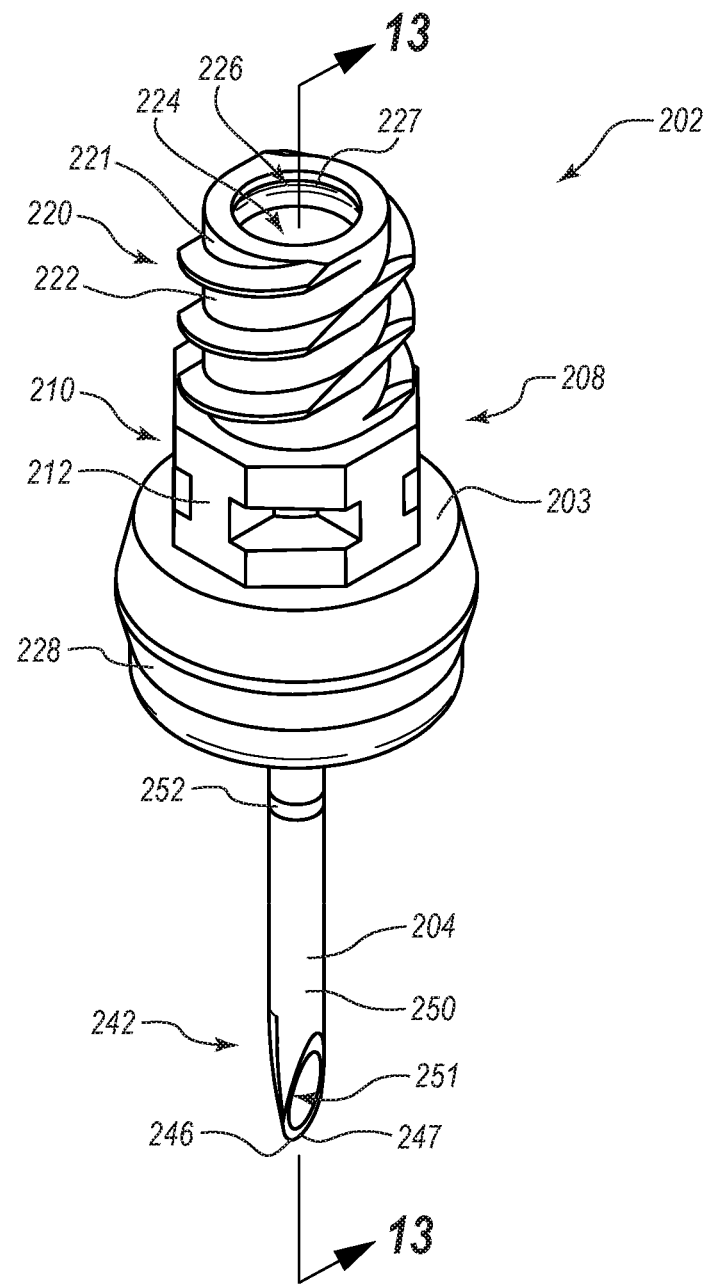
FIG. 12 is a perspective view of an embodiment of a needle assembly portion of the intraosseous access system of FIG. 1.
Figure 13:
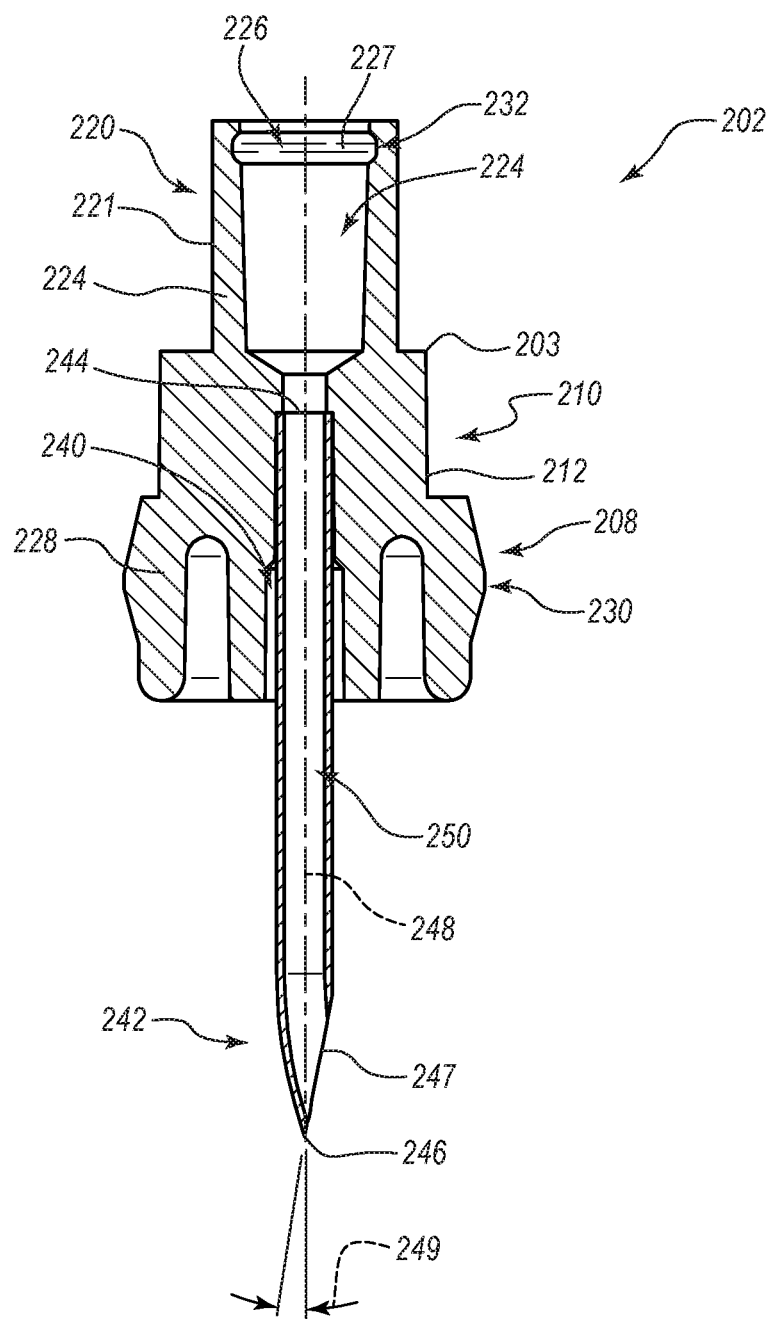
FIG. 13 is a cross-sectional view of the needle assembly taken along the view line 13-13 in FIG. 12.
Figure 14:
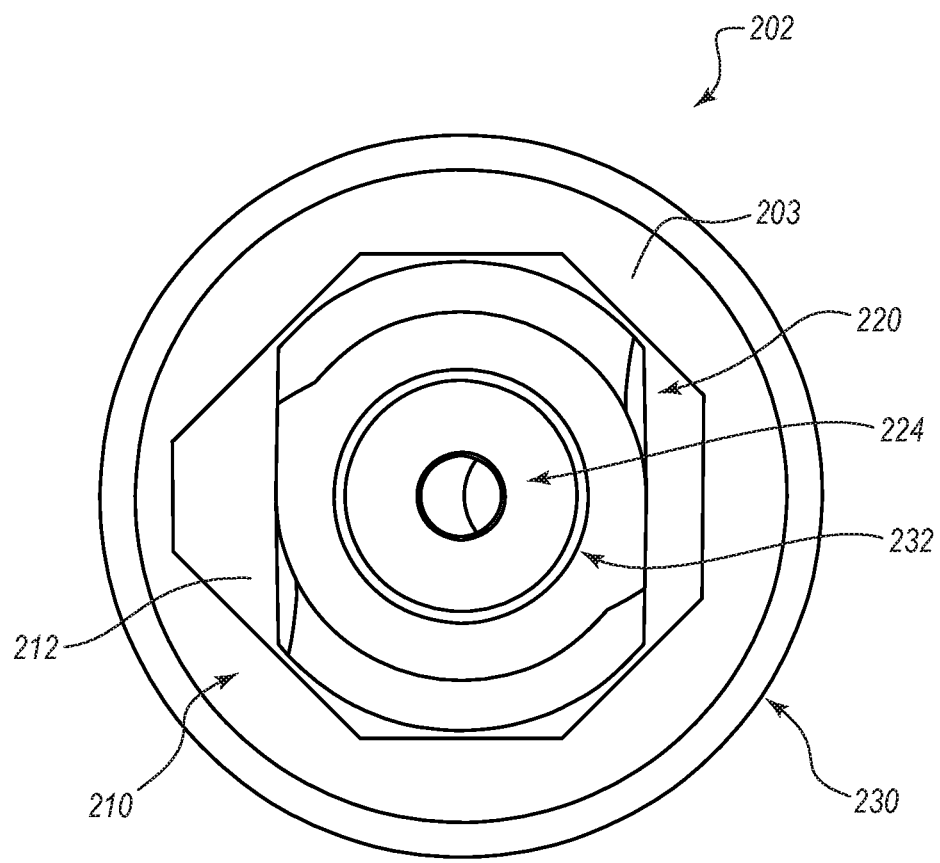
FIG. 14 is a top plan view of the needle assembly.

With reference to FIGS. 12-14, as previously discussed, the needle assembly 202 can include the needle hub 203 and the needle 204, which can be fixedly secured to each other. Further, as previously discussed, the needle hub 203 and the needle 204 may more generally be referred to as a cannula hub and as a cannula, respectively.

In the illustrated embodiment, the needle hub 203 includes a housing or body 208. The body 208 can define a coupling interface 210 that is configured to couple with the coupling interface 137 of the coupling hub 102 (see FIG. 4). For example, the coupling interface 210 can be formed as a shaft 212 that is configured to be received within the socket 138 of the coupling hub 102 (see FIG. 4). As shown in FIG. 14, in some embodiments, the shaft 212 can define a keyed shape that permits the needle hub 203 to be coupled to the coupling hub 103 in only one unique rotational or angular orientation. In particular, in the illustrated embodiment, the shaft 212 defines an elongated right octagonal prism of which five contiguous sides are substantially identically sized, two enlarged sides that extend from the ends of the five contiguous sides are lengthened relative to the five contiguous sides, and an eighth shorted side that extends between the two enlarged sides is shorter than the five contiguous sides. Any other suitable keying configuration is contemplated.

The needle hub 202 can further include a connector 220, e.g., a medical connector, of any suitable variety. The connector 220 may be defined by the housing 208 and may extend proximally from the shaft 212. The connector 220 can be configured to couple with any suitable medical equipment, such as for infusing fluid into a patient, after the needle 204 has been inserted into bone. For example, in the illustrated embodiment, the connector 220 is formed as a Luer fitting 221 (i.e., a female Luer fitting). The illustrated Luer fitting 221 includes a sidewall 222 that defines a cavity or lumen 224. In some embodiments, a portion of a male Luer fitting may be received within the lumen 224 when the needle hub 202 is in use. The lumen 224 of the connector 220 can be in fluid communication with a lumen 251 of the needle 204, which is discussed further below.

In the illustrated embodiment, the sidewall 222 defines a connection interface 226 that is configured to couple the needle hub 202 with the shield 105 when the shield 105 is in the unlocked state. For example, in the illustrated embodiment, the connection interface 226 is formed as an annular groove 227 within which the outward protrusions 178, 179 of the shield 105 (see FIGS. 6, 15, and 17A) can be received. The connection interface 226 may be said to define a contact surface or a contact region (e.g., a proximal surface of the groove 227). As discussed further hereafter, a portion of the shield 105 can abut, interfere with, or otherwise interface with the contact surface or contact region of the connection interface 226 to maintain the shield 105 coupled with the needle hub 202.

The housing 208 may further define a skirt 228, which may extend distally from the shaft 212. The skirt 228 may also extend outwardly relative to the shaft 212. As shown in FIG. 14, the skirt 228 may define a maximum transverse perimeter 230 of the hub 202. In the illustrated embodiment, the maximum transverse perimeter 230 is substantially circular. The maximum transverse perimeter 230 represents an outline of the needle assembly 202 when the assembly 202 is viewed from above or below, or stated otherwise, is viewed along a longitudinal axis of the needle assembly 202.

With continued reference to FIG. 14, an upper interior edge of the sidewall 222 can define a maximum transverse perimeter 232 of the lumen 224. In the illustrated embodiment, the maximum transverse perimeter 232 is substantially circular. In the illustrated embodiment, the maximum transverse perimeter 232 represents an outline of the lumen 224 when the assembly 202 is viewed from above, or stated otherwise, is viewed along a longitudinal axis of the needle assembly 202. In other embodiments, the maximum transverse perimeter 232 may be defined a portion of the sidewall 222 that is positioned further down, within the lumen 224, and may not be visible in a plan view such as that of FIG. 14.

With reference again to FIGS. 12 and 13, the needle 204 can include a proximal end 240 and a distal end 242. The proximal end 240 terminates at a proximal tip 244, and the distal end 242 terminates at a distal tip 246. The proximal end 240 can be fixedly secured to the housing 208 in any suitable manner.

The distal end 242 of the needle 204 can include a distal face 247. In some embodiments, the distal face 247 is formed as a bevel that is at an angle relative to a central longitudinal axis 248 of the needle 204. For example, in the illustrated embodiment, the distal face 247 defines a substantially planar bevel. The beveled distal face 247 can be formed in any suitable manner, such as by grinding. For example, the distal face 247 that is substantially planar may be formed by a bias grind (which may also be referred to as a simple bias grind). The illustrated distal face 247 is at an angle 249 relative to the central longitudinal axis 248. Any suitable value of the angle 249 is contemplated. For example, in various embodiments, the angle 249 is within a range of from about 8 degrees to about 20 degrees; is no less than about 8, 10, 15, or 20 degrees; or is no greater than about 8, 10, 15, or 20 degrees. In some embodiments, the angle 249 is 11 degrees.

When the needle 204 is advanced in a distal direction, the distal face 247 can pierce or cut through tissue. When the needle 204 is rotated, the distal face 247 can cut tissue. In some instances, cutting of bone material is facilitated by rotation of the needle 204 to effect cutting via the distal face 247 and/or the angled region that extends around a periphery thereof, particularly the lower or distal portion of the periphery. The distal face 247 and/or the angled periphery thereof may also be referred to as a cutting portion, cutting face, or cutting surface of the needle 204. The distal end 242 of the needle 204 may also be referred to as the cutting portion of the needle 204.

The needle 204 can be configured to cut bi-directionally. Stated otherwise, the needle 024 can be configured to cut tissue and/or bone whether it is rotated in a first direction or a second direction that is opposite the first direction. For example, with reference to FIG. 12, when the illustrated needle 110 is rotated about the central longitudinal axis 248 in a clockwise direction, a right portion of the distal face 247 and/or adjacent angled regions can cut as the needle 204 is rotated. Likewise, when the illustrated needle 204 is rotated about the central longitudinal axis 248 in a counterclockwise direction, a left portion of the distal face 247 and/or adjacent angled regions can cut as the needle 204 is rotated. In some instances, such as during certain drilling procedures in which the automated driver 108 is used, the needle 204 may be rotated in only one of the first or second directions. In other instances, such as during certain manual manipulation procedures, the needle 204 may be rotated back and forth and can cut throughout each stroke of the back-and-forth motion.

In certain embodiments, the distal face 247 can include a plurality of facets. For example, in some embodiments, lancet grinding may be applied to a bias bevel to yield a lancet point. In certain of such embodiments, the distal face 247 can include three facets, which in some instances, can define three distinct planes. Any other suitable arrangement for the distal face 247 is contemplated.

With reference again to FIG. 12, the needle 204 can include a shaft 250 that extends between the proximal and distal ends 240, 242. The shaft 250 can include an interior surface that defines a lumen 251 of the needle 204. An exterior surface of the shaft 250 can include one or more depth markers 252 of any suitable variety.

Figure 15:
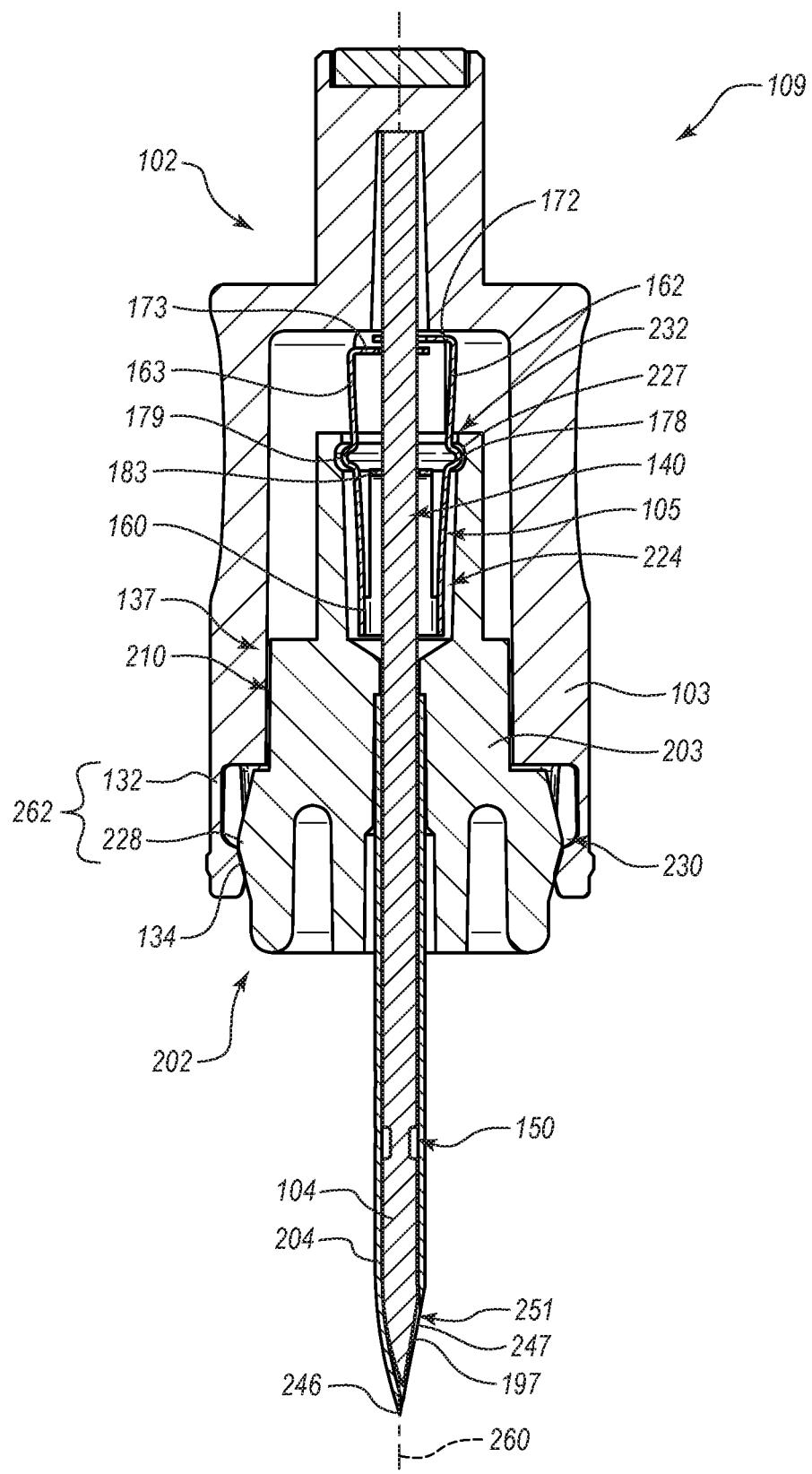
FIG. 15 is a cross-sectional view of an access assembly portion of the intraosseous access system of FIG. 1 in an assembled state, the access assembly including the obturator assembly, the shield, and the needle assembly.

FIG. 15 depicts the access assembly 109 in an assembled state. As previously discussed, the keyed coupling interfaces 137, 210 of the coupling hub 103 and the needle hub 203, respectively, can cooperate to ensure that a predetermined relationship between the obturator 104 and the needle 204 is achieved. Stated otherwise, the keyed coupling interfaces 137, 210 can ensure that the obturator 104 defines a fixed angular orientation relative to the needle 204. The coupling interfaces 137, 210 may likewise maintain the fixed angular orientation during rotation of the access assembly 109 during an insertion event, e.g., during rotation of the access assembly 109 via the automated driver 108.

In the illustrated embodiment, the distal face 197 of the obturator 104 is slightly recessed relative to the distal face 247 of the needle 204. Additionally, in the illustrated embodiment, the distal faces 197, 247 of the obturator 104 and the needle 204, respectively, are substantially parallel to each other. In some embodiments, the obturator 104 does not cut either through skin or bone during an insertion event. In other embodiments, the distal faces 197, 247 may be substantially flush with each other. The obturator 104 can substantially fill or otherwise block passage into the lumen 251 of the needle 204. For example, in the illustrated embodiment, the distal face 197 of the obturator 104 is substantially the same size as an opening into a distal end of the lumen 251. The obturator 104 can inhibit or prevent tissue and/or bone material from entering and/or progressing into the lumen 250 of the needle 204. In the illustrated embodiment, the distal faces 197, 247 of the obturator 104 and the needle 204 may be orientated at substantially the same angle relative to a longitudinal axis 260 of the access assembly 109.

With continued reference to FIG. 15, during assembly of the access assembly 109, the arms or projections 132 can be advanced over the skirt 228 of the needle hub 203. The snap interface or inward protrusions 134 of the projections 132 can grip an underside of the skirt 228 to maintain the coupling hub 103 and the needle hub 203 in a coupled state. In the illustrated embodiment, the skirt 228 is shaped substantially as an outward protrusion, and the inner surface of the arm 132 substantially defines a recess into which the protrusion is received. In other embodiments, the protrusion/recess interface may be reversed. For example, the arm 132 may define a protrusion is received into a recess defined by the skirt 228 to couple the obturator hub 103 with the needle hub 203.

The projection 132 and the hub 228 may collectively be referred to as a releasable engagement mechanism 262. The releasable engagement mechanism 262 may be configured to keep the obturator hub 103 and the needle hub 203 coupled together during general manipulation of the access assembly 109, such as during removal from packaging and/or coupling thereof with the automated driver 108. The releasable engagement mechanism 262 may, however, provide a relatively weak coupling that is capable of being released upon application of sufficient removal force to the coupling hub 103 in a proximal direction, relative to the needle hub 203. For example, the releasable engagement mechanism 262 may provide a coupling force that tends to keep the coupling hub 103 engaged with the needle hub 203. When a proximally directed force exceeds the coupling force of the releasable engagement mechanism 262, the releasable engagement mechanism 262 can disengage and permit the coupling hub 103 to be withdrawn from the needle hub 203. In various embodiments, the coupling force (i.e., the force that counteracts a proximally directed force on the coupling hub 103) can be no greater than about 0.25, 0.5, 0.75, 1.0, 1.5, or 2.0 pounds.

In certain embodiments, the releasable engagement mechanism 262 provides a coupling force that is significantly lower than an embedding force between the needle 204 and a bone within which the needle 204 is inserted. Stated otherwise, the releasable engagement mechanism can be configured to permit the coupling hub 103 to be decoupled from the cannula hub 203, after the cannula hub 203 has been introduced into the bone, by imparting a proximally directed force on the coupling hub 103 that is smaller in magnitude than a force imparted on the cannula 204 by the bone that maintains the cannula 204 positioned in the bone.

Accordingly, in some embodiments, after introducing the access assembly 109 into the bone, a user may simply pull back, or proximally, on the obturator hub 103 with any amount of force that exceeds the coupling force of the releasable engagement mechanism 262, and the obturator hub 103 will automatically disengage from the needle hub 203. Further, the obturator hub 103 can be withdrawn from the needle hub 203 and the patient, and the needle hub 203 can remain in the bone. In some instances, the user can remove the hub 103 from the needle hub 203 using a single hand after the access assembly 109 has been introduced into the bone. Other suitable arrangements of the releasable engagement mechanism 262 are contemplated.

With continued reference to FIG. 15, when the access assembly 109 is in the assembled state, the shield 105 can be coupled with each of the obturator 104 and the needle hub 204 in the unlocked state. In particular, the proximal end 140 of the obturator 104, which can define a larger diameter than does the recess 150, can extend through an entirety of the shield 105. Stated otherwise, the proximal end 140 of the obturator 104 extends through the lateral extensions 172, 173, the guide 183, and the collar 160. As further discussed below, this larger diameter region of the obturator 104 can maintain the shield 105 in the unlocked state to permit the obturator 104 to translate relative to the shield 105 in a proximal direction when the user desires to remove the obturator hub 103 from the needle hub 204.

When the shield 105 is in the unlocked state, the arms are deflected outwardly, which can seat or otherwise position the outward protrusions 178, 179 of the arms 162, 163 respectively within the groove 178 of the needle hub 203. The outward protrusions 178, 179 thus can cooperate with the groove 178 to maintain the shield 105 in a fixed longitudinal position relative to the needle hub 203 during the initial stages of withdrawal of the obturator 104 through the shield 105. In other embodiments, the groove 178 and the outward protrusions 178, 179 can be reversed. For example, in some embodiments, an inner surface of the needle hub 203 may define one or more inward protrusions, and the arms 162, 163 may define inward recesses into which the inward protrusions are received when the shield 105 is in the unlocked state (relative to the obturator 104) and in the coupled state relative to the needle hub 203.

With continued reference to FIG. 15, when in the assembled state, which may also be referred to as a pre-use or drilling state, the shield defines a low-profile configuration that is relatively close to the longitudinal axis 260 of the access assembly 109. The longitudinal axis 260 may also be referred to as a central axis or as an axis of rotation. That is, during insertion of a distal end of the access assembly 109 into the bone of a patient, the access assembly 109 can be rotated about the axis 260. In many instances, the rotation can be very rapid, such as when the access assembly 109 is coupled with the automated driver 108. In some instances, by defining a low-profile configuration that is close to the rotational axis, the shield 105 can have a low rotational moment of inertia that permits the shield 105 to spin up to speed rapidly and/or permits the shield 105 to stop spinning rapidly once the access assembly 109 in inserted into the bone. The shield 105 may also be relatively lightweight, which can also contribute to a relatively low rotational moment of inertia.

In some instances, the shield 105 may be substantially rotational fixed relative to the needle hub 203 and the obturator hub 103 during an insertion event. For example, frictional engagement between the arms 172, 173 and the obturator 104 and/or between the arms 172, 173 and the needle hub 203 may be sufficient to maintain the shield 105 in a substantially fixed relationship (e.g., a fixed angular position) relative to the obturator 104 and the needle hub 203 during spin-up and/or upon discontinuing spinning of the access assembly 109 during an insertion event. In other or further embodiments, one or more protrusions or other keying members (not shown) may extend inwardly from the groove 227 and can interface with opposing faces of each of the protrusions 178, 179 to lock the shield 105 in a rotationally fixed orientation relative to the needle hub 203. In other embodiments, the shield 105 may spin relative to the obturator 104 and/or the needle hub 203, at least temporarily, during spin-up. In further embodiments, the shield 105 may then come up to speed and thereafter rotate in unison, at least temporarily, with the assembly 109 during an insertion event.

As previously mentioned, in some embodiments, the shield 105 may define a low radial profile, which can be advantageous. For example, the low radial profile can permit quicker spin up, can yield a rotationally balanced system that is less susceptible to wobbling during an insertion event, and/or can be less susceptible to damage or malfunction. In the illustrated embodiment, no portion of the shield 105 extends laterally outward beyond the maximum transvers perimeter 232 of the lumen 224 of the needle hub 203. Stated otherwise, as viewed along the rotational axis 260, no portion of the shield 105 extends away from the rotational axis 260 by a greater distance than does the maximum transverse perimeter 232 of the lumen 224.

In the illustrated embodiment, no portion of the shield 105 extends laterally outward beyond the maximum transvers perimeter 230 of the needle hub 203. Stated otherwise, as viewed along the rotational axis 260, no portion of the shield 105 extends away from the rotational axis 260 by a greater distance than does the maximum transverse perimeter 230 of the needle hub 203.

With continued reference to FIG. 15, in some embodiments, the distal tip 246 of the needle 204 is positioned in close proximity to the central longitudinal axis 260 of the needle 204. For example, in the illustrated embodiment, the needle tip 246 is positioned directly on the central longitudinal axis 260. In other embodiments, the needle tip 246 may be laterally spaced from the longitudinal axis 260 by a distance that is no greater than 5, 10, 20, or 25 percent of a maximum lateral dimension (e.g., maximum outer diameter) of the needle 204.

In certain embodiments, the distal end of the needle 204 differs from some standard varieties of needles, such as Tuohy, Huber, or other needles with bent tips. Although such needles can include rounded regions and/or one or more beveled edges at their distal ends, similar to those discussed above, their distal tips are generally not in close proximity to the central longitudinal axis. In certain embodiments, the distal end of the needle 204 likewise differs from other standard varieties of needles, such as standard IV needles, including lancet, single-bevel, or other needles with non-bent tips. The distal tips of such needles likewise are generally not in close proximity to the central longitudinal axis. Accordingly, certain needles of this type may wobble against a surface during rotation (e.g., during drilling). Such wobbling can complicate boring through hard bone structures, for example. In some embodiments, the needle 204 is better suited for drilling into bone than standard needles may be.

Figure 16:
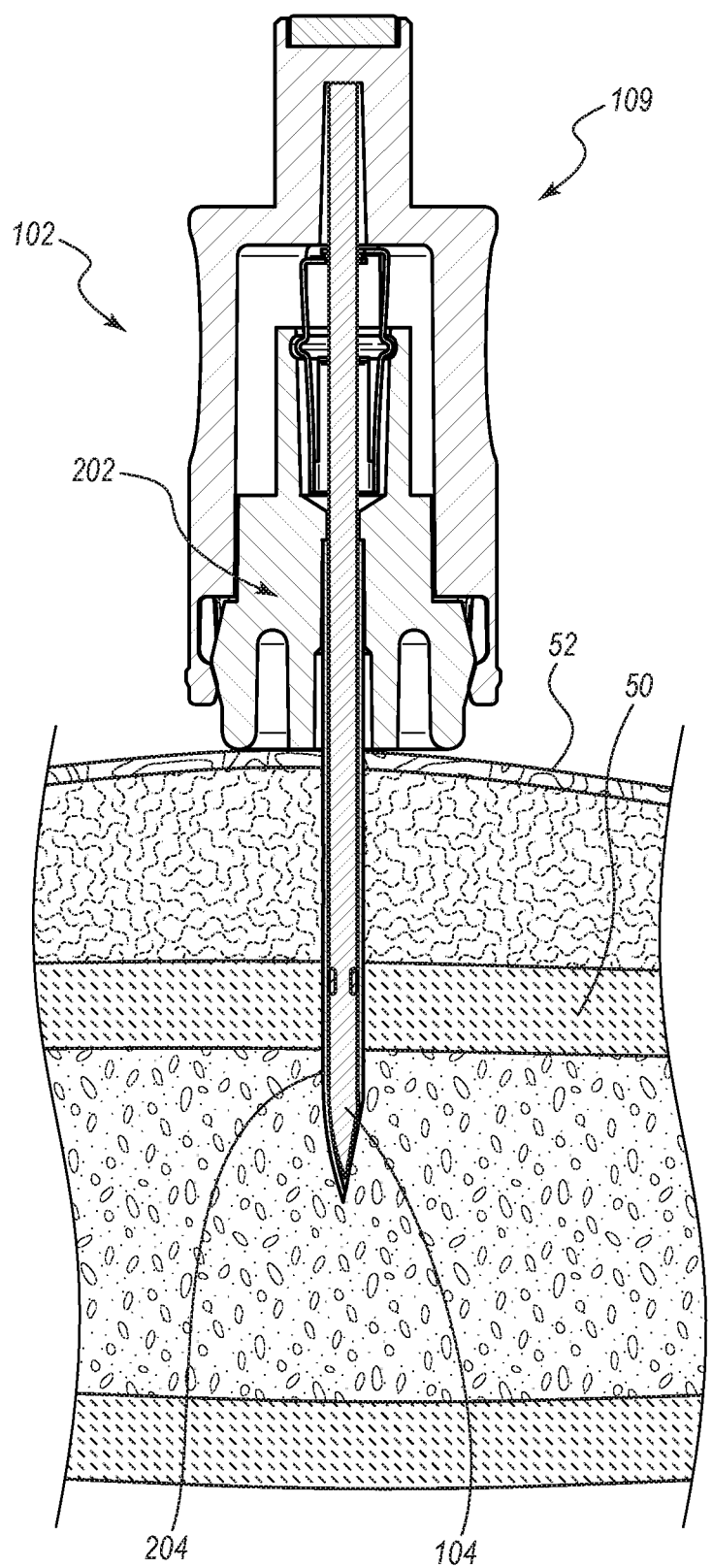
FIG. 16 is a cross-sectional view of the access assembly after it has been used to provide access to an interior of a bone of a patient in a stage of an illustrative method of using the access assembly.

FIG. 16 is a cross-sectional view of the access assembly 109 after it has been used to provide access to an interior of a bone 50 of a patient 52. FIG. 16 represents a stage of an illustrative method of using the access assembly 109. For example, prior to the depicted stage, the access assembly 109 can be coupled with the automated driver 108 in manners such as previously disclosed. The user can then actuate the driver 108 via the actuator 111 thereof (see FIG. 2) and press down to drill the needle 204 and the obturator 104 into the bone 50. The automated driver 108 can then be removed from the access assembly 109, as shown.

After the stage depicted in FIG. 16, the obturator assembly 102 can be removed from the needle assembly 202. In the illustrated embodiment, the obturator assembly 102 can be removed by pulling it in a proximal direction. Removal of the obturator assembly 102 is described in further detail below with respect to FIGS. 17A-17D.

Figure 17A:
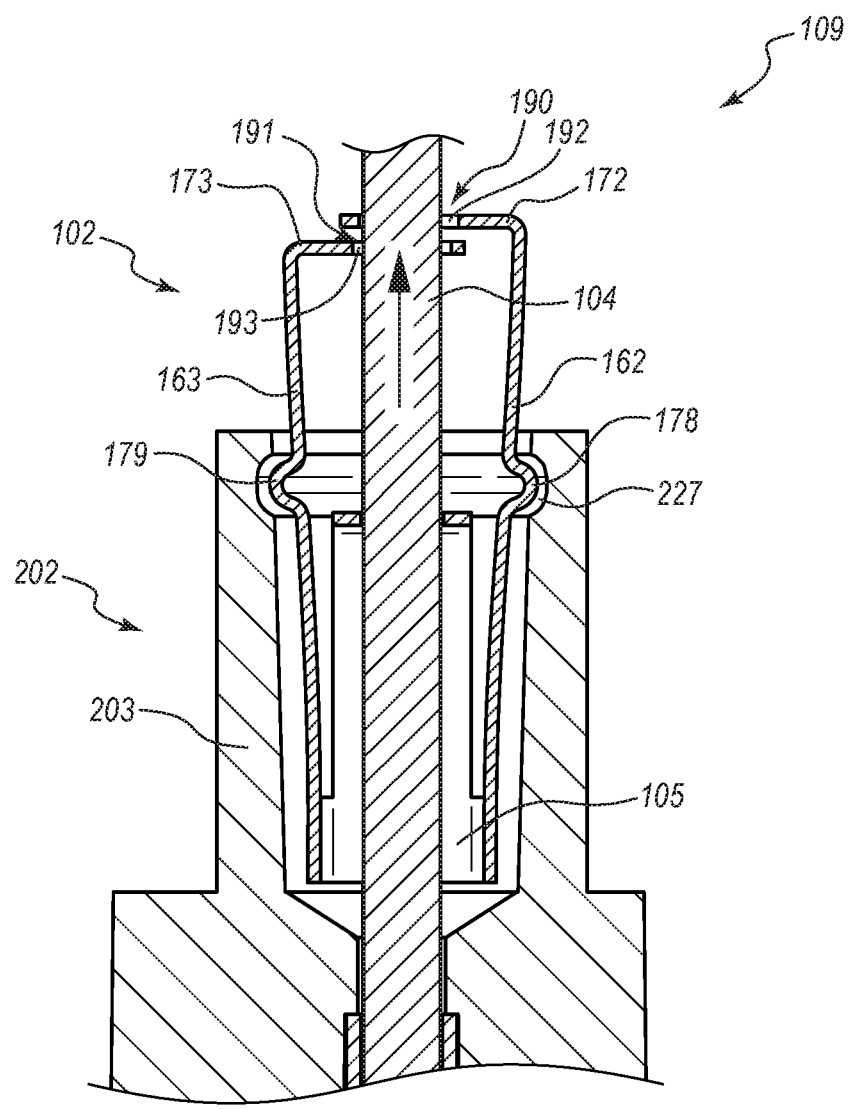
FIG. 17A is an enlarged cross-sectional view of a portion of the access assembly, with an obturator hub portion thereof not being shown for purposes of clarity, at a stage of the illustrative method, subsequent to the stage of FIG. 16, in which the obturator assembly is being decoupled and withdrawn from the needle assembly while the shield is in an unlocked state relative to an obturator, and is in a coupling state relative to a needle hub.

FIG. 17A is an enlarged cross-sectional view of a portion of the access assembly 109 at a stage of the illustrative method that is subsequent to the stage depicted in FIG. 16. For purposes of clarity, the obturator hub 103 is not shown, although it would still be present in the depicted view. In the illustrated stage, the obturator assembly 102 is being decoupled and withdrawn from the needle assembly 202, as depicted by the upwardly directed arrow.

The shield 105 can remain in substantially the same orientation as that depicted in FIGS. 15 and 16 and described with respect thereto. In particular, the shield 105 can remain in the unlocked state due to the relatively large diameter of the obturator 104. In particular, as described above with respect to FIGS. 8 and 9, the obturator 104 can be sufficiently large that the contact surfaces 192, 193 of the contact regions 190, 191, respectively, translate along the outer surface of the obturator 104. Stated otherwise, the obturator 104 may be sufficiently small to slide or otherwise translate with in the passageways 186, 187, but may be too large to fit into the constrictions 188, 189 depicted in FIGS. 8 and 9. Accordingly, the contact surfaces 192, 193 can press against the outer surface of the obturator 104 to maintain the arms 162, 163 in the outwardly deflected or displaced state. This outward deflection secures the outward protrusions 178, 179 within the groove 227 of the needle hub 203. The shield 105 thus remains coupled to the needle hub 203. The unlocked stated may also be referred to as an expanded, laterally displaced, deflected, or released state. The outer surface of the proximal portion of the obturator 104, or stated otherwise, the outer surface of the obturator 104 that is proximal of the recess 150, may also be referred to as a contact surface of the obturator.

Figure 17B:
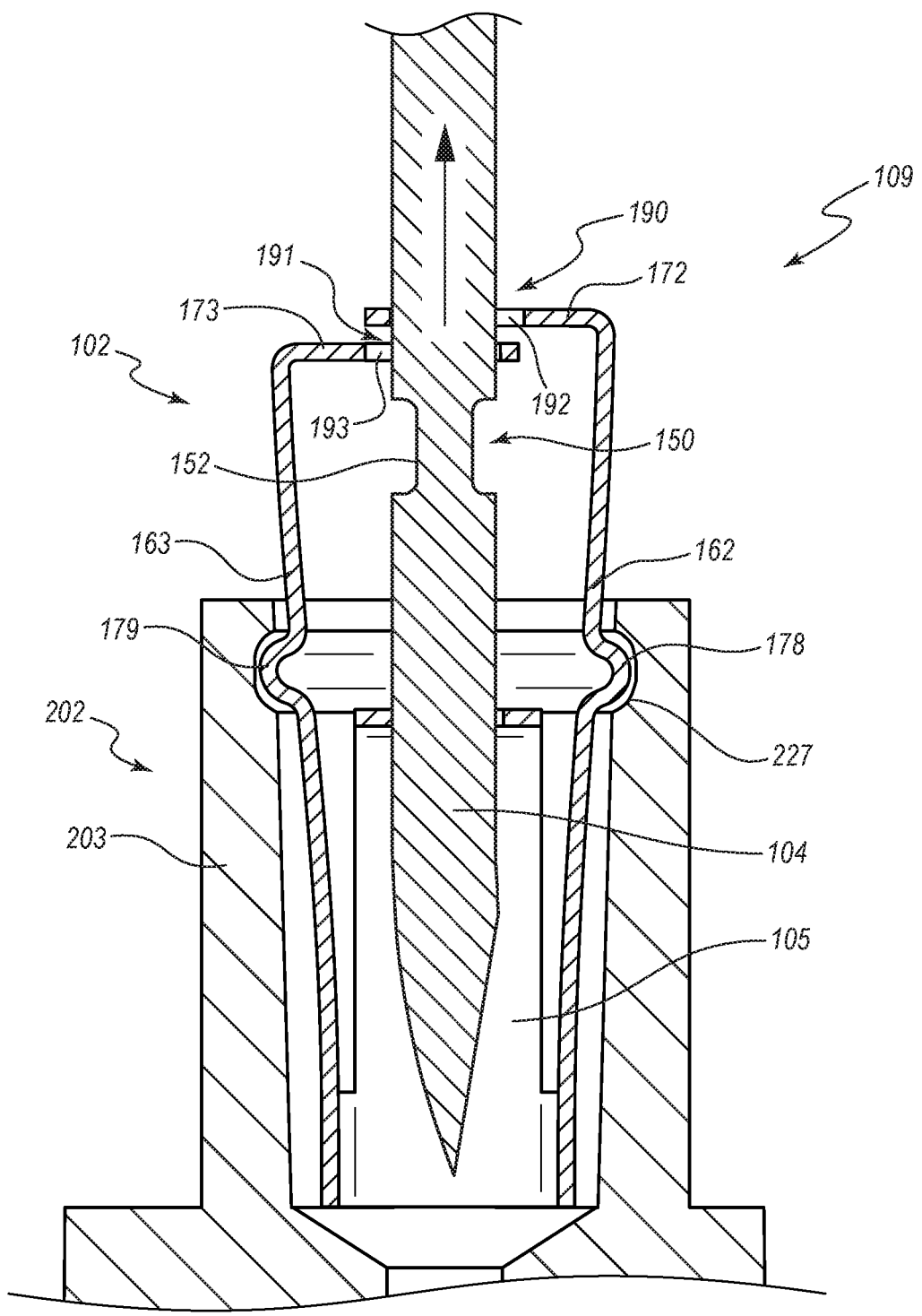
FIG. 17B is another enlarged cross-sectional view of the access assembly such as that of FIG. 17A at a subsequent stage of the illustrative method in which the obturator assembly is being further withdrawn from the needle assembly while the shield is in the unlocked and coupling states.

FIG. 17B is another enlarged cross-sectional view of the access assembly 109 at a subsequent stage of the illustrative method. In the illustrated stage, the obturator assembly 102 continues to be decoupled and withdrawn from the needle assembly 202, as depicted by the upwardly directed arrow.

The shield 105 can remain in substantially the same orientation as that depicted in FIGS. 15, 16, and 17A and described with respect thereto. In particular, the shield 105 can remain in the unlocked state due to the relatively large diameter of the obturator 104, which may be substantially constant along the full proximal end of the obturator 104. The contact surfaces 192, 193 of the contact regions 190, 191, respectively, can continue to translate along the outer surface of the obturator 104 and can continue to maintain the arms 162, 163 in the outwardly deflected or displaced state. This outward deflection secures the outward protrusions 178, 179 within the groove 227 of the needle hub 203, or stated otherwise, forces the protrusions 178, 179 into engagement with the groove 227, which thereby restricts or prevents longitudinal movement of the shield 105 relative to the needle hub 203. The shield 105 thus remains coupled to the needle hub 203

Figure 17C:
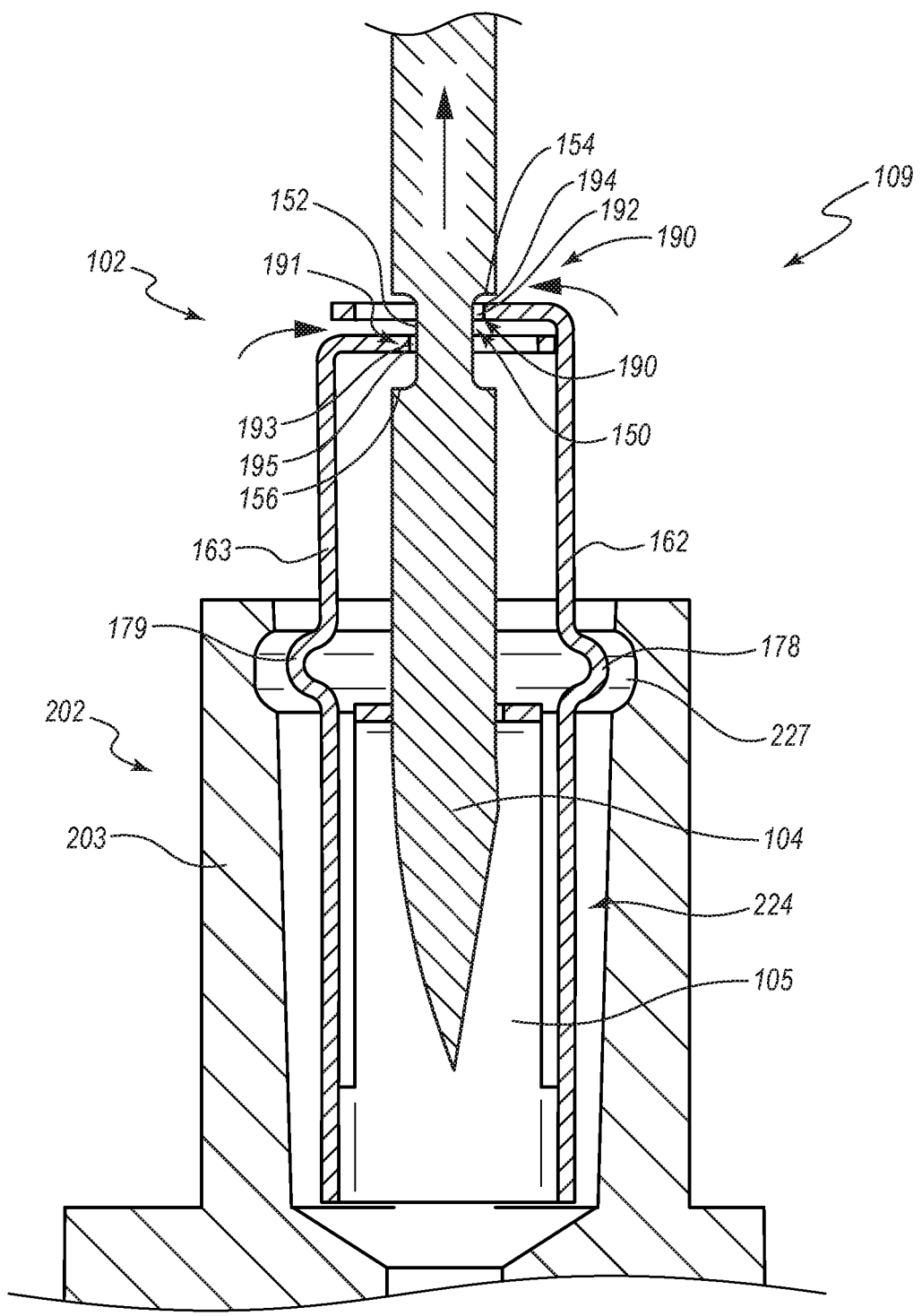
FIG. 17C is another enlarged cross-sectional view of the access assembly such as that of FIG. 17A at a subsequent stage of the illustrative method in which the obturator assembly is being further withdrawn from the needle assembly and in which the shield transitions from the unlocked state to a locked state relative to the obturator, and transitions from the coupling state to a decoupling state relative to the needle hub.

FIG. 17C is another enlarged cross-sectional view of the access assembly 109 at a subsequent stage of the illustrative method. In the illustrated stage, the obturator assembly 102 continues to be decoupled and withdrawn from the needle assembly 202, as depicted by the upwardly directed arrow.

The obturator 104 has been withdrawn proximally by a sufficient amount to bring the recess 150 into the vicinity of the lateral extensions of the arms 162, 163. Due to the reduced diameter of the recess 150, the arms 162, 163 are permitted to automatically transition, under the influence of the continuous internal bias that results from their deflection, to their unbiased, non-deflected, natural, relaxed, or non-deformed state (or in other embodiments, this may be a less biased, less-deflected, or less-deformed state, as the arms 162, 163 may still be biased inwardly when in contact with the base wall 152 of the groove 151). Stated otherwise, the arms 162, 163 can resiliently return to a less bent or unbent state, as depicted by the inwardly directed arrows.

The shield 105 thus can automatically transition to the locked state, relative to the obturator 104. As previously discussed, when in the locked state, portions of the shield 105 enter into the recess 150 to secure the shield 105 to the obturator 104. When the shield 105 is locked to the obturator 104, movement of the shield 105 relative to the obturator 104 can be prevented or delimited in one or more directions or dimensions (e.g., longitudinally and/or rotationally). In some embodiments, the contact surfaces 192, 193 of the arms 162, 163 may clamp down on the base surface 152 of the recess 150 with sufficient force to prevent longitudinal and/or rotational movement of the shield 105 relative to the obturator 104. For example, an inward bias may remain after the contact surfaces 192, 193 have contacted the base surface 152, and this inward bias may give rise to a clamping force that tightly connects the shield 105 to the obturator 104. In other embodiments, the contact surfaces 192, 193 may only be brought into close proximity to or in light contact with the base surface 152 of the recess 150, which may permit the shield 105 to slide or otherwise translate and/or rotate relative to the obturator 104. In some embodiments, interference between the contact faces 194, 195 of the arms 162, 163 and the proximal and distal faces 154, 156 of the recess 150, respectively, can delimit longitudinal movement of the shield 105 relative to the obturator 104. (See also FIG. 18.)

In the illustrated embodiment, when the arms 162, 163 automatically transition to the locked state relative to the obturator 104, the arms 162, 163 substantially simultaneously decouple the shield from the needle hub 203. In particular, in the illustrated embodiment, the inward movement of the arms 162, 163 causes the outward protrusions 178, 179 to exit the groove 227 of the needle hub 203. This frees the shield 105 to move relative to the needle hub 203, such as for proximal movement in the longitudinal direction to exit the lumen 224. Stated otherwise, the contact surfaces of the arms 162, 163 and the needle hub 203 discontinue interfacing with each other to release the shield 105 from the needle hub 203.

Figure 17D:
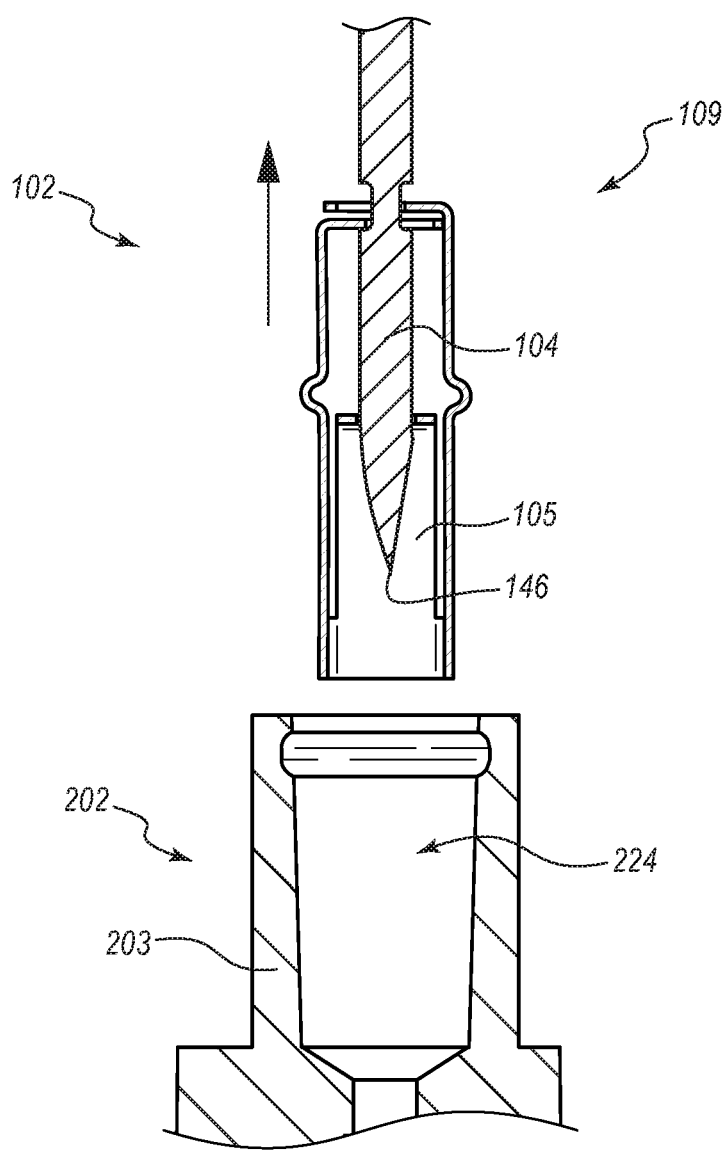
FIG. 17D is another enlarged cross-sectional view of the access assembly such as that of FIG. 17A at a subsequent stage of the illustrative method in which the obturator assembly has been fully withdrawn from the needle assembly while the shield is in the locked state relative to the obturator.

FIG. 17D is another enlarged cross-sectional view of the access assembly 109 at a subsequent stage of the illustrative method. In the illustrated stage, the obturator assembly 102 has been fully withdrawn from the needle assembly 202 and continues to be moved away from the needle assembly 202, as depicted by the upwardly directed arrow. The shield 105 naturally remains in the locked state relative to the obturator 104 and restricts access to the distal tip 146 of the obturator 104. For example, in the illustrated configuration, the arms of the shield 105 may be in a relaxed or resting state, or may continue to be inwardly biased, as previously discussed.

Figure 18:
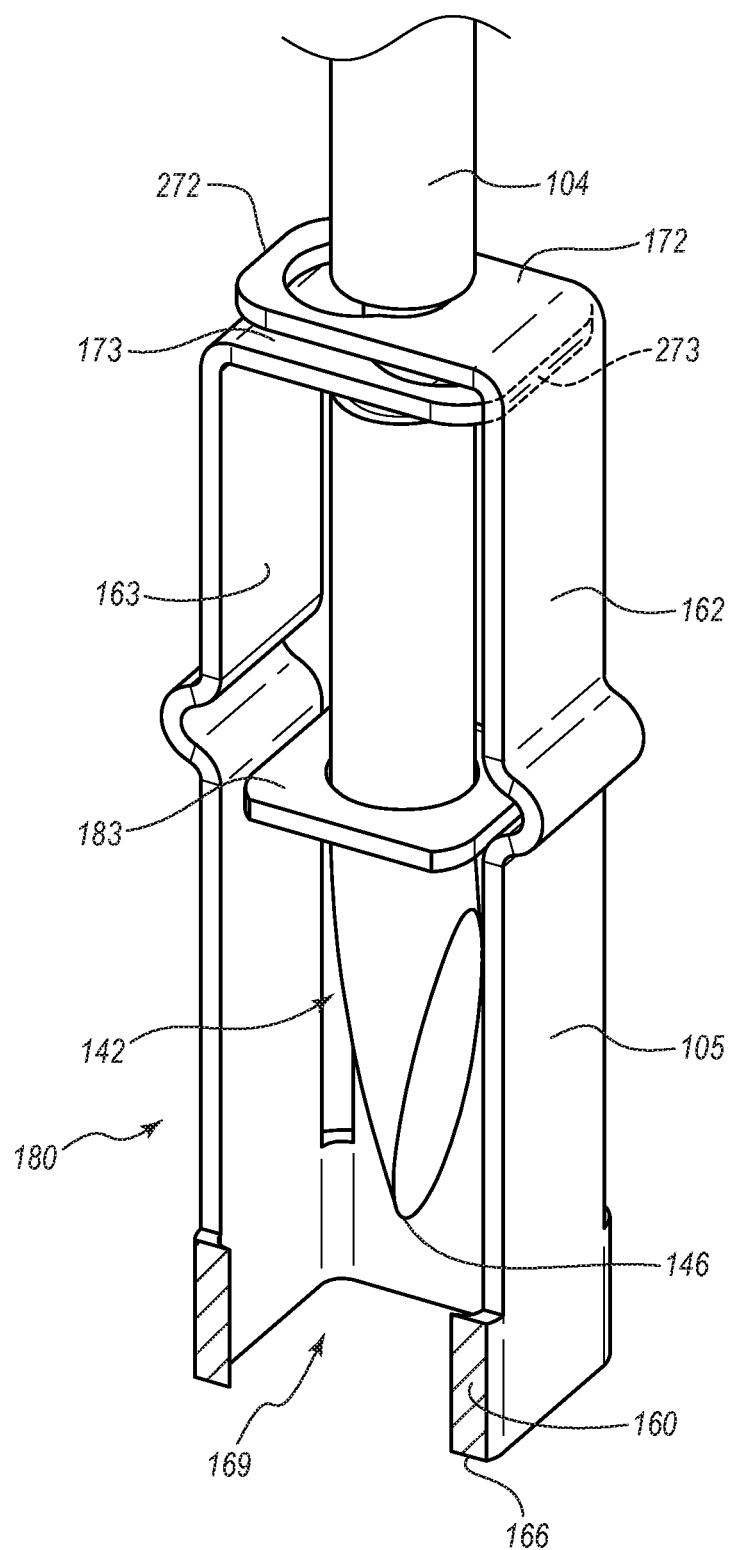
FIG. 18 is a cross-sectional perspective view of the shield attached to a distal end of the obturator after the obturator and shield have been fully removed from the needle hub.

FIG. 18 is a cross-sectional perspective view of the shield 105 attached to the distal end 142 of the obturator 104 after the obturator 104 and the shield 105 have been fully removed from the needle hub 203. As previously discussed, the shield 105 can define a cage or enclosure 180 that substantially encompasses the distal tip 146 of the obturator 104 to restrict access to the distal tip 146.

In the illustrated embodiment, the collar 160 of the shield 105 defines a fixed opening 169 at a distal end thereof. That is, a shape of the opening 169 does not change when the shield 105 transitions from the unlocked state to the locked state. In a limited sense, the distal tip 166 does not cover the distal tip 146 of the obturator 104, in that the distal tip 146 is viewable through the opening 169. Nevertheless, the shield 105 may still be said to cover the distal tip 146, as the shield 105 is capable of preventing inadvertent contact with the distal tip 146. For example, the opening 169 can be sufficiently small to prevent a practitioner or other individual from inserting any portion of skin through the opening 169 and into contact with the tip 146. In other embodiments, the opening 169 may be smaller and/or may be configured to close when the distal tip 146 is drawn into the shield 105 and/or when the shield 105 transitions to the locked state. For example, in some embodiments, a valve, elastomeric septum, or other naturally closing device may be positioned at the opening 169 of the shield such that drawing the distal tip 146 into the shield 105 results in the natural or automated closure of the opening 169.

The shield 105 may also be said to be positioned over the distal tip 146 of the obturator 104, given that the collar 160 and/or the base ends of the arms 162, 163 are positioned about the tip 146. Additionally, or alternatively, the shield 105 may be said to shroud, encompass, or encircle the tip 146.

As previously discussed, the guide 183 can stabilize the shield 105 relative to the obturator 104. The guide 183 can provide an additional point (or additional points) of contact to the obturator 104 at a position spaced distally from the proximal points of contact of the arms 162, 163. The shield 105 thus is rotationally stable, relative to the obturator 104, in that the shield 105 is inhibited or prevented from any significant rotation about any axis that extends orthogonally through a central longitudinal axis of the obturator 104.

Stated otherwise, the guide 183 can restrict or inhibit lateral movement of the shield 105 relative to the obturator 104. In other or further embodiments, the shield 105 may grip sufficiently tightly or otherwise be secured to the obturator 104 (e.g., via keying) to prevent the shield 105 from rotating about the central longitudinal axis of the obturator 104.

In some embodiments, the shield 105 includes features that inhibit or prevent inadvertent opening or outward displacement of the arms 162, 163 from the locked state to the unlocked state. For example, in the illustrated embodiment, the lateral extensions 172, 173 are in close proximity to each other and are approximately the same length. As a result, an edge 272 at an extremity, or at an end opposite the bend, of the lateral extension 172 can be substantially or approximately flush with an outer surface of the arm 163. Thus, if inadvertent contact is made in the vicinity of the edge 272, such as by inadvertent gripping, or by stepping downwardly on the outer surface of the arm 163 and the edge 272, the force is generally absorbed by the arm 163 and its contact with the obturator 104. That is, due to the close proximity of the outer surface of the arm 163 and the edge 272, the force generally is applied to the arm 163 and tends to further secure the arm 163 in the closed orientation against the obturator 104, rather than move the edge 272, the lateral extension 172, and the arm 162 laterally relative to the obturator 104 into the deflected, open, or unlocked orientation.

In a similar, and in some instances even more protective manner, the arm 162 can prevent inadvertent transitioning of the arm 163 from the locked to the unlocked configuration. In the illustrated embodiment, the arm 163 fully covers an extreme edge 273 of the lateral extension 173. Thus, the arm 163 fully shields the extreme edge 273 from contact with a laterally directed force (e.g., from inadvertent gripping of or stepping on the shield 105) that would otherwise move the edge 273, the lateral extension 173, and the arm 163 in the lateral outward direction toward the deflected, open, or unlocked state. Such force is instead intercepted by the arm 162 and directed toward the obturator 104, thus increasing a contact force between the arm 162 and the obturator 104 and more securely maintaining the arm 162 in the locked state.

Figure 19:
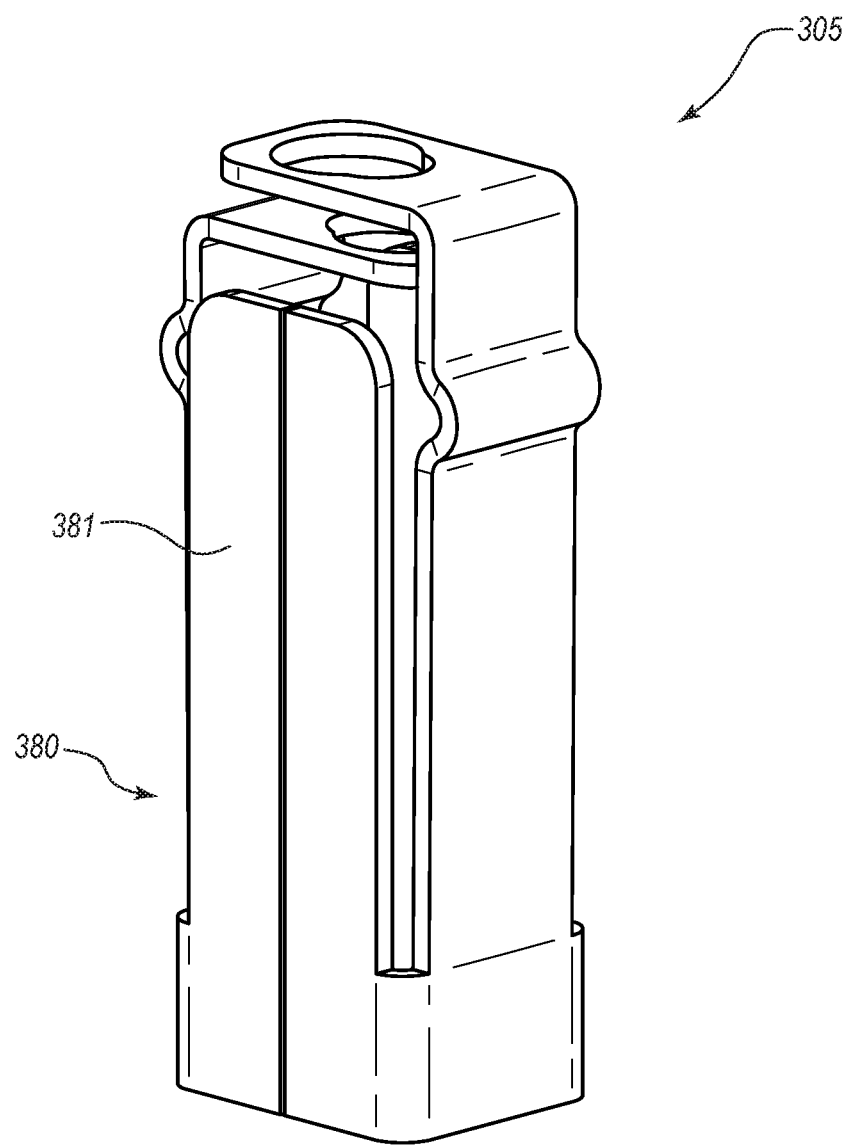
FIG. 19 is a perspective view of another embodiment of a shield that is compatible with, e.g., embodiments of intraosseous access systems disclosed herein.
Figure 20:
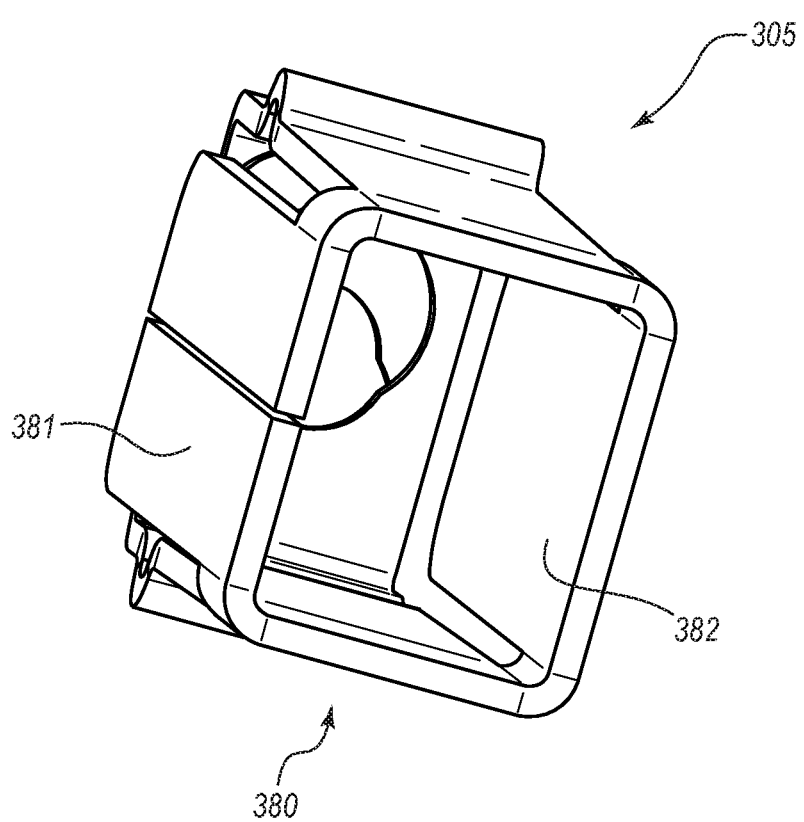
FIG. 20 is a further perspective view of the shield of FIG. 19.

FIGS. 19 and 20 are separate perspective views of another embodiment of a shield 305 that can resemble the shield 105 described above in certain respects. Accordingly, like features are designated with like reference numerals, with the leading digits incremented to "3." Relevant disclosure set forth above regarding similarly identified features thus may not be repeated hereafter. Moreover, specific features of the shield 305 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the shield 305. Any suitable combination of the features and variations of the same described with respect to the shield 105 can be employed with the shield 305, and vice versa. This pattern of disclosure applies equally to further embodiments depicted in subsequent figures and described hereafter, wherein the leading digits may be further incremented. Moreover, the shield 305 may be used with the intraosseous access system 100 or any other suitable system, such as those described elsewhere herein.

The shield 305 can differ from the shield 105 in its inclusion of an enlarged cage or enclosure 380. For example, a panel 381 can extend proximally to a greater distance than does the panel 181 described above. In some embodiments, a panel 382 likewise can extend proximally to a greater distance than does the panel 182 described above. In the illustrated embodiment, the shield 305 is devoid of a guide, such as might otherwise be formed by bending inward a proximal end of the panel 328 to form a lateral extension.

Figure 21:
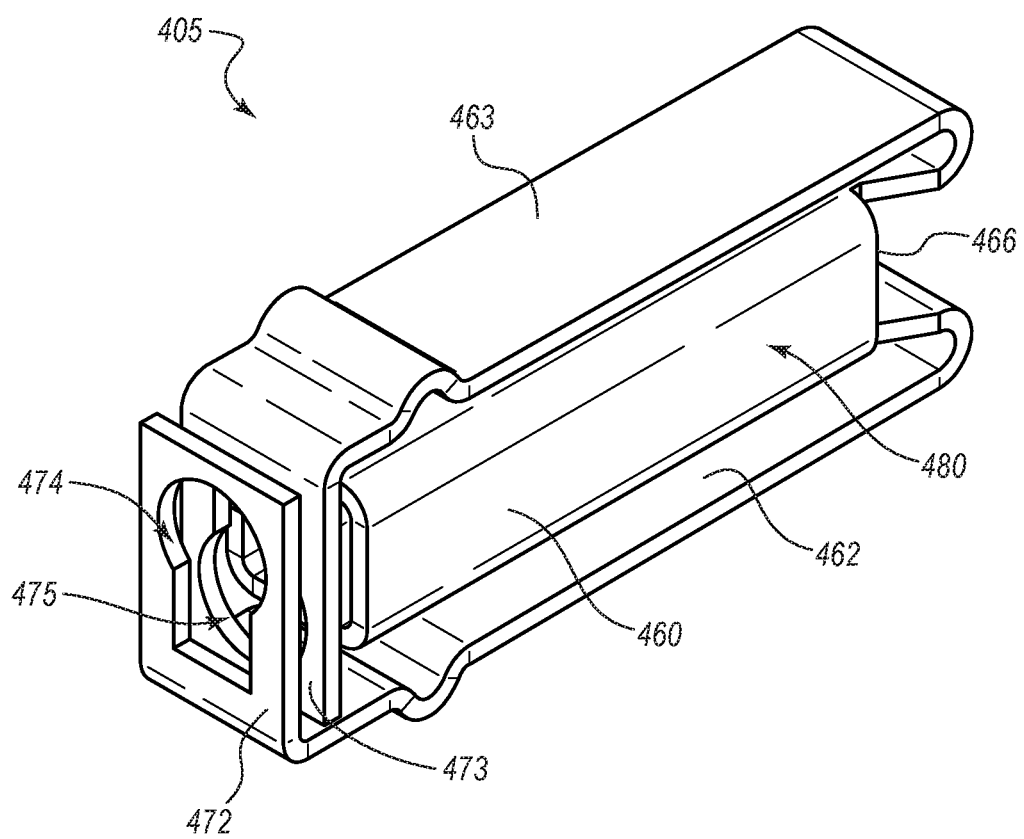
FIG. 21 is a perspective view of another embodiment of a shield that is compatible with, e.g., embodiments of intraosseous access systems disclosed herein.

FIG. 21 depicts a perspective view of another embodiment of a shield 405, which can resemble the shields 105, 305 in many respects. In the illustrated embodiment, the shield 405 includes an elongated collar 460. In particular, the collar 460 extends along greater than a majority of a full longitudinal length of the shield 405 (i.e., a distance from a proximal tip thereof to a distal tip thereof). In various embodiments, the collar 460 may extend along no less than 5, 10, 20, 30, 40, 50, or 60 percent of a full longitudinal length of the shield 405. The illustrated collar 460 is shaped substantially as an elongated tube with a rectangular cross-section, the corners thereof being rounded. Other suitable arrangements are contemplated. The collar 460 may more generally be referred to as a cage or enclosure 480. In the illustrated embodiment, the collar 460 may maintain a fixed shape, such that a size of a passageway therethrough remains substantially constant when the shield 405 transitions from the unlocked state to the locked state.

In the illustrated embodiments, the shield 405 includes arms 462, 463 that extend distally from a distal tip, distal face, or distal edge 466 of the collar 460. Each arm 462, 463 includes a bend of at least 140, 150, 160, 170, or 180 degrees, such that a significant length thereof extends substantially parallel to an outer surface of the collar 460 in the distal-to-proximal direction. Accordingly, a proximal portion of each arm 462, 463 extends proximally away from the distal edge 466 of the collar 460. Each arm 462, 463 can include a lateral extension 472, 473, respectively, that extends over a proximal opening of the collar 460.

Figure 22:
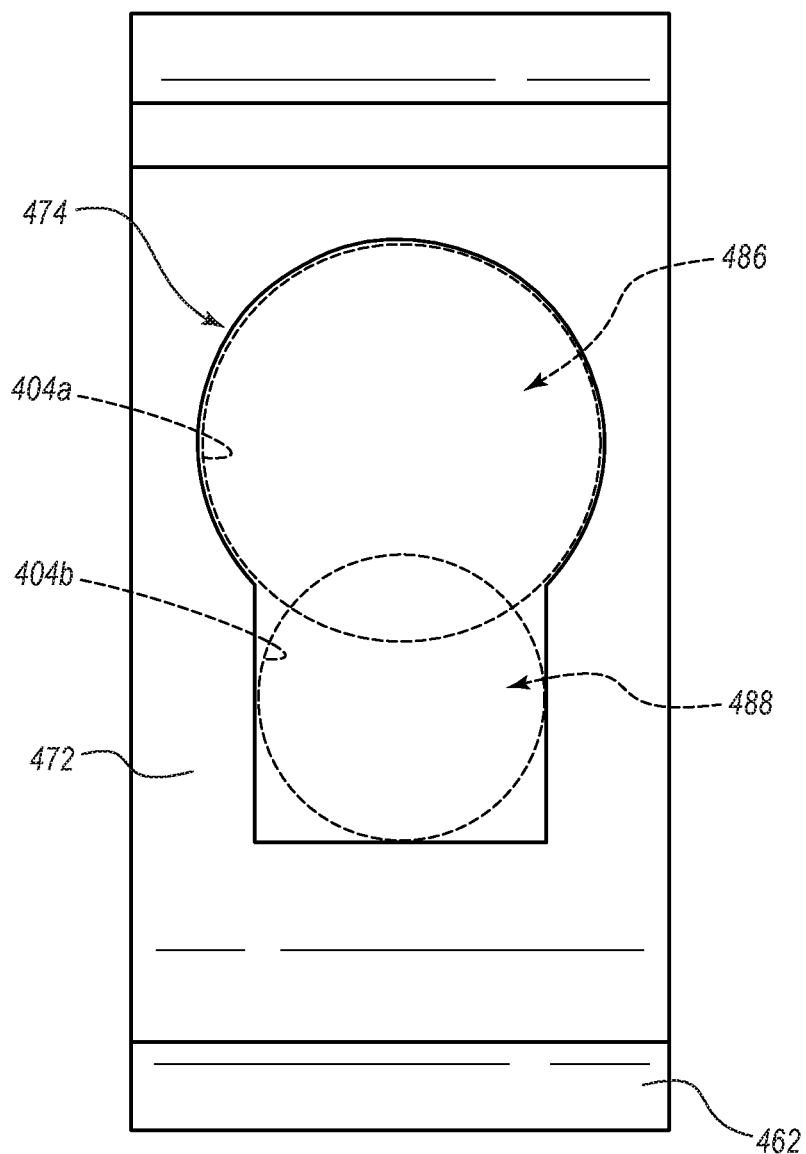
FIG. 22 is a top plan view of the shield of FIG. 21.

With reference to FIGS. 21 and 22, the lateral extensions 472, 473 can each define openings 474, 475, respectively, through which an obturator can extend. The openings 474, 475 may be shaped substantially identically and oriented in opposite directions.

As shown in greater detail in FIG. 22, the opening 474 can be shaped substantially as a keyhole. The keyhole shape can include a first region that includes a semi-circular border and defines a first diameter, and can further include a second region that includes a rectangular border and defines a second diameter that is smaller than the first diameter. As with the opening 174 discussed above, the opening 474 can include a passageway 486 and a constriction 488. An outer surface 404a of a proximal portion of an illustrative obturator is depicted in broken lines within the passageway 486, and an outer surface 404b of a recessed portion of the obturator is depicted in broken lines within the constriction 488. As with the obturator 104 discussed above, the outer surface 404a of the proximal portion of the obturator can maintain the arm 462 in an unlocked state when positioned within the passageway 486 of the opening 474, and when the recessed portion 404b of the obturator is brought within the opening 474, the arm 462 can naturally transition to the locked state as at least a portion of the recessed region of the obturator enters into the constriction 488.

Figure 23:
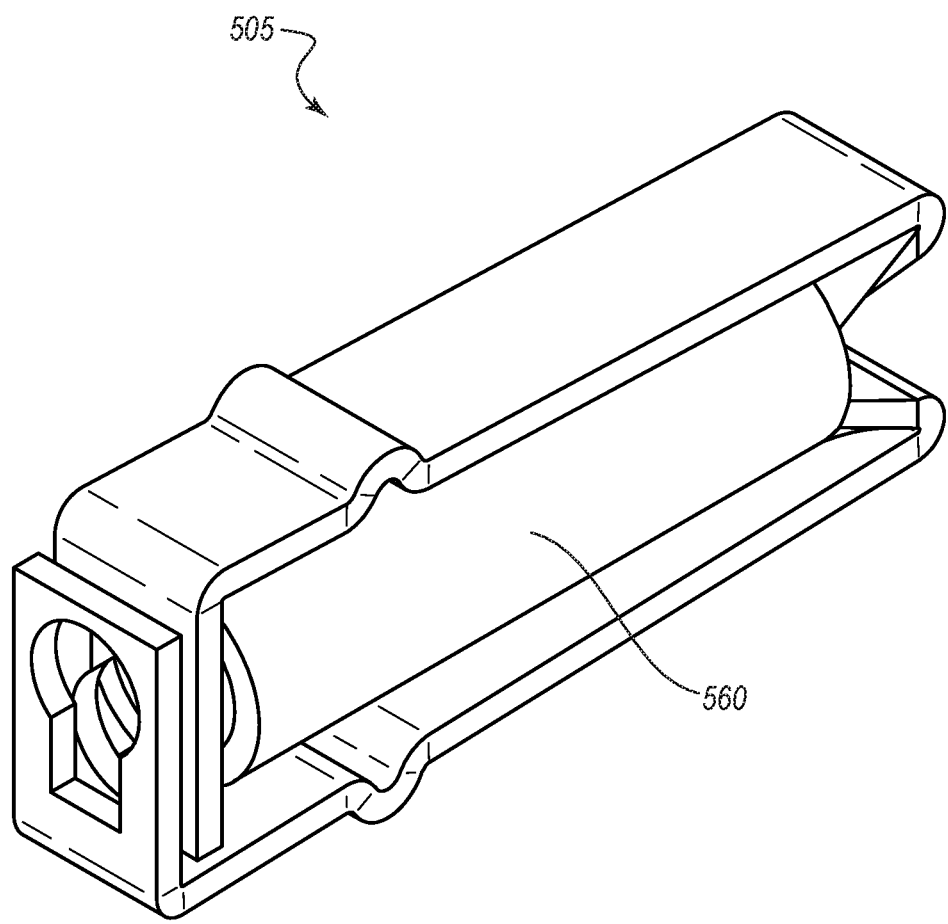
FIG. 23 is a perspective view of another embodiment of a shield that is compatible with, e.g., embodiments of intraosseous access systems disclosed herein.

FIG. 23 depicts a perspective view of another embodiment of a shield 505, which can resemble the shields 105, 305, 405 in many respects. In the illustrated embodiment, the shield 505 includes an elongated collar 560 similar to the collar 460. The illustrated collar 560 is shaped substantially as an elongated tube with an oval or circular cross-section. Other suitable arrangements are contemplated.

Figure 24:
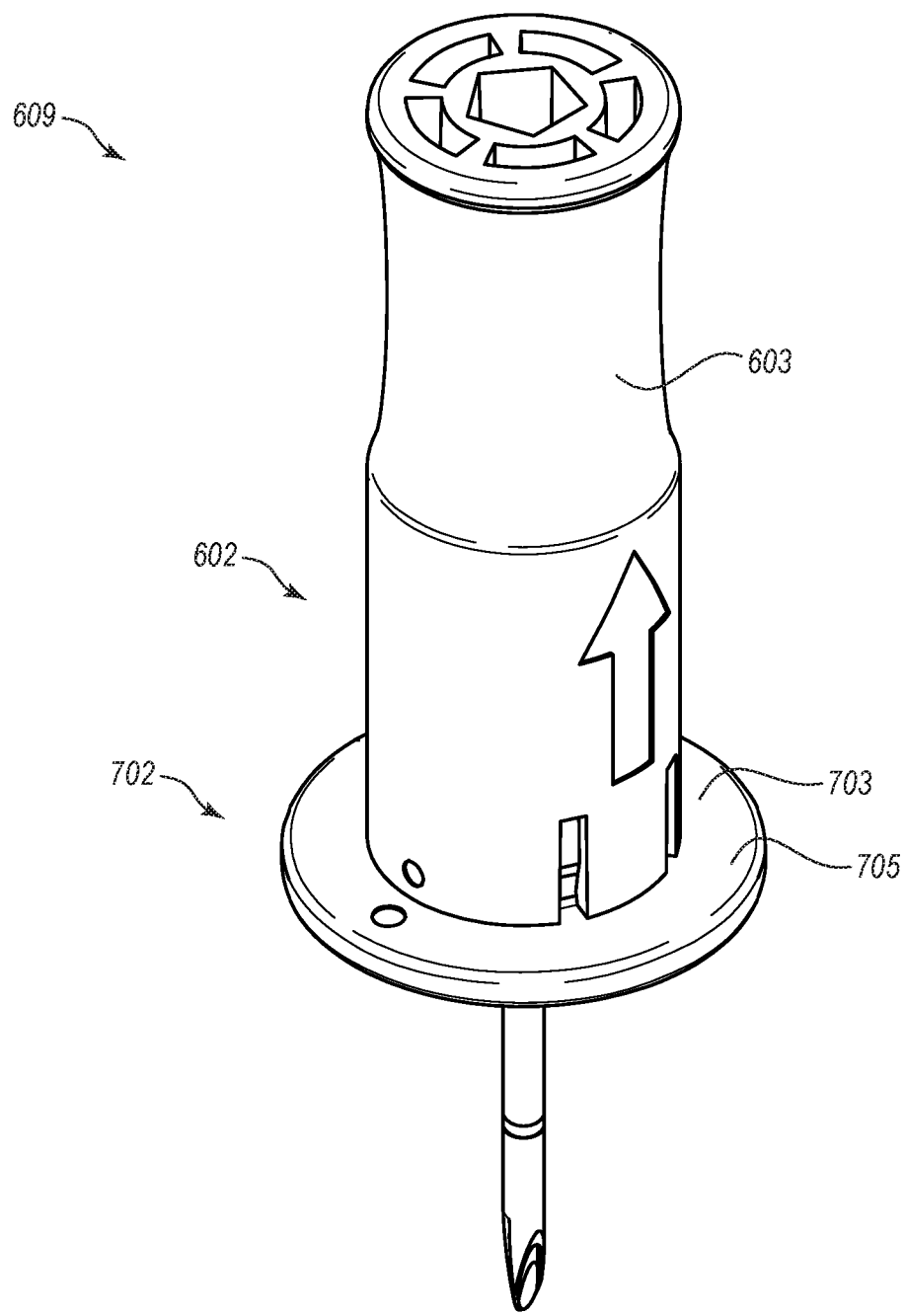
FIG. 24 is a perspective view of another embodiment of an access assembly.

FIG. 24 is a perspective view of another embodiment of an access assembly 609 that includes an obturator assembly 602 and a needle assembly 702, which are depicted in a coupled state. The needle assembly 702 includes a needle hub 703 that further includes an outwardly extending flange 705. In the illustrated embodiment, the flange 705 extends outwardly beyond a maximum lateral perimeter of an obturator hub 603 of the obturator assembly 602. Stated otherwise, the needle hub 703 defines a higher profile, relative to a central longitudinal axis of the access assembly 609, than does the obturator hub 603. By comparison, with reference again to FIG. 15, the needle hub 203 defines a lower profile, relative to a central longitudinal axis of the access system 109, than does the obturator hub 103.

Figure 25:
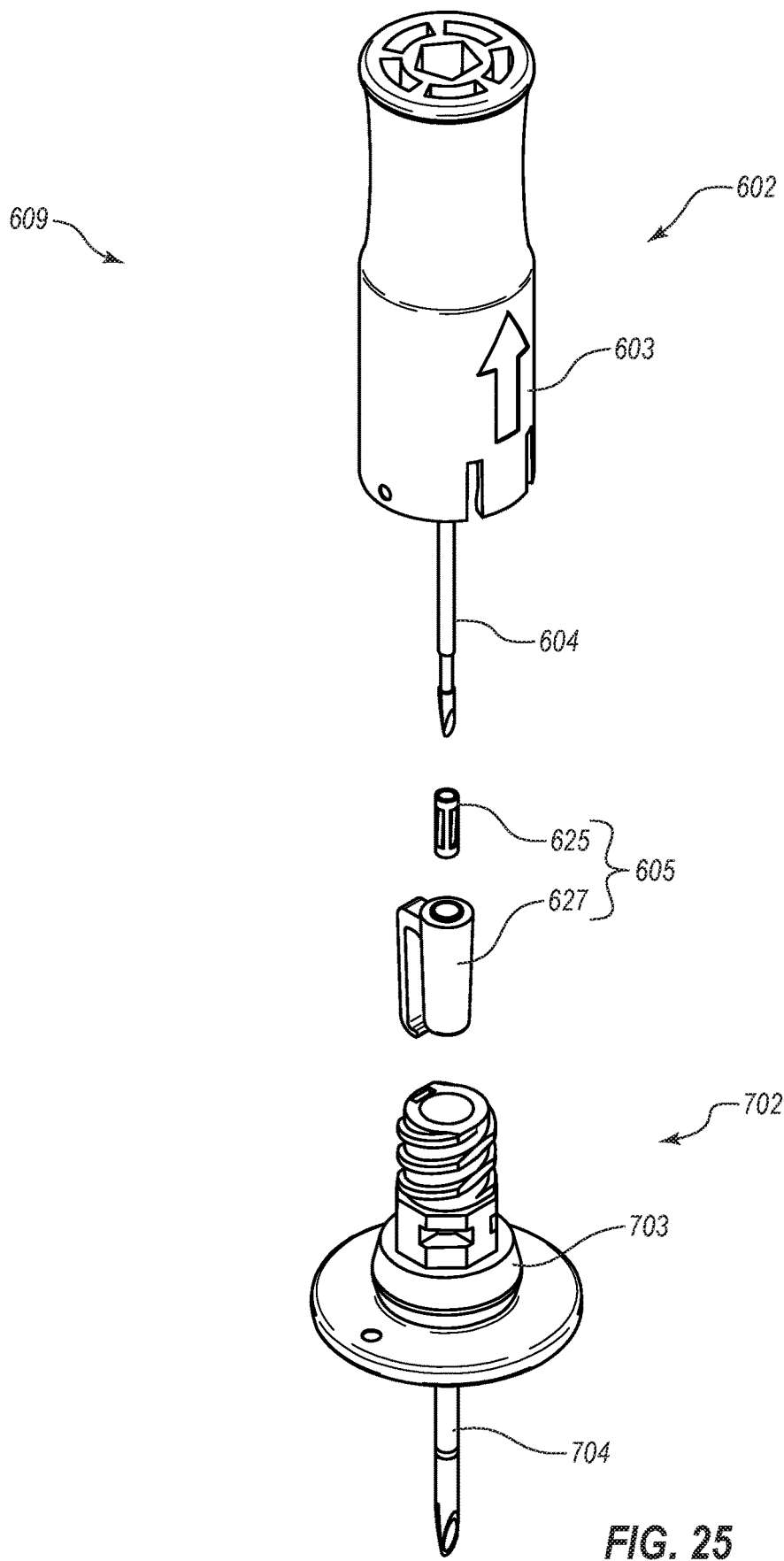
FIG. 25 is an exploded elevation view of the access assembly of FIG. 24.

With reference to FIGS. 25, the obturator assembly 602 includes the obturator hub 603 permanently coupled to an obturator 604. As with other embodiments discussed herein, the obturator 604 may more generally be referred to as an elongated medical instrument. Moreover, in other embodiments, different elongated medical instruments may be used in an access assembly, such as, for example, a trocar, stiffener, stylet, needle, etc.

The access assembly 609 further includes a safety shield 605, which can be a multi-component device. In the illustrated embodiment, the shield 605 includes a catch 625 and a housing 627, which are described further below.

With continued reference to FIG. 25, the needle assembly 702 can include the needle hub 703 permanently coupled to a needle 704. As with other embodiments discussed herein, the needle 704 may be more generally referred to as a sheath or cannula. Moreover, in other embodiments, different tubular, sheath-like, or otherwise externally positioned devices may be used.

Figure 26:
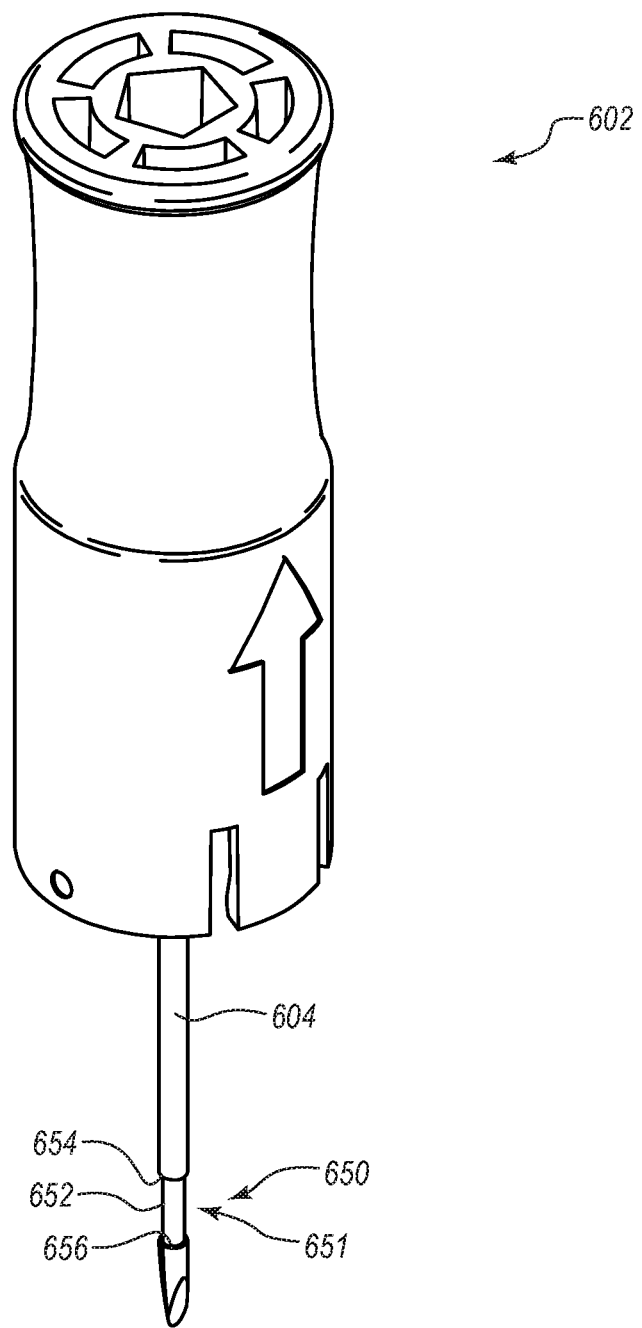
FIG. 26 is a perspective view of an obturator assembly portion of the access assembly of FIG. 24.

With reference to FIG. 26, the obturator 604 can include a recessed region 650, such as a groove 651 that includes a base wall 652, a proximal wall 654, and a distal wall 656. In some embodiments, the proximal wall 654 and the distal wall 656 may be spaced relatively further apart from each other, as compared with the proximal and distal walls 154, 156 discussed above. The obturator 604 may otherwise resemble the obturator 104.

Figure 28B:
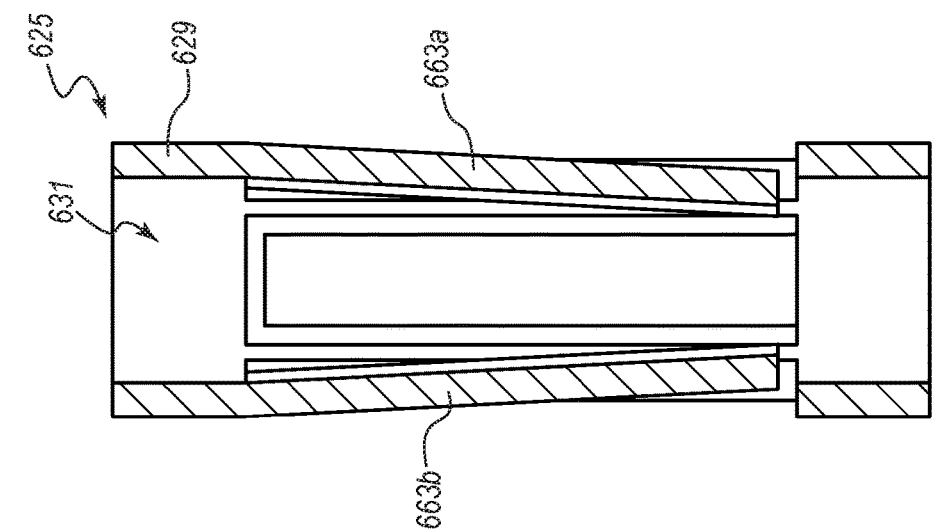
FIG. 28B is a cross-sectional view of the catch taken along the view line 28B in FIG. 27.
Figure 28A:
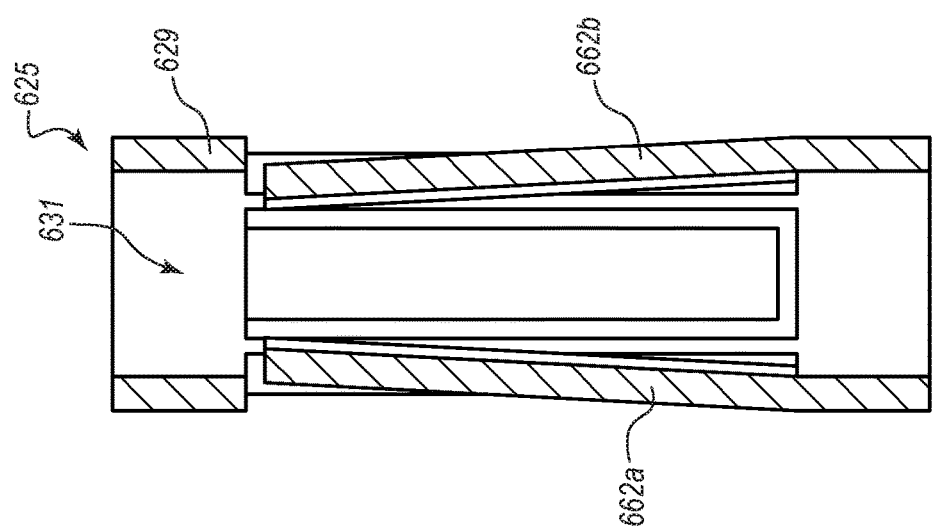
FIG. 28A is a cross-sectional view of the catch portion of the access assembly of FIG. 24 taken along the view line 28A in FIG. 27.
Figure 27:
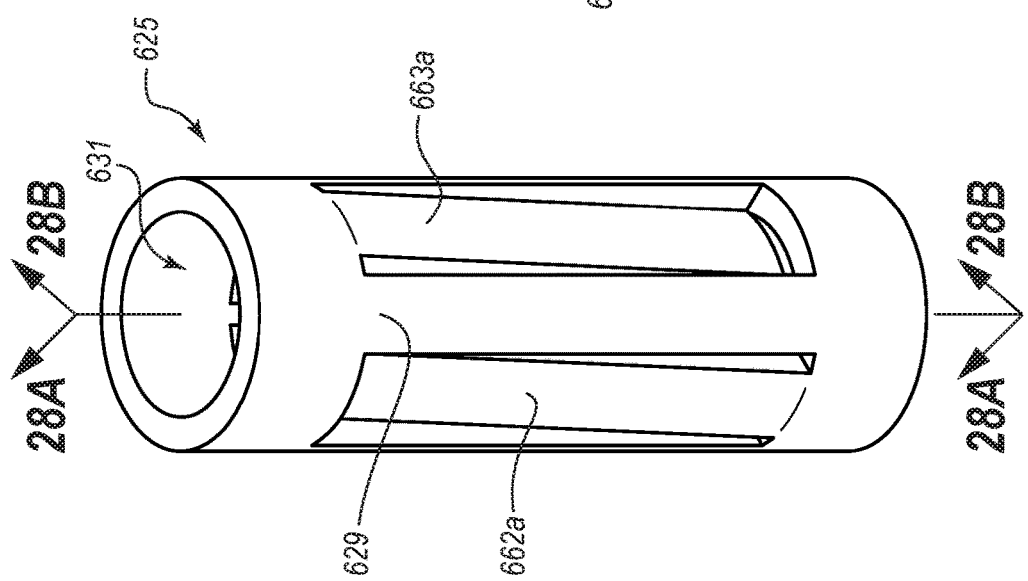
FIG. 27 is a perspective view of a catch portion of a shield.

FIGS. 27, 28A, and 28B depict the catch 625 in further detail. The catch 625 may also or alternatively be referred to as a spring, clip, latch, fastener, etc. In the illustrated embodiment, the catch 625 includes a body 629 from which a plurality of extensions or arms 662a, 662b, 663a, 663b extend inwardly. The body 629 can be substantially cylindrical, as shown, or can define any other suitable shape. The catch 625 can define a lumen 631 into which the obturator 604 can be received.

In the illustrated embodiment, two resiliently flexible arms 662a, 662b extend inwardly in the proximal direction. The arms 662a, 662b are at opposite sides of the body 629. Two additional resiliently flexible arms 663a, 663b extend inwardly in the distal direction, and are at opposite sides of the body 629. The arms 662a, 662b, 663a, 663b all extend inwardly in a natural, resting, non-deflected, or locking state. The arms 662a, 662b, 663a, 663b can be deflected outwardly, such as substantially into alignment with an outer surface of the body 629, or stated otherwise, such that outer surfaces thereof correspond to a cylindrical surface substantially defined by the body 629, to define an open or unlocked state. When the catch 625 is in the unlocked state, the lumen 631 can be sufficiently large to accept therein a proximal portion of the obturator 604. The outer surface of the proximal end of the obturator 604 can maintain the arms 662a, 662b, 663a, 663b in the outwardly deflected state against an internal bias (e.g., a continuous bias, when the arms are in the deflected orientation) that tends to urge the arms 662a, 662b, 663a, 663b inward. As further discussed below, the arms 662a, 662b, 663a, 663b can automatically spring inwardly to lock the catch 629 in a substantially fixed longitudinal position relative to the obturator 604 when the recessed portion of the obturator 604 is pulled into the lumen 631.

Figure 30:
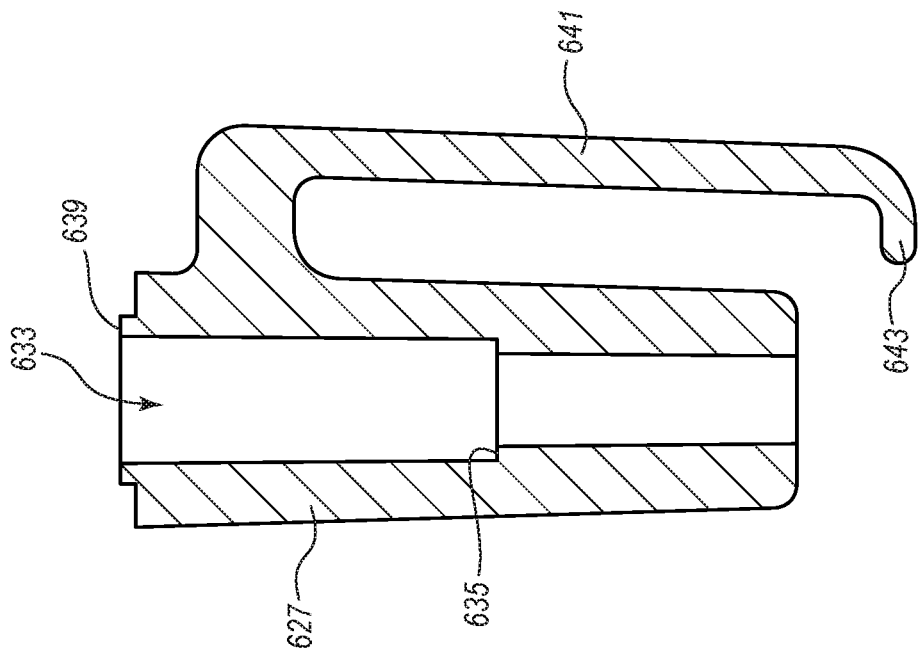
FIG. 30 is a cross-sectional view of the housing taken along the view line 30-30 in FIG. 29.
Figure 29:
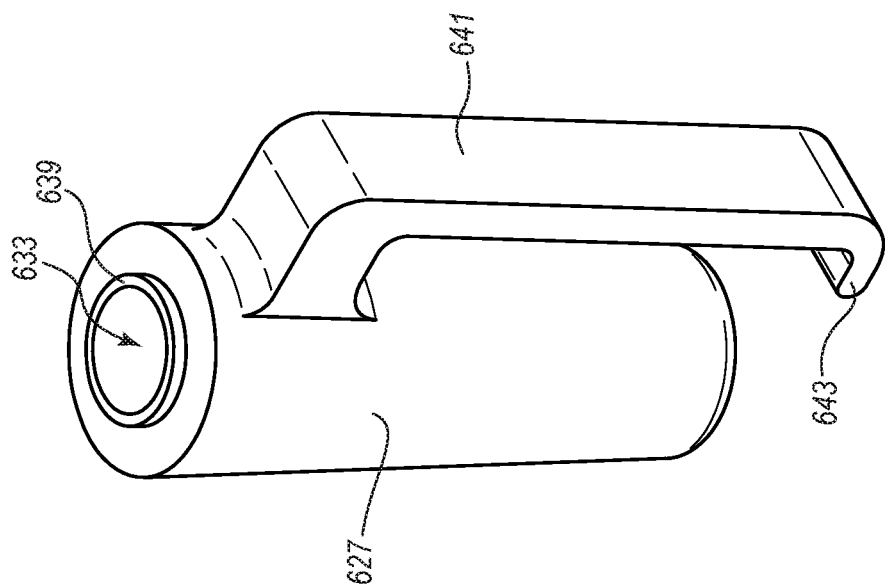
FIG. 29 is a perspective view of a housing portion of the shield into which the catch is received.

FIGS. 29 and 30 depict perspective and cross-sectional views, respectively, of the housing 627. In the illustrated embodiment, the housing 627 defines a lumen 633 into which the catch 625 is received and retained. In particular, the lumen 633 includes a larger proximal portion into which the catch 625 can fit (e.g., fit snugly), and can include a narrower distal portion through which the obturator 604 can pass. The housing 627 may define a shoulder 635 against which a distal end of the catch 625 can rest.

In some embodiments, the housing 627 can include a lip 639 that can be reconfigured to maintain the catch 625 within the lumen 633. For example, in some embodiments, the housing 627 is formed of a polymeric material. After the catch 625 is inserted into the lumen 633, the lip 639 can be melted and deformed or otherwise reconfigured to trap the catch 625 and secure it within the housing 627 (see FIGS. 32A-32E).

The housing 627 can include an extension or arm 641, which may be resiliently deformable. In the illustrated embodiment, the arm 641 extends distally from a proximal end of the housing 627. The arm 641 includes an inward protrusion 643 at a distal end thereof. As further discussed below, the arm 641 can selectively couple the shield 605 to the needle hub 703.

Figure 31:
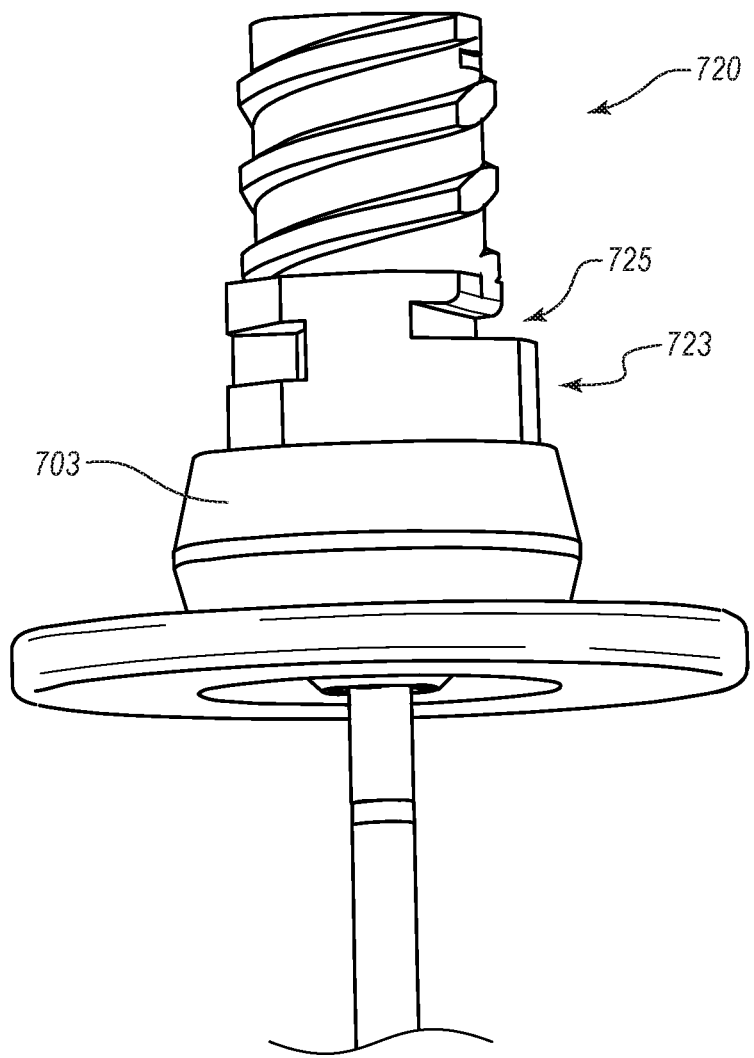
FIG. 31 is a perspective view of a proximal portion of a needle assembly portion of the access assembly of FIG. 24.

With reference to FIG. 31, the needle hub 703 can include a connector 720, which can resemble the connector 120 discussed above. The needle hub 703 can further include a shaft 723, such as the shaft 123 discussed above. The shaft 723 can define an inwardly projecting recess 725. In the illustrated embodiment, the recess 725 is positioned distally from a distal end of the connector 720. In the illustrated embodiment, the recess 725 is defined by an external surface of the needle hub 703.

Figure 32A:
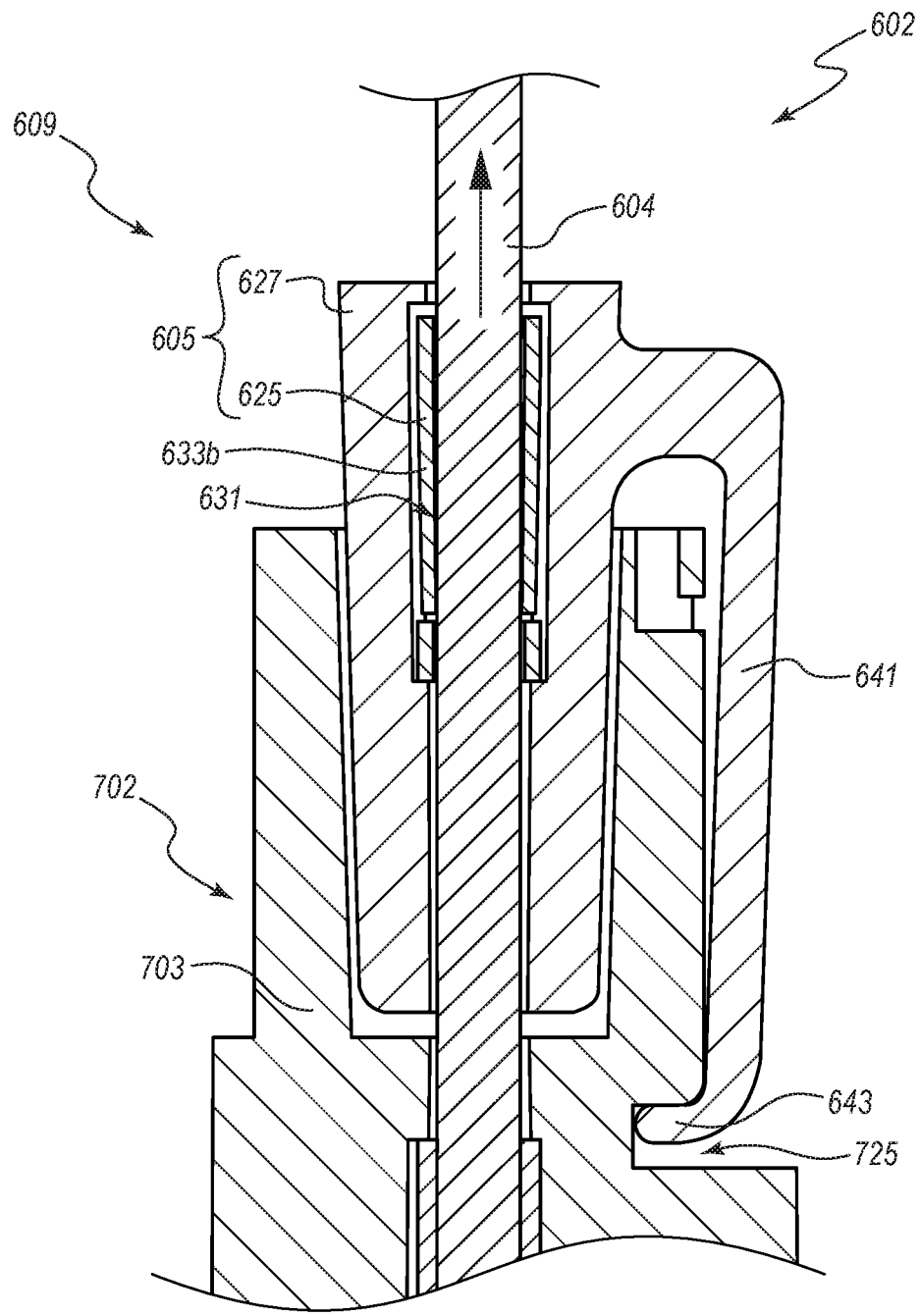
FIG. 32A is an enlarged cross-sectional view of the access assembly if FIG. 24, with an obturator hub portion thereof not being shown for purposes of clarity, at a stage of an illustrative method in which the obturator assembly is being decoupled and withdrawn from the needle assembly while the shield is in an unlocked state relative to an obturator, and is in a coupling state relative to a needle hub.

FIG. 32A is an enlarged cross-sectional view of the access assembly 609 at a stage within an illustrative method of use. In FIG. 32A, the obturator hub 603 is not shown for purposes of clarity, although the obturator hub 603 would be present in the present view. The depicted stage is similar to that of FIG. 17A, which is discussed above. In the illustrated stage, the obturator assembly 602 is being decoupled and withdrawn from the needle assembly 702, as depicted by the upwardly directed arrow.

Prior to and during the illustrated stage, the shield 605 is coupled to the needle hub 703 via the arm 641. In particular, the inward protrusion 643 of the arm 641 is received within the recess 725 and thereby engages the needle hub 703. Stated otherwise, the arm 641 grips an outer surface of the needle hub 703. The strength of the engagement or grip can be sufficient to resist proximal movement of the shield 605 as the obturator 604 slides proximally relative to the catch 625. Stated otherwise, the inwardly biased arms 663a, 663b (and the inwardly biased arms 662a, 662b, as shown in FIG. 32C) can press inwardly against an outer surface of the obturator 604 as the obturator 604 is withdrawn in the proximal direction. The frictional forces thus generated, which urge the shield 605 proximally, can be counteracted by the engagement force of the arm 641 to the needle hub 703. Accordingly, in various embodiments, an engagement force provided by the resiliently flexible arm 641 of the housing 627 can exceed each of a static frictional force (e.g., a frictional force present prior to withdrawal of the obturator 604) and a sliding or kinetic frictional force (e.g., a frictional force present during withdrawal) between the catch 625 (e.g., between the respective ends of the inwardly biased arms 662a, 662b, 663a, 663b of the catch 625) and the outer surface of a proximal end of the obturator 604. This engagement force thus can maintain the shield 605 coupled to the needle hub 703 during withdrawal of the proximal end of the obturator 604.

The proximal end of the obturator 604 can maintain the shield 605, and in particular, the inwardly biased arms 662a, 662b, 663a, 663b of the catch 625, in the unlocked state. The shield 605 can permit proximal movement of the obturator 604 relative thereto when in the unlocked state.

In view of the foregoing, in the illustrated embodiment, different arm portions of the shield 605 determine whether the shield 605 is in the unlocked or locked state relative to the obturator 604 and whether the shield 605 is in a coupled or decoupled state relative to the needle hub 702. Moreover, in the illustrated embodiment, the different arm portions operate independently of each other. As discussed further below, in some embodiments, the shield 605 can be transitioned from the unlocked state to the locked state relative to the obturator 604 at a different time (e.g., earlier) or at a different operational stage than that at which the shield 605 is transitioned from the coupled state to the decoupled state, relative to the needle hub 703.

Figure 32B:
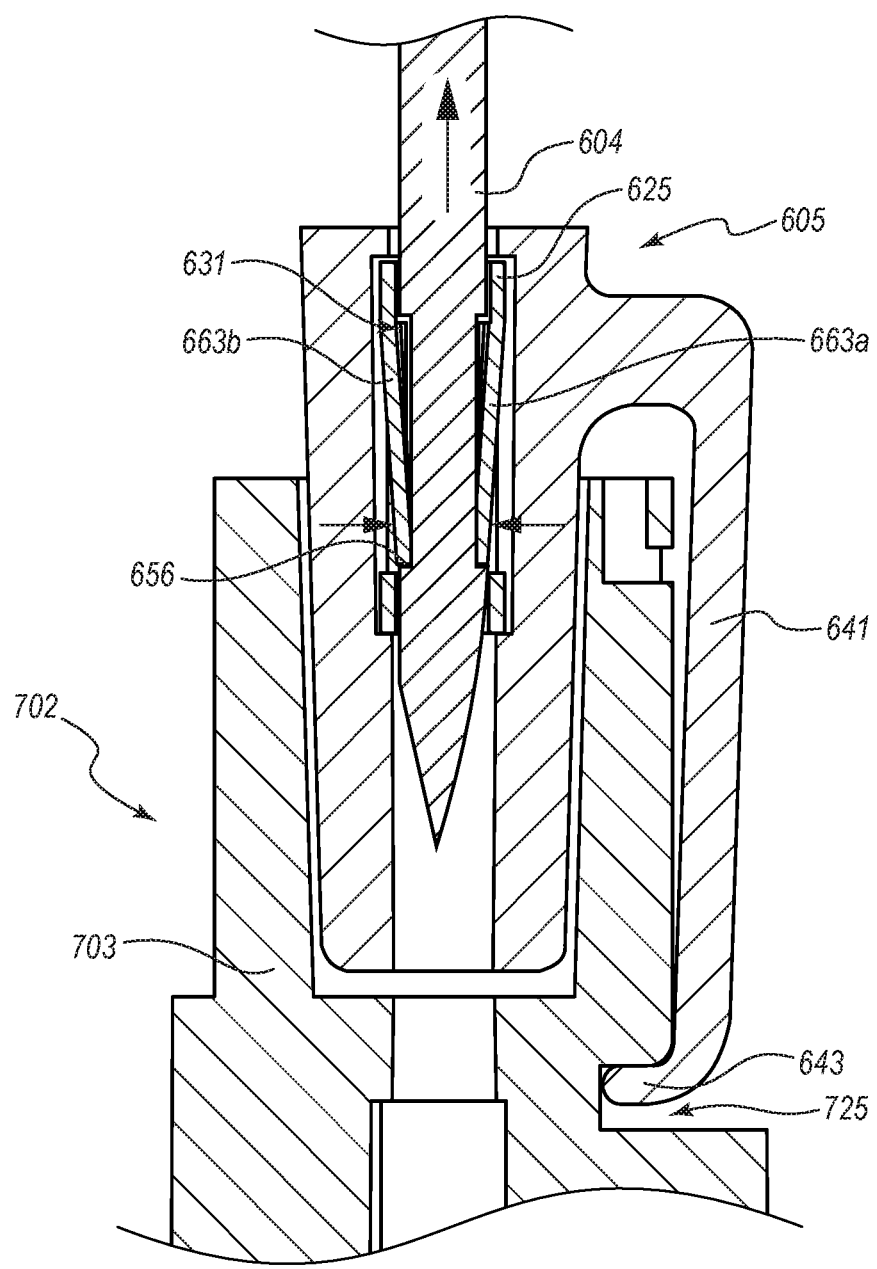
FIG. 32B is another enlarged cross-sectional view of the access assembly at a subsequent stage of the illustrative method in which the obturator assembly is being further withdrawn from the needle assembly and in which the shield transitions from the unlocked state to a locked state relative to the obturator while remaining in the coupling state relative to the needle hub.
Figure 32C:
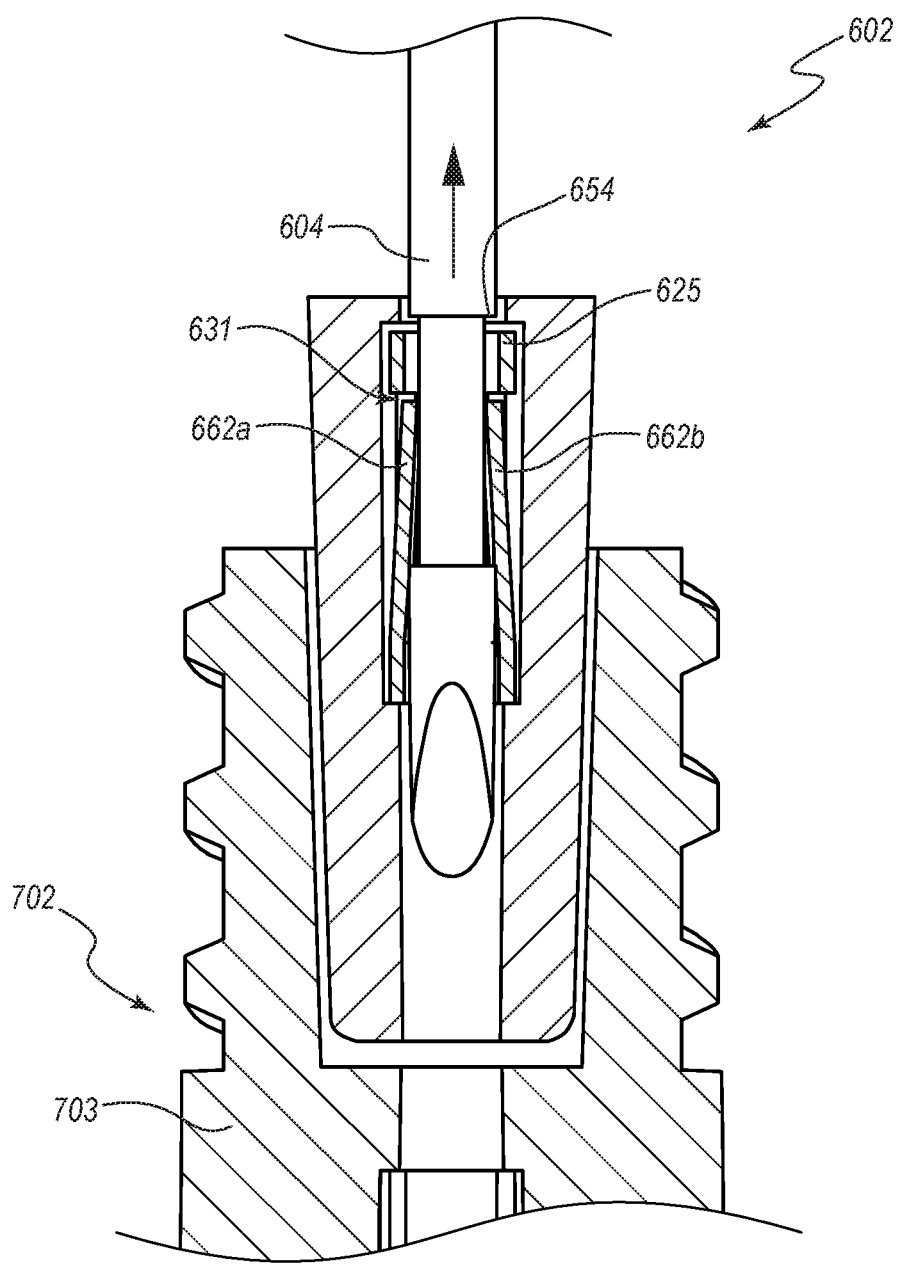
FIG. 32C is an enlarged cross-sectional view of the access assembly at the same stage of the illustrative method depicted in FIG. 32B, taken along a view line that is rotated 90 degrees relative to the view line of FIG. 32B.

FIGS. 32B and 32C depict a subsequent stage of the illustrative method. The cross-sectional views depicted in these drawings are taken through planes that are orthogonal to each other. FIG. 32B shows movement of the inwardly biased arms 663a, 663b to a locked configuration. FIG. 32C shows the inwardly biased arms 662a, 662b of the catch 625 in a locked configuration that was achieved prior to the time depicted in this drawing.

In the depicted stage of the illustrative method, the obturator 604 has been moved proximally relative to the needle hub 703 by a further amount than it has in FIG. 32A. In particular, the obturator 604 has been moved proximally by a sufficient amount to draw the recess 650 fully into the lumen 631 of the catch 625. As shown in FIG. 32B, the distally directed arms 663a, 663b spring inwardly into the recess 650 of the obturator 604, and can thereafter inhibit proximal movement of the shield 605 relative to the obturator 604 due to interference or abutment between the distal faces of the arms 663a, 663b and the distal face 656 of the recess 650. The arms 663a, 663b may be said to transition in this manner to a locked state relative to the obturator 604.

With continued reference to FIGS. 32B and 32C, movement of the arms 663a, 663b to the locked state may likewise transition the shield 605 to a fully locked state relative to the obturator 604, which can prevent or inhibit both proximal and distal movement of the shield 605 relative to the obturator 604. For example, as can be appreciated from FIG. 32C, the shield 605 may in some instances be transitioned to a partially locked state, prior to being transitioned to the fully locked state, when the proximally directed arms 662a, 662b initially spring inwardly into the recess 650. This inward movement can thereafter prevent or inhibit the shield 605 from being moved proximally relative to the obturator 604, due to interference or abutment between the proximal tips of the arms 662a, 662b and the proximal face 654 of the recess 650. Although the arms 662a, 662b transition to a locked stage during this earlier phase, the arms 663a, 663b remain in the outwardly deflected unlocked orientation (e.g., in the position depicted in FIG. 32A). When in the partially locked orientation (which may also be referred to as a partially unlocked orientation), the outwardly deflected arms 663a, 663b can permit the shield 605 to move distally relative to the obturator 604. Stated otherwise, the arms 663a, 663b can permit the obturator 604 to continue to be withdrawn proximally relative to the shield 605 when the shield 605 is in the partially locked state.

With reference again to FIG. 32B, after the shield 605 has been transitioned to the locked state relative to the obturator 604, the shield 605 may continue to remain in a coupled state relative to the needle hub 703. In particular, in order to disengage the protrusion 643 of the arm 641 from the recess 725, a user may be required to apply a greater amount of force to the obturator 604 in a proximal direction than was previously applied in withdrawing the recess 650 of the obturator 604 into the shield 605. Stated otherwise, in some embodiments, a first amount of force may be required to withdraw the obturator 604 proximally in order to transition the shield 605 from the unlocked state to the locked state relative to the obturator 604, and a second amount of force that is greater than the first amount of force may be required to thereafter transition the shield 605 from a coupled state to a decoupled state relative to the needle hub 703.

Figure 32D:
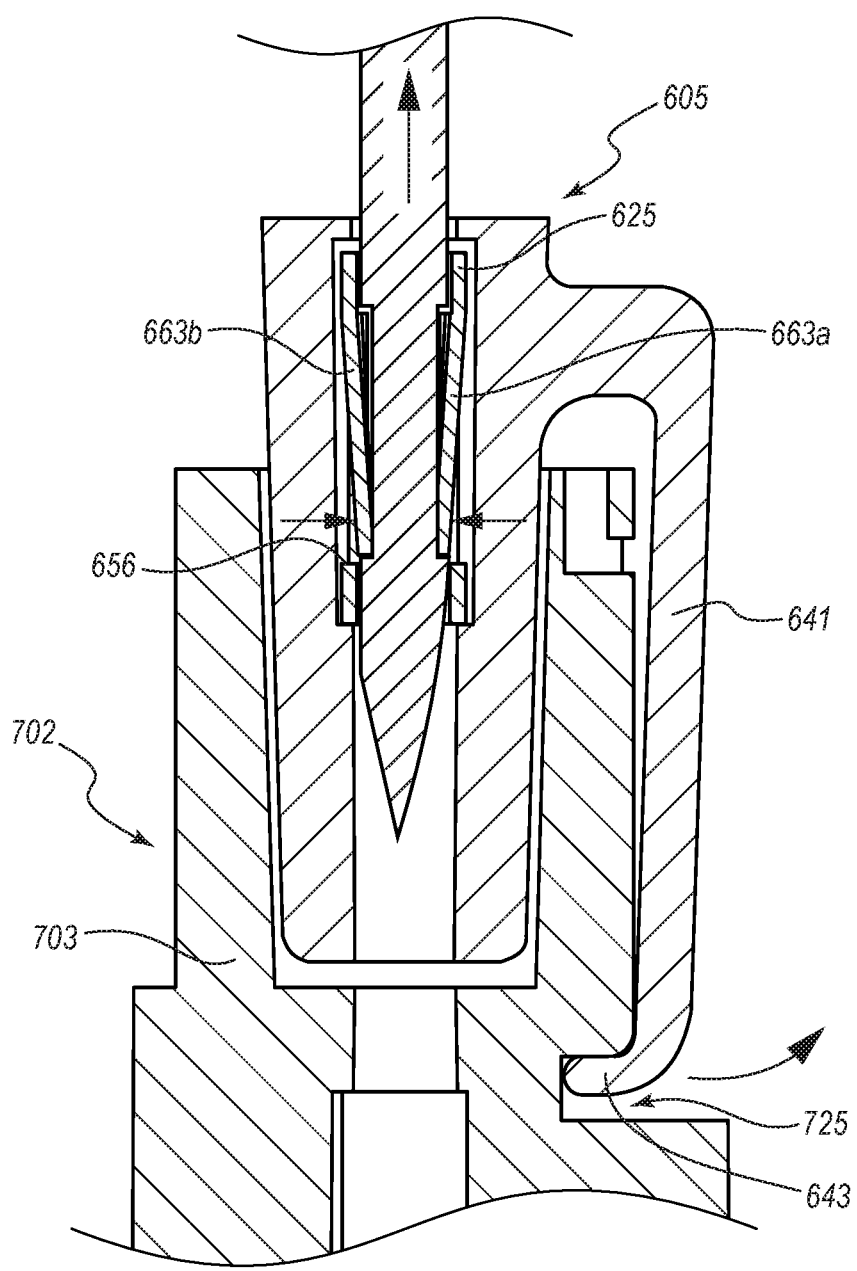
FIG. 32D is another enlarged cross-sectional view of the access assembly, such as that depicted in FIG. 32B, in which the obturator assembly is further withdrawn from the needle assembly while the shield remains in the locked state relative to the obturator and in which the shield transitions from the coupling state to a decoupling state relative to the needle hub.

FIG. 32D depicts a later stage than that of FIGS. 32B and 32C in which a greater amount of proximally directed force is applied to the obturator 604 to decouple the shield 605 from the needle hub 703. In the illustrated embodiment, after the shield 605 has been transitioned to the fully locked state relative to the obturator 604 (as depicted in FIGS. 32B and 32C), the distal face 656 of the recess 650 can press upwardly on the distal tips of the arms 663a, 663b, thus urging the shield 605 upwardly. This further application of force can cause the arm 641 to deflect outwardly and release from the needle hub 703, thereby permitting the shield 605 to be withdrawn from the needle hub 703. In some embodiments, the amount of force required to decouple the shield 605 from the needle hub 703 in this manner can be less than an amount of force required to extract the needle 704 (see FIG. 25) from a bone into which it has been introduced. For example, in some embodiments, a user can fully withdraw the shield 605 from the needle hub 703 without providing any counterforce on the needle hub 703 in the distal direction. Stated otherwise, in some embodiments, the user can withdraw the shield from the needle hub 703 one-handedly, or by pulling on or otherwise contacting only the obturator hub 603 (see FIGS. 24 and 25). In other embodiments, a user may grip the needle hub 703 with one hand while removing the obturator hub 603 with the other.

Figure 32E:
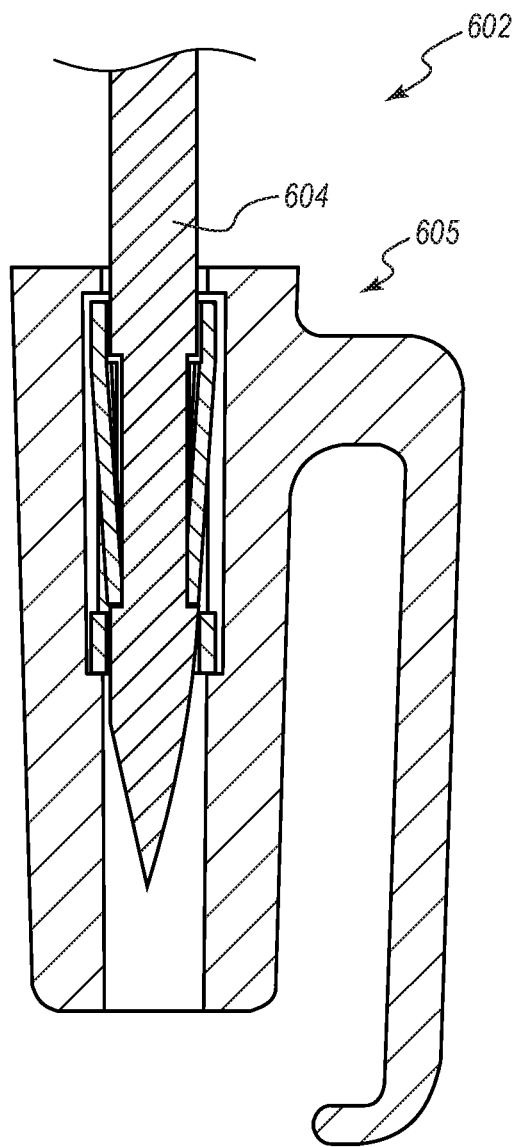
FIG. 32E is another enlarged cross-sectional view of the access assembly such as that of FIG. 32B at a subsequent stage of the illustrative method in which the obturator assembly has been fully withdrawn from the needle assembly while the shield is in the locked state relative to the obturator.

FIG. 32E is another enlarged cross-sectional view of a portion of the access assembly 609 that depicts a subsequent stage of the illustrative method. In this stage, the obturator assembly 602 has been fully withdrawn from the needle assembly 703 while the shield remains in the locked state relative to the obturator 604. The shield 605 inhibits or prevents inadvertent contact with the distal tip of the obturator 604. In some embodiments, translational movement of the shield 605 relative to the obturator 604 is delimited or prevented in the manners discussed above. In further embodiments, rotational (e.g., about a longitudinal axis) of the shield 605 relative to the obturator 604 is delimited or prevented, such as in manners discussed above with respect to other embodiments.

Figure 33:
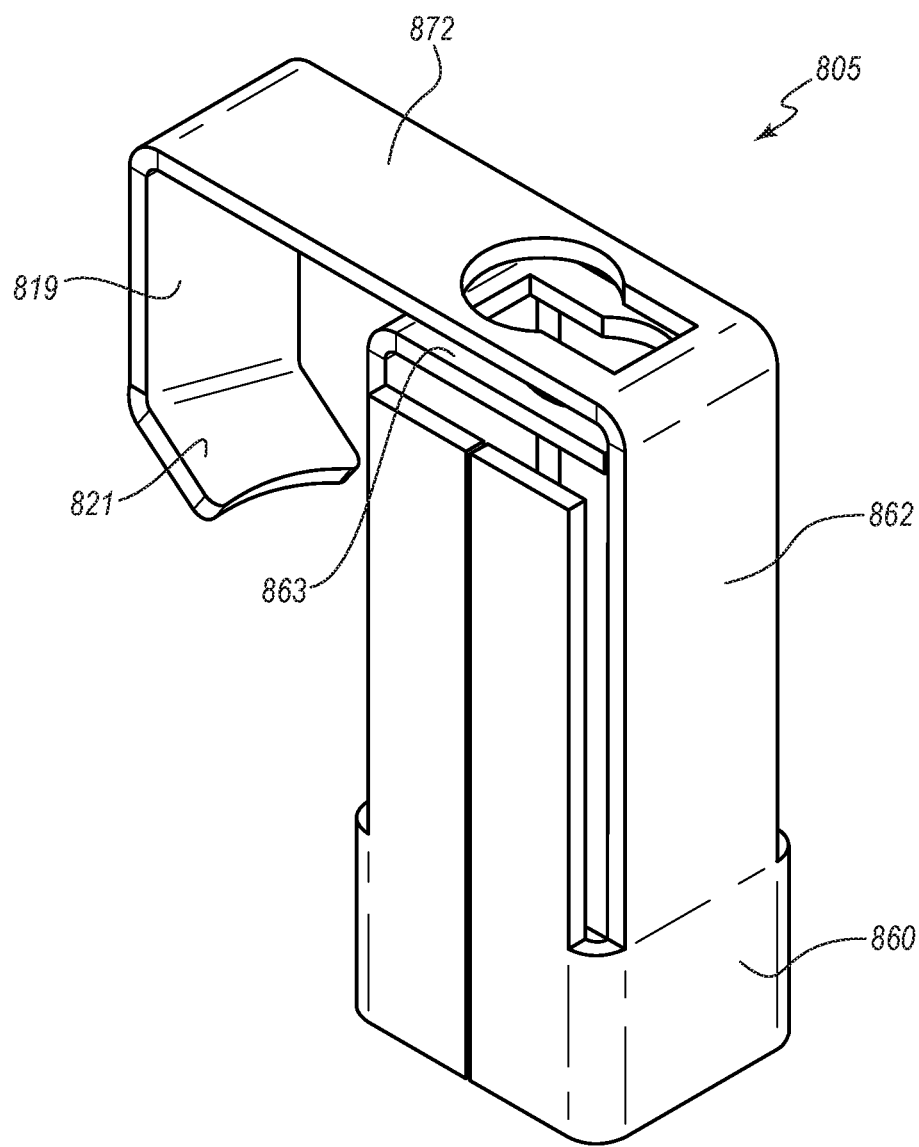
FIG. 33 is a perspective view of another embodiment of a shield.

FIG. 33 is a perspective view of another embodiment of a shield 805 that resembles the shields 105, 305, 405, 505 in many respects. The shield 805 is formed of a unitary piece of material (e.g., a single sheet of metal) and includes a collar 860 and a pair of opposing arms 862, 863. The arm 862 extends proximally from collar 860, is bent at approximately 90 degrees to define a lateral extension 872, is again bent at approximately 90 degrees to include a distally directed branch 819, and includes a coupling protrusion 821 at an end of the branch 819.

Figure 34:
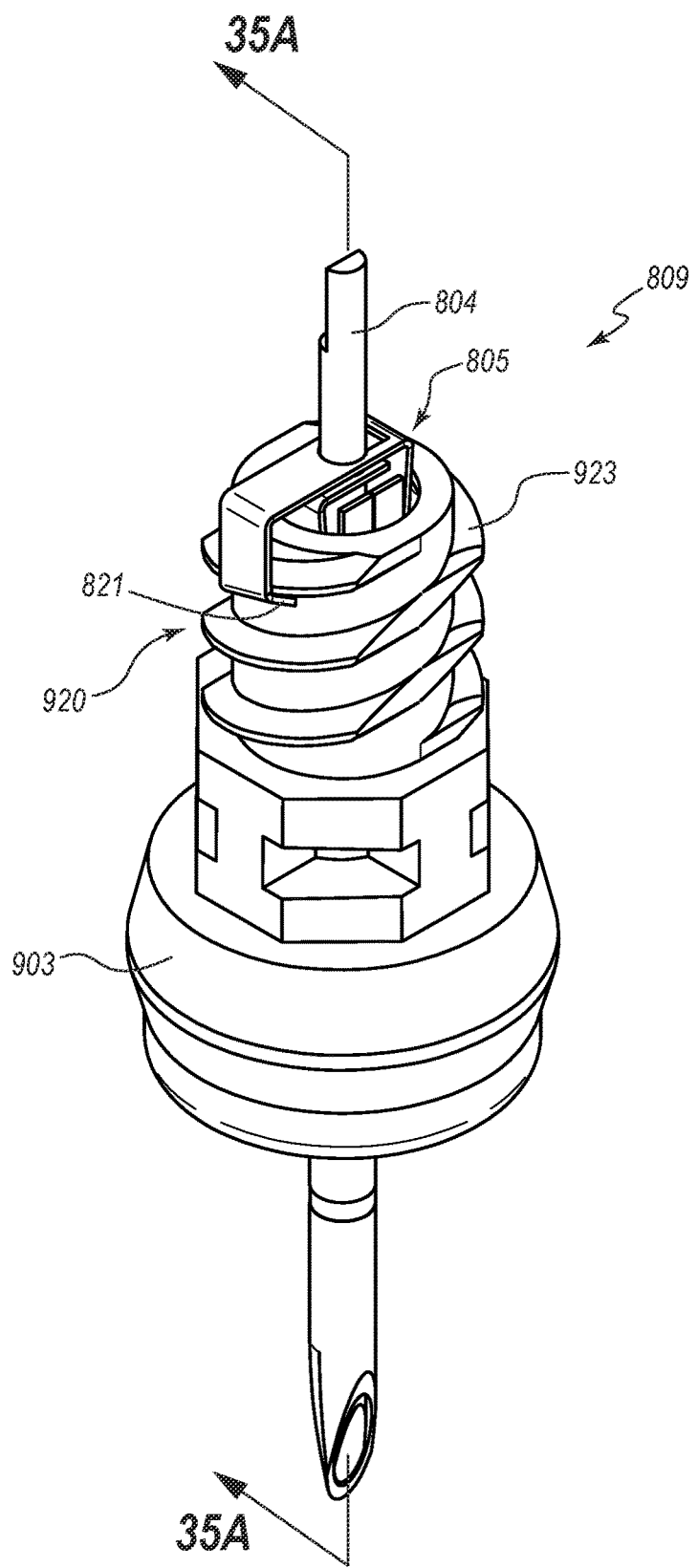
FIG. 34 is a perspective view of another embodiment of an access assembly with which the shield of FIG. 33 is compatible, the access assembly resembling that depicted in FIG. 15, but with an obturator hub portion thereof not being shown for purposes of clarity.

With reference to FIG. 34, the shield 805 can be incorporated into an access assembly 809, such as the access assemblies described above. The access assembly 809 can include a needle hub 903, which can include a connector 920 having threads 923 at an outer surface thereof. The access assembly 809 further includes an obturator 804. As further discussed below, the coupling protrusion 821 of the shield 805 can be configured to selectively engage and disengage the threads 923 to selectively couple and decouple the shield 805 to/from the needle hub 903.

Figure 35A:
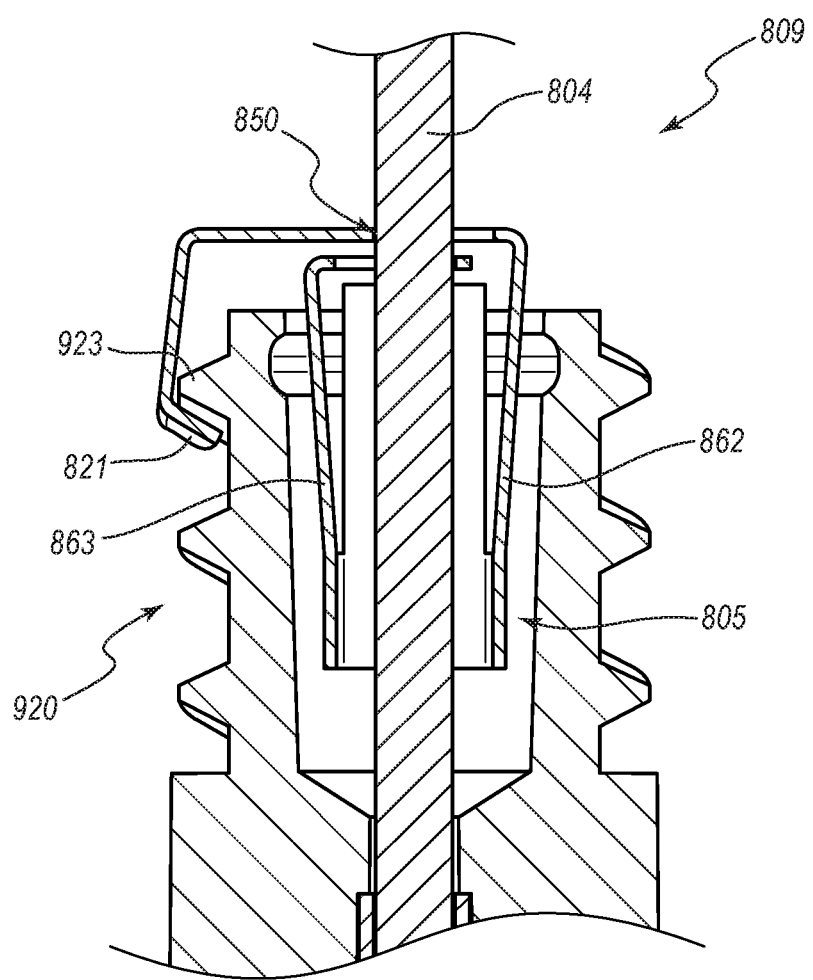
FIG. 35A is an enlarged cross-sectional view of the access assembly of FIG. 34, taken along the view line 35A-35A in FIG. 34, at a stage of an illustrative method in which the obturator assembly is being decoupled and withdrawn from the needle assembly while the shield is in an unlocked state relative to an obturator, and is in a coupling state relative to a needle hub.

FIG. 35A depicts a cross-sectional view of the access assembly 809 taken along the view line 35A-35A in FIG. 34. As shown, and as described above with respect to other embodiments, a relatively larger diameter proximal portion of the obturator 804 can maintain the arms 862, 863 in an outwardly deflected state against an internal bias of the arms. This outward deflection of the arms 862, 863 can urge the coupling protrusion 821 toward the connector 920 and into a coupled engagement with an underside or distal side of a thread 923. The underside of one or more of the threads 923 may be viewed as a recess into which the coupling protrusion 821 is received. In the stage depicted in both FIGS. 34 and 35A, which may be an initial stage of retraction of an obturator assembly from a needle assembly that includes the needle hub 903, the shield 805 is in an unlocked state relative to the obturator 804 and is in a coupled state relative to the needle hub 903. The shield 805 permits proximal movement of the obturator 804 relative thereto and, further, is substantially fixed relative to the needle hub 903.

Figure 35B:
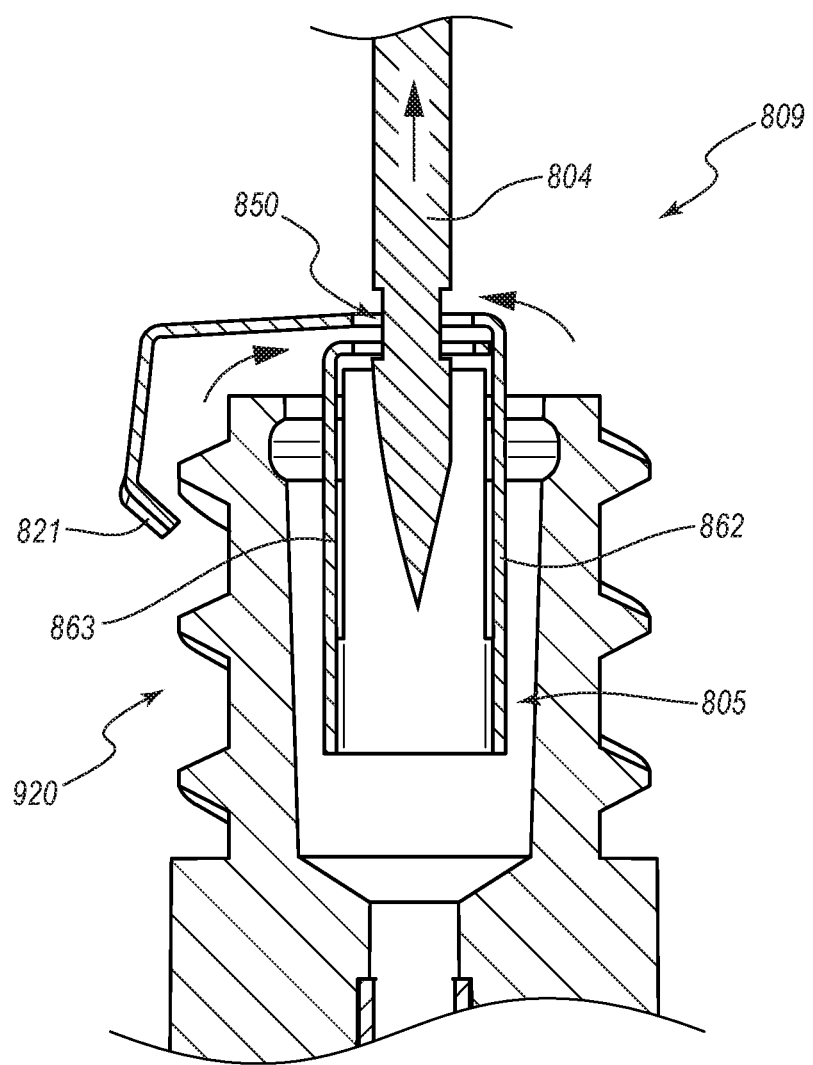
FIG. 35B is another enlarged cross-sectional view of the access assembly at a subsequent stage of the illustrative method in which the obturator assembly is being further withdrawn from the needle assembly and in which the shield transitions from the unlocked state to a locked state relative to the obturator and transitions from the coupling state to a decoupling state relative to the needle hub.

FIG. 35B depicts the shield 805 being transitioned from the unlocked/coupled state to a locked/uncoupled state. In particular, a recess 850 of the obturator 804 is positioned relative to the shield 805 such that the arms 862, 863 are permitted to naturally spring inwardly to a relaxed state. This inward movement of one portion of the arm 862 effects an outward movement of the coupling protrusion 821. Thus, the coupling protrusion 821 is moved away from, and is decoupled from, the needle hub 903. In the illustrated embodiment, the shield can transition to both the locked state relative to the obturator 804 and the decoupled state relative to the needle hub 903 substantially simultaneously. Note that substantially simultaneous locking, relative to the obturator, and decoupling, relative to the needle hub, can also be achieved with other embodiments described herein.

Figure 36:
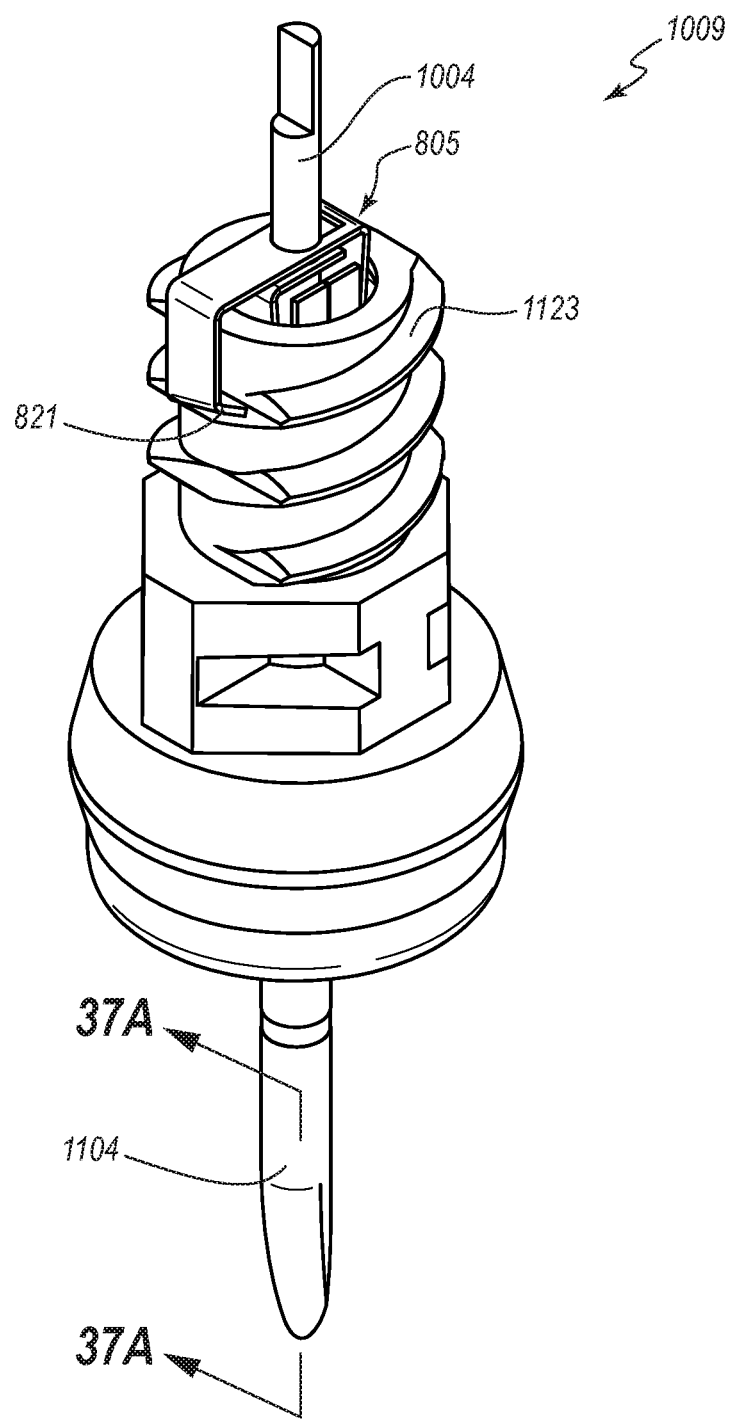
FIG. 36 is a perspective view of another embodiment of an access assembly with which the shield of FIG. 33 is compatible, the access assembly resembling that depicted in FIG. 15, but rotated 90 degrees relative to the shield and an obturator hub portion thereof not being shown for purposes of clarity.

FIG. 36 is a perspective view of another embodiment of an access assembly 1009 with which the shield 805 is compatible. The access assembly 1009 can resemble the access assembly 809, but can be rotated 90 degrees relative to the shield 805. In such an orientation, a different portion of one or more threads 1123 of a connector 1120 may be coupled with the coupling protrusion 821 of the shield 805 when the shield is in the unlocked/coupling configuration. In the illustrated embodiment, the coupling protrusion 821 is sized and shaped to grip the underside of two adjacent threads 923 positioned at opposing sides of a flattened region. The underside of the threads 923 may also be viewed as a recess into which the coupling protrusion 821 is received.

The access assembly 1009 can include an elongated medical device 1004 and a sheath 1104, as discussed further below. In the illustrated embodiment, the elongated medical device 1004 is an obturator and the sheath 1104 is a needle, such as in certain of the embodiments previously discussed.

Figure 37C:
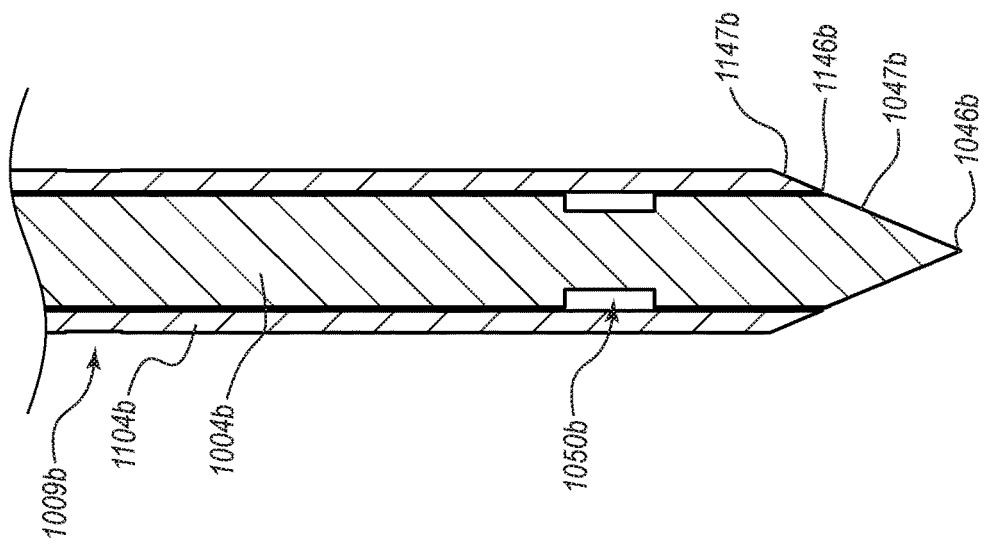
FIG. 37C is a cross-sectional view of a distal end of another embodiment of an access assembly that includes a trocar positioned within a needle, wherein a distal tip of the needle is adjacent to a cutting surface of the trocar.
Figure 37B:
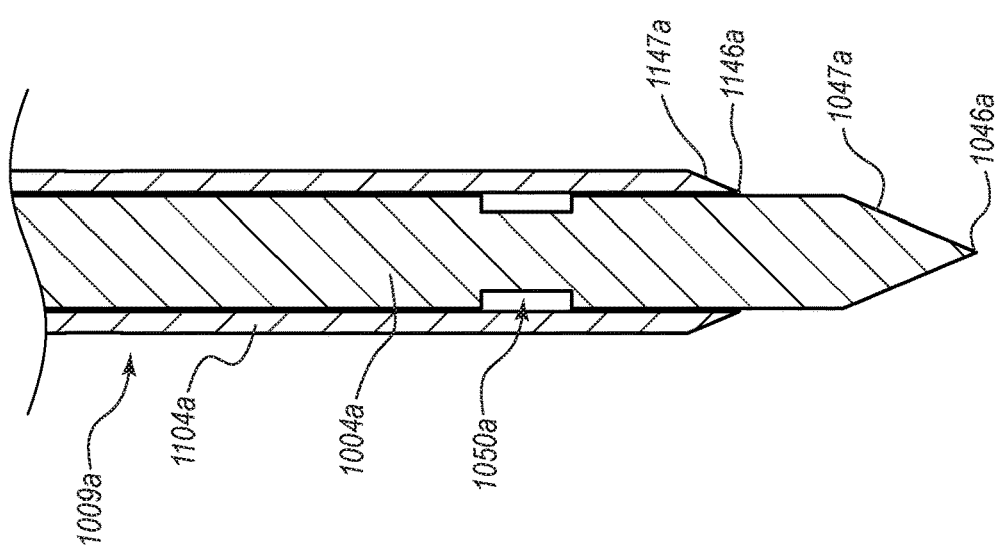
FIG. 37B is a cross-sectional view of a distal end of another embodiment of an access assembly that includes a trocar positioned within a needle, wherein a distal tip of the needle is proximally recessed relative to a cutting surface of the trocar.
Figure 37A:
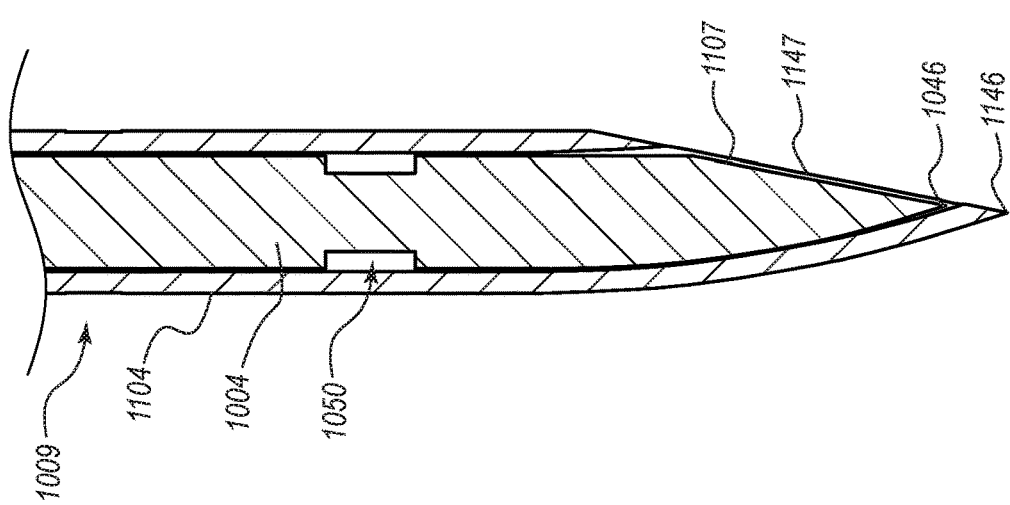
FIG. 37A is a cross-sectional view of a distal end of access assembly of FIG. 36 taken along the view line 37A-37A in FIG. 36 that shows a distal face of an obturator recessed relative to a distal face of a needle.

FIG. 37A depicts a cross-sectional view of a distal end of the access assembly 1009. In particular, a distal end of the obturator 1004 and a distal end of the needle 1104 are shown. As with other access assemblies disclosed herein, the access assembly 1009 may also be referred to as a penetration assembly or as a penetration system.

The obturator 1004 can include a recess 1050 that functions in the same manner as previously discussed. As with other embodiments discussed herein, a distal face 1047 of the obturator 1004 can be recessed relative to a distal face 1147 of the needle 1104. A distal tip 1046 of the obturator 1004 likewise can be recessed relative to the distal face 1147 of the needle 1104. In various embodiments, the distal tip 1146 and/or the distal face 1147 can contact and/or or cut bone during an insertion event.

FIG. 37B is a cross-sectional view of a distal end of another embodiment of a penetration assembly or access assembly 1009a. In particular, a distal end of an elongated medical instrument 1004a and a distal end of a sheath 1104a are shown. In the illustrated embodiment, the elongated medical instrument 1004a is a trocar having a distal tip 1046a and one or more distal faces 1047a. The distal tip 1046a, one or more of the distal faces 1047a, and/or one or more edges positioned between the adjacent distal faces 1047a can be configured to cut bone during an insertion event. In the illustrated embodiment, the sheath 1104a is a cannula having a distal tip 1146a and one or more distal faces 1147a. In the illustrated embodiment, the distal tip 1146a of the cannula 1104a is proximally spaced or recessed from the distal face or faces 1047a of the trocar 1004a. Stated otherwise, the cannula 1104a can define a lumen through which the trocar 1004a extends, and the trocar 1004a can extend distally past a distal end of the lumen. In some embodiments, the one or more distal faces 1147a of the cannula 1104a may be configured to cut bone during an insertion event.

FIG. 37C is a cross-sectional view of a distal end of another embodiment of an access assembly 1009b. In particular, a distal end of an elongated medical instrument 1004b and a distal end of a sheath 1104b are shown. In the illustrated embodiment, the elongated medical instrument 1004b is a trocar having a distal tip 1046b and one or more distal faces 1047b. The distal tip 1046b, one or more of the distal faces 1047b, and/or one or more edges positioned between the adjacent distal faces 1047b can be configured to cut bone during an insertion event. In the illustrated embodiment, the sheath 1104b is a cannula having a distal tip 1146b and one or more distal faces 1147b. In the illustrated embodiment, the distal tip 1146b of the cannula 1104b is adjacent to or substantially flush with a proximal end of the one or more distal faces 1047b of the trocar 1004b. In some embodiments, the one or more distal faces 1147b of the cannula 1104b may be configured to cut bone during an insertion event.

Figure 38:
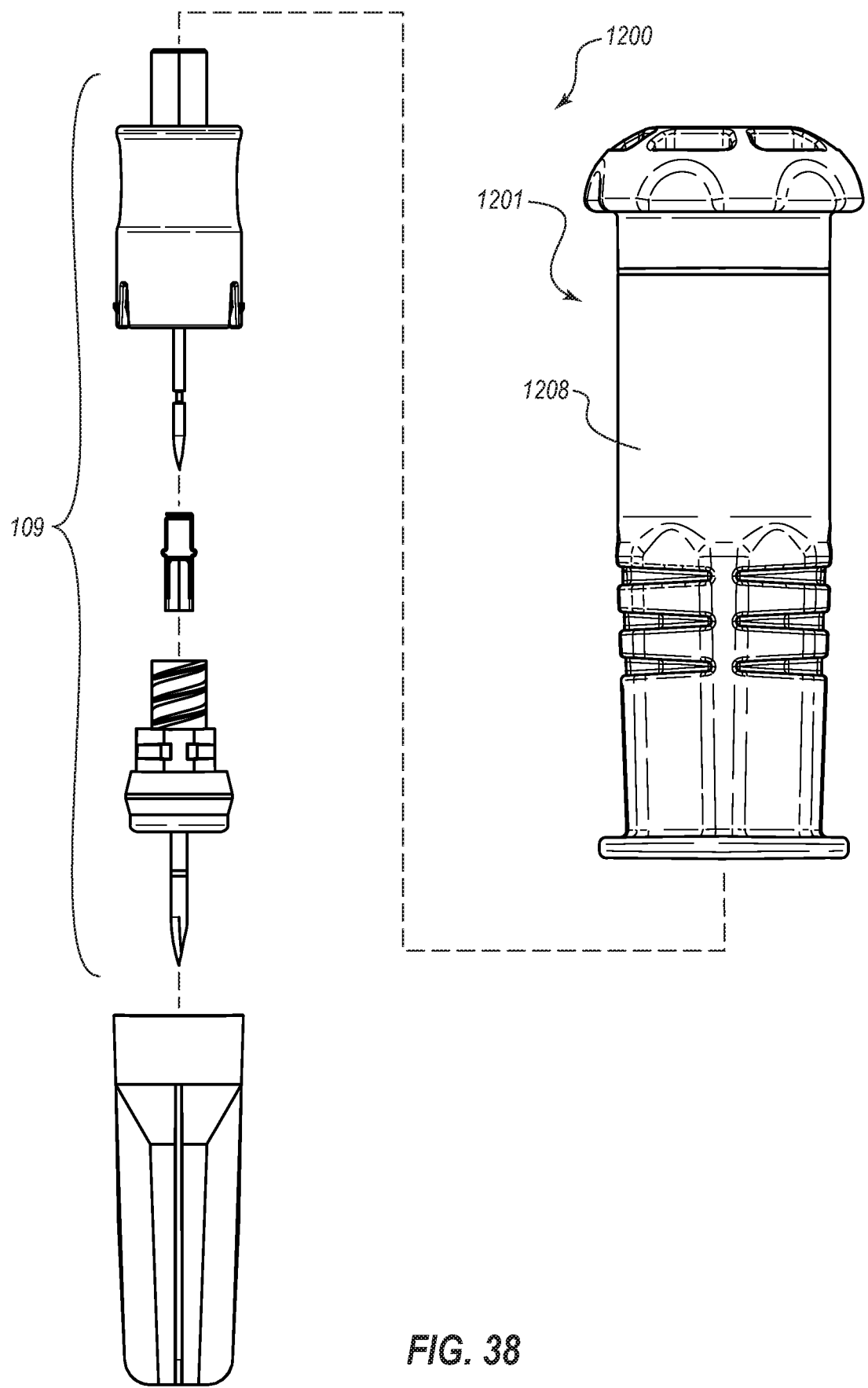
FIG. 38 is an exploded elevation view of another embodiment of an intraosseous access system that includes a manual driver.

FIG. 38 is an exploded elevation view of another embodiment of an intraosseous access system 1200 that includes any suitable access assembly, such as, for example, the access assembly 109 described above. The system 1200 further includes a driver 1201 for coupling with the access assembly 109 to drive the access assembly 109 into a bone of patient. In the illustrated embodiment, the driver 1201 is a manual driver 1208 that is configured to be manipulated by one or more hands of a practitioner.

Figure 39:
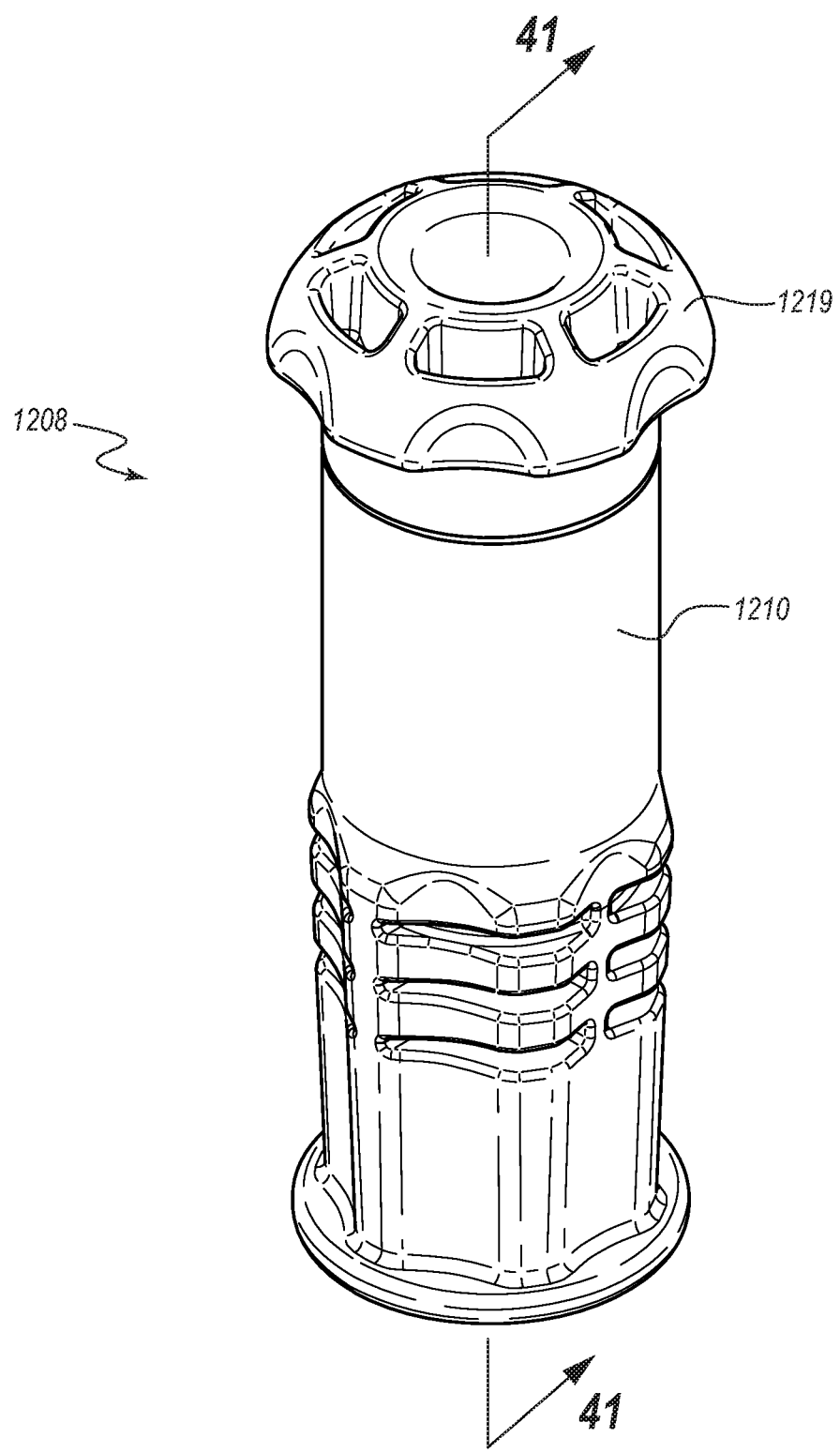
FIG. 39 is a perspective view of the manual driver.
Figure 40:
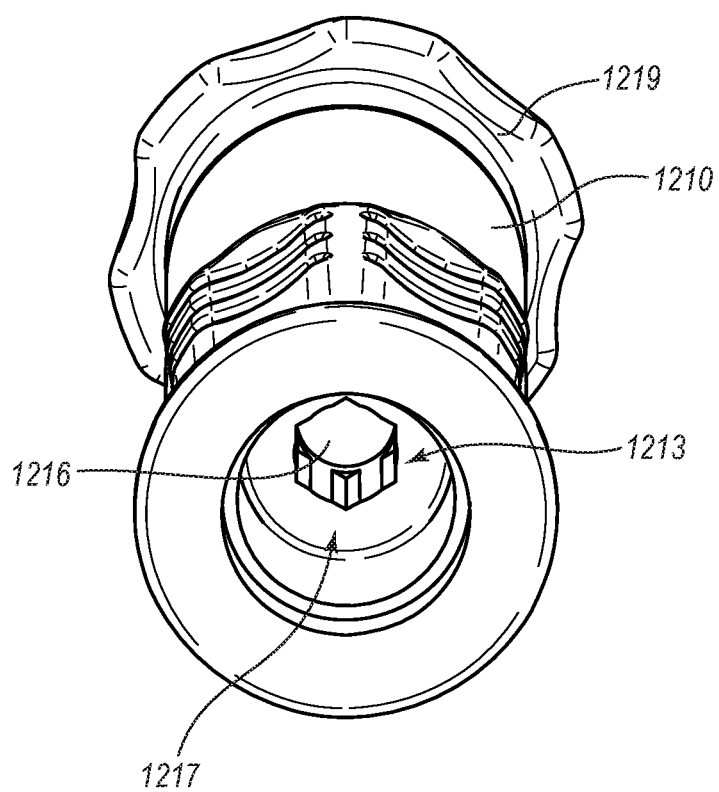
FIG. 40 is another perspective view of the manual driver.
Figure 41:
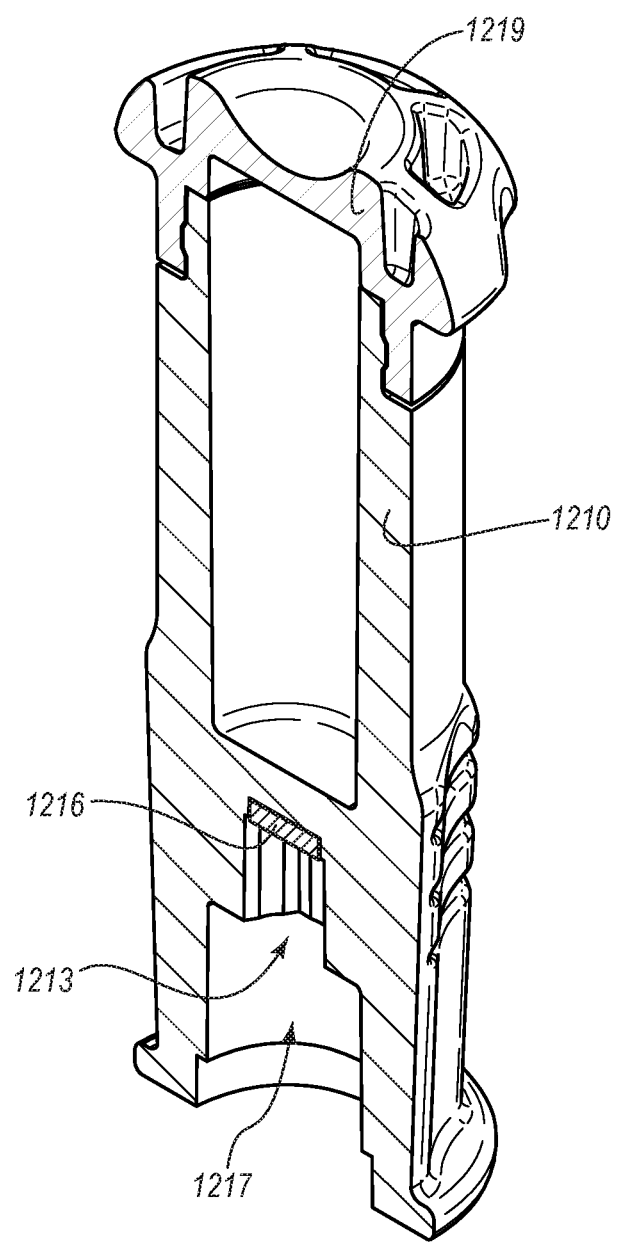
FIG. 41 is a cross-sectional view of the manual driver taken along the view line 41-41 in FIG. 39.

With reference to FIGS. 39-41, the manual driver 1208 can include a handle 1210 and a cap 1219. In the illustrated embodiment, the handle 1210 and the cap 1219 are rotatable relative to each other about a longitudinal axis of the manual driver 1208. Such an arrangement may, in some instances, facilitate an insertion procedure. For example, as previously discussed, in some instances a distal end of a needle may be configured to cut bone when rotated in either direction about the longitudinal axis. In some instances, a practitioner can press downwardly against the cap 1219 and can rotate the handle 1210 back and forth relative to the cap 1219 to insert the needle into the bone. In some instances, the practitioner may press the cap 1219 and rotate the handle 1210 with a single hand. In other instances, the practitioner may press the cap 1219 and rotate the handle with two different hands. In other embodiments, the handle 1210 and the cap 1219 may be fixedly secured to each other. For example, in some embodiments, the handle 1210 and the cap 1219 may be formed of a unitary piece of material (e.g., molded plastic).

With reference to FIGS. 40 and 41, the handle 1210 can define a socket 1213, such as the socket 113 described above, for receiving the shaft 123 of the coupling hub 103 (see FIG. 3). In some embodiments, a magnetic member 1216 (e.g., a magnet or a magnetic metal) can be positioned within the socket 113 to strongly couple with the magnetic member 124 (see FIG. 3). The handle 1210 can further define a cavity 1217 into which the body 120 of the coupling hub 103 can be received (see FIG. 3).

Figure 42:
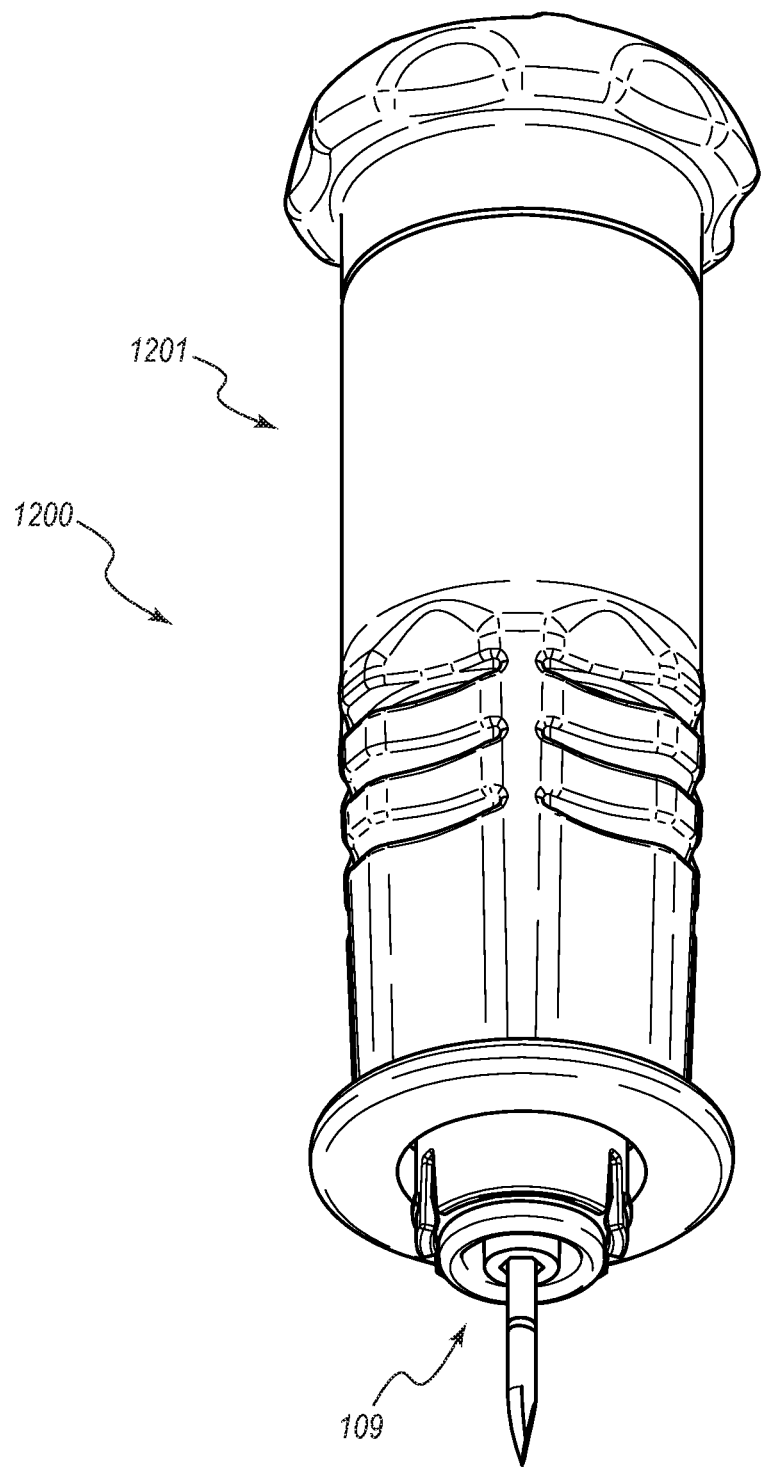
FIG. 42 is a perspective view of the intraosseous access system of FIG. 38 depicted in an assembled state.

FIG. 42 is a perspective view of the intraosseous access system 1200 depicted in an assembled state. In particular, the driver 1201 is coupled to the access assembly 109.

Figure 43:
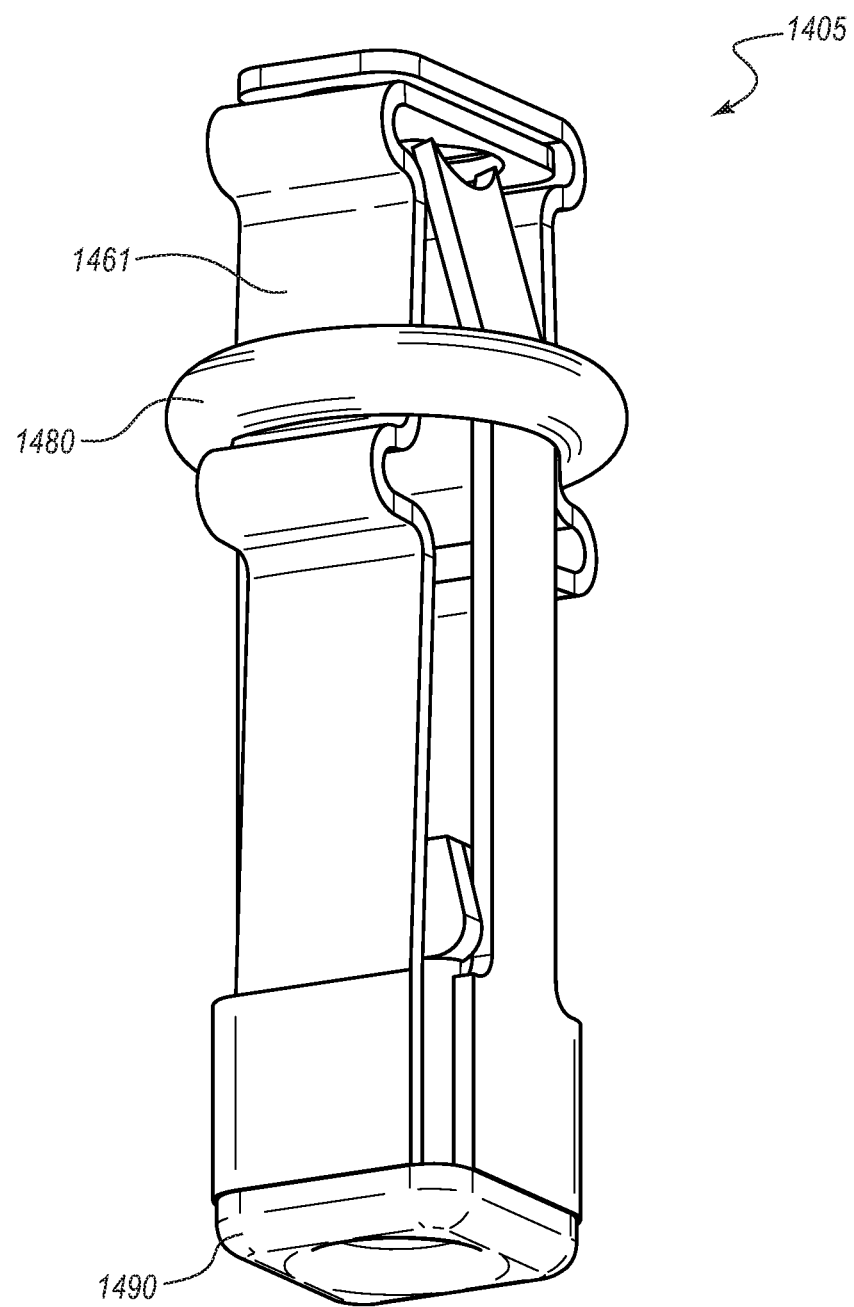
FIG. 43 is a perspective view of another embodiment of a shield that is compatible with, e.g., embodiments of intraosseous access systems disclosed herein, the shield comprising multiple separate components.

FIG. 43 depicts another embodiment of a shield 1405 similar to other shields disclosed herein, which can be suitable for use with many of the embodiments of systems disclosed herein. The shield 1405 includes a body 1461, a retainer 1480, and a guide 1490.

Figure 44:
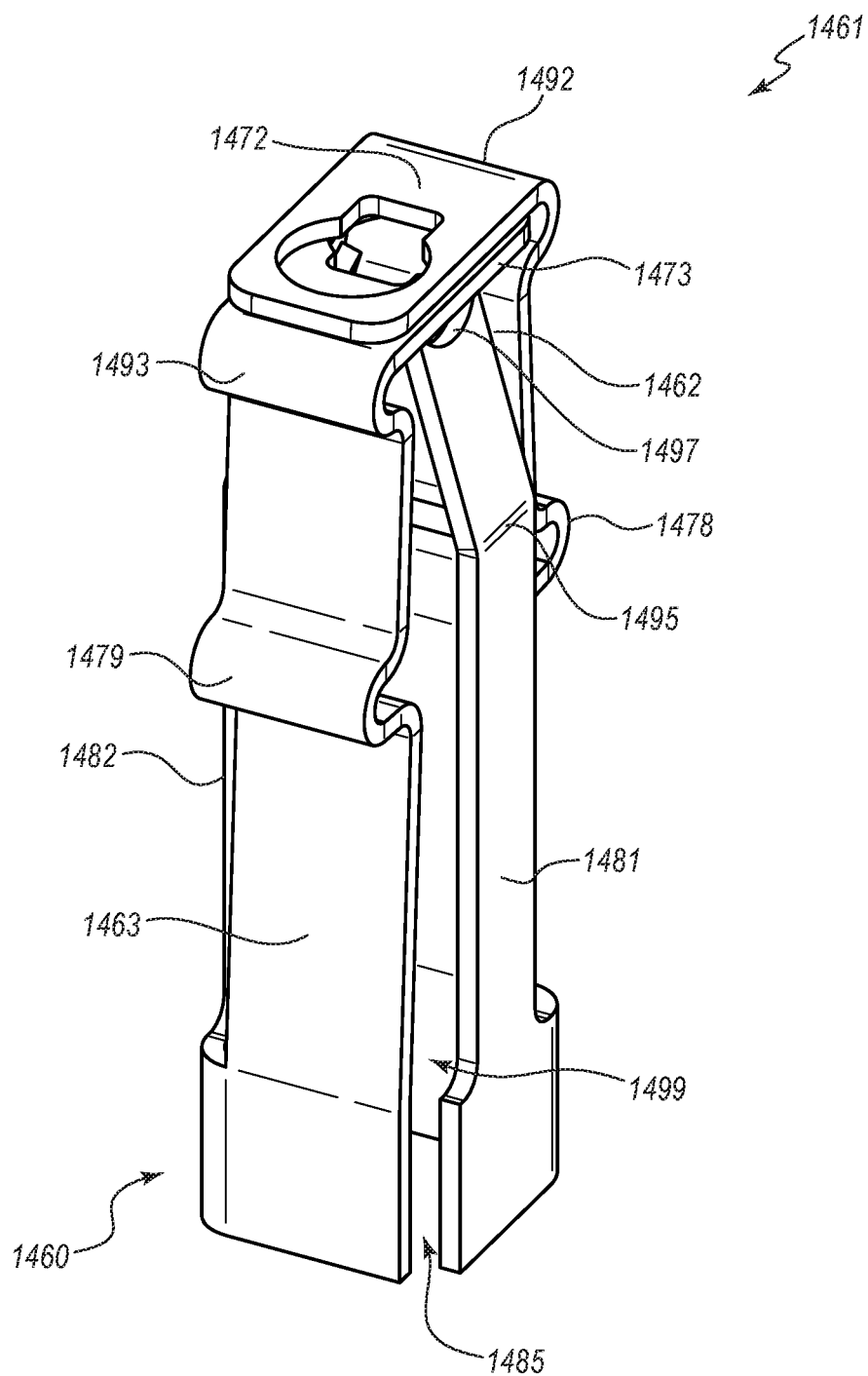
FIG. 44 is a perspective view of a body portion of the shield of FIG. 43.

With reference to FIG. 44, the body 1461 can resemble other shields and shield bodies previously discussed. The body 1461 can be formed from a unitary piece of material, such as stainless steel, etc. The body 1461 can be folded into the form shown, and may have a seam 1485 at a corner of a collar 1460. The body 1461 includes a pair of arms 1462, 1463 at opposing sides thereof. The body 1461 further includes a pair of panels 1481, 1482 at separate opposing sides thereof. In particular, the panels 1481, 1482 are offset from the arms 1462, 1463 by 90 degrees about a longitudinal axis of the body 1461. The panels 1481, 1482 may also be referred to as supports, struts, beams, etc.

Each arm 1462, 1463 can include an outward protrusion 1478, 1479, which can resemble and function in the same manner as the protrusions 178, 179 previously discussed. Moreover, the protrusions 178, 179 can function as distal stops that can prevent distal movement of the retainer 1480, e.g., after the shield 1405 has been decoupled from a hub. The protrusions 1478, 1479 may be referred to as distal protrusions 1478, 1479 or as distal stops.

Each arm 1462 can further include protrusions 1492, 1493, which may be shaped similarly to the protrusions 1478, 1479. The upper ends of the protrusions 1492, 1493 can lead directly into lateral extensions 1472, 1473. In some instances, the protrusions 1492, 1493 can provide for a stronger bend, which can lead to firmer lateral extension 1472, 1473 that are less resistant to being bent out of shape while retaining the shield 1405 in a locked relationship to an obturator. In other or further instances, the protrusions 1492, 1493 can facilitate manufacture of the body 1461. The protrusions 1492, 1493 can function as proximal stops that can prevent proximal movement of the retainer 1480 off of the body 1461, e.g., after the shield 1405 has been decoupled from a hub. The protrusions 1492, 1493 may be referred to as proximal protrusions 1492, 1493 or as proximal stops.

The panels 1481, 1482 can be configured to provide support (e.g., supplemental support), to prop up, to strengthen, or otherwise assist the lateral extensions 1472, 1473. The panels 1481, 1482 can have proximal ends that are positioned adjacent to, beneath, or in contact with a distal surface of the lateral extension 1473 (see also FIG. 43). In the event of a large distally directed force on the upper lateral extension 1472, the lateral extension 1472 may move downward into contact with the lateral extension 1473, which may in turn move downward into contact with the proximal ends of the panels 1481, 1482. The panels 1481, 1482 can prevent any further distal movement or displacement of the lateral extensions 1472, 1473, which can prevent deformations of the lateral extensions 1472, 1473 the might otherwise decouple the lateral extensions 1472, 1473 from an obturator, such as by reorienting openings defined by the lateral extensions 1472, 1473 to a position where the obturator can pass through the openings. For example, such deformations or reorientations could decouple the lateral extensions 1472, 1473 from a recess of an obturator.

As an illustrative example, in some instances, the lateral extensions 1472, 1473 may be securely locked within an obturator recess that includes a proximal sidewall. In the event of application of inadvertent pressure to the distal end of the shield 1405 (e.g., a practitioner's inadvertent bumping against the distal end of an obturator assembly, such as might otherwise result in a sharps injury in the absence of the shield 1405), reactive forces from the proximal sidewall of the obturator recess can act on the upper lateral extension 1472, tending to push it distally. As previously discussed, the panels 1481, 1482 can assist in preventing such inadvertent force from decoupling the shield 1405 from the obturator in a manner that might expose the distal tip of the obturator.

In the illustrated embodiment, the support panels 1481, 1482 are angled inward, such that their proximal ends are positioned beneath the lateral extension 1473. In particular, each support panel 1481, 1482 includes a bend 1495 that directs the support structure inward. This bend provides further strength to the system. The bends 1495 redirect forces inward, thus pushing the upper ends of the support panels 1481, 1482 against the obturator and tending to ensure that the upper ends remain beneath the lateral extensions 1473, 1472. In some embodiments, the upper ends of the support panels 1481, 1482 define a curve 1497 to achieve better contact with a rounded obturator.

With reference to FIGS. 43-45, in some embodiments, the retainer 1480 provides further support to the arms 1461, 1462 and the panels 1481, 1482. The retainer 1480 can inhibit or prevent the arms 1461, 1462 and the panels 1481, 1482 from being displaced outwardly. As shown in FIG. 43, the retainer 1480 can encompass or encircle the arms 1461, 1462 and the panels 1481, 1482.

In some embodiments, the retainer 1480 is resiliently flexible. For example, in some embodiments, the retainer 1480 comprises an elastomeric ring of any suitable variety (e.g., an O-ring). In some instances, the retainer 1480 can provide some or all of an inwardly directed bias that tends to urge the arms 1461, 1462 inwardly toward an elongated instrument (e.g., obturator) that passes through the shield 1405. For example, in some embodiments, the arms 1461, 1462 may have an intrinsic bias that urges the arms 1461, 1462 inward when the arms have been deflected outward. In certain of such embodiments, the elastomeric ring may be stretched or deformed outwardly under such circumstances, which may give rise to an internal bias with in the ring that also tends to urge the arms 1461, 1462 inwardly. In other embodiments, the arms 1461, 1462 may have no inherent or internal bias when they are deflected outwardly, and the retainer 1480 may supply an entirety of an inwardly directed bias (e.g., a continuous bias) toward a locked state when the arms 1461, 1462 are deflected outwardly into an unlocked state.

With reference to FIGS. 43, 44, 46A, and 46B, in certain embodiments, the body 1461 can define a gap 1499 between adjacent longitudinally extending elements, such as between the arm 1463 and the panel 1481. In some embodiments, the guide 1490 defines a catch 1495 that extends through the gap 1499 to secure or assist in securing the guide 1490 to the body 1461. In the illustrated embodiment, the catch 1495 includes a sloped proximal face and a jutting distal face. The sloped proximal face can ease insertion of the guide 1490 into the body, such as may gradually expand the collar 1460 as the guide 1490 is pressed into the body 1461. Once the catch 1495 has passed the collar 1460, the collar 1460 can spring back into place, and the jutting distal face can interfere with a proximal end of the collar to prevent the catch 1495 from being pulled out of the body 1461. Other connection arrangements between the catch 1490 and the body 1461 are contemplated.

The guide 1490 can be configured to inhibit or prevent lateral movement of the shield 1405, which can aid in preventing inadvertent decoupling of the shield 1405 from an elongated instrument (e.g., obturator). Moreover, in other or further instances, the guide 1490 can prevent a distal tip of the body 1461 from catching on the sidewalls of a recess (e.g., a distal face of a groove) or otherwise moving into the recess as the elongated instrument is moved proximally through the shield 1405.

In the illustrated embodiment, the guide 1490 includes a body 1491 that is insertable through the collar 1460, as previously described. A cap 1492 can be positioned at a distal end of the body 1491. The cap 1492 can extend laterally outwardly from the body 1491, and may cover or substantially cover a distal top of the body 1491 (see FIG. 43).

The guide 1490 can further define a channel 1493 that extends through the cap 1492 and the body 1493. The channel 1492 can include a flared opening or mouth 1493 that narrows in the proximal direction. The mouth 1493 can smoothly pass over a recess to prevent catching between the shield 1405 and the recess (e.g., groove). In some embodiments, a length of the guide 1490 is longer than a length of the recess, which may advantageously facilitate passage of the guide 1490 over the recess. In other embodiments, the guide 1490 may be the same length as or shorter than the recess.

The guide 1490 can be formed in any suitable manner. In some embodiments, the guide 1490 is micromachined. In other embodiments, the guide 1490 is molded. In some embodiments, the guide 1490 is adhered within the body 1461, whereas in other embodiments, the guide 1490 is secured within the body 1461 without adhesives.

Figure 47:
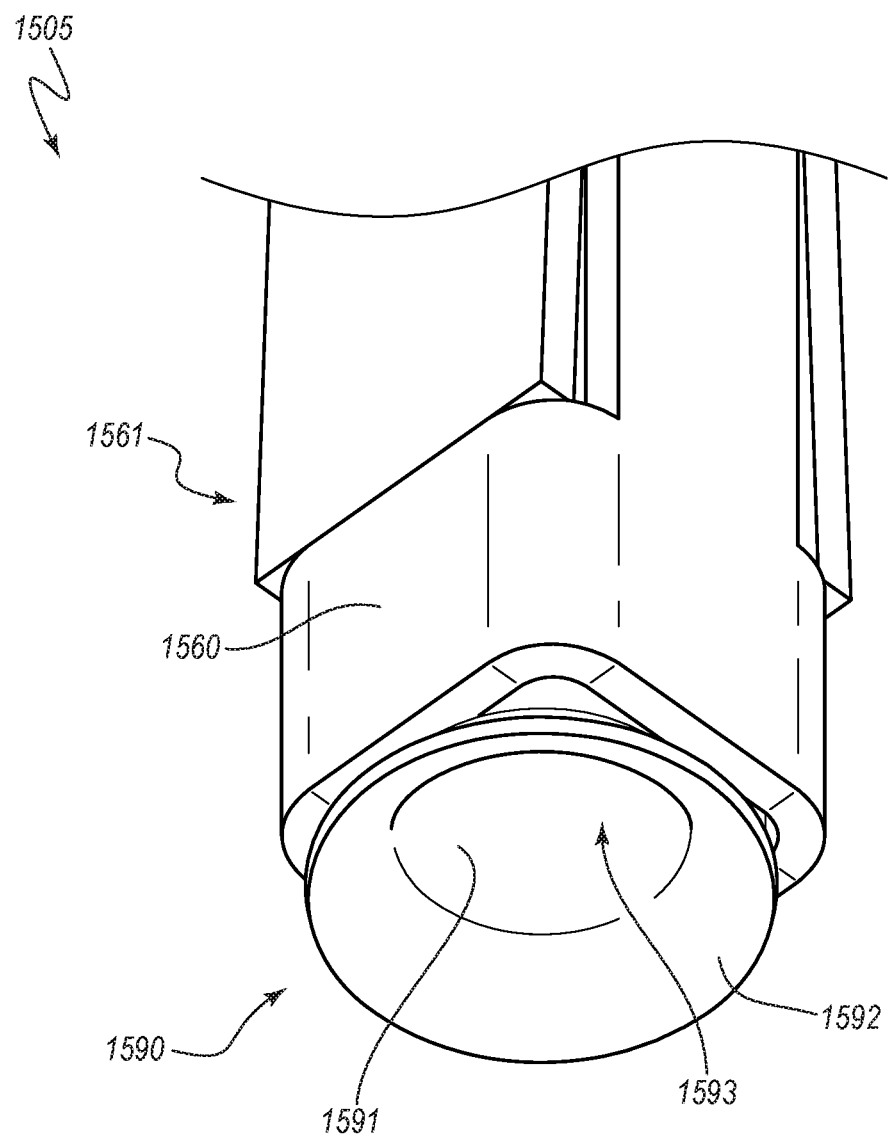
FIG. 47 is a perspective view of a distal portion of another embodiment of a shield that is compatible with, e.g., embodiments of intraosseous access systems disclosed herein.

FIG. 47 depicts another embodiment of a shield 1505 similar to other shields disclosed herein, which can be suitable for use with many of the embodiments of systems disclosed herein. The shield 1505 includes a body 1561 that includes a collar 1560 at a distal end thereof. The shield 1505 further includes a guide 1590 positioned within the collar 1560.

In the illustrated embodiment, the guide 1590 includes a body 1591 that defines a tapered mouth 1592 and a channel 1593, such as like-named elements above. In the illustrated embodiment, the guide 1590 is formed of a tube having a flared end. A proximal end of the tube is inserted into the collar 1560 and may, in some instances, be retained therein via a friction fit.

As previously discussed, many of the embodiments disclosed herein are particularly well-suited for intraosseous access applications, such as for accessing the vasculature of a patient and/or for removing material from bones, and are discussed in this context for the sake of simplicity. This focus on intraosseous access systems should not, however, be construed as limiting. Embodiments disclosed herein may be used in a variety of other contexts. In particular, numerous procedures involve needles, trocars, stylets, obturators, or any of a host of other elongated instruments that are inserted into a patient and that are removed from the patient through a hub. In further procedures, the hub may be coupled with a cannula or other suitable instrument that is also inserted into the body of the patient. At some point in the procedure, the elongated instrument can extend through this additional instrument. For example, the elongated body and the additional instrument may be inserted into the body in unison, and the elongated body thereafter removed. A variety of other methodologies and systems are also known.

The present disclosure contemplates any suitable application of the technologies described here. Accordingly, additional illustrative, nonlimiting examples of applications of the present disclosure include a wide variety of biopsy needles, Chiba needles, aspiration needles, catheter placement needles, epidural needles, various trocar applications, etc.

The term "patient" is used broadly herein and is not intended to be limiting. A patient can be, for example, any individual who undergoes any of the methods or treatments discussed herein, whether in a hospital, first responder, or other setting. The term "patient" includes humans, mammals more generally, or any other animal possessing anatomy compatible with embodiments described herein. Accordingly, in some instances, various systems and procedures described herein are suitable for use with human bodies, mammalian bodies more generally, etc.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A system comprising:
   a cannula assembly configured to be coupled with a rotational driver, the cannula assembly comprising:
      a cannula hub; and
      a cannula attached to the cannula hub, the cannula defining a lumen and a central longitudinal axis, the cannula being configured to be introduced into a bone via rotation about the central longitudinal axis;
   an elongated instrument comprising a distal tip and a recess that is proximally spaced from the distal tip, the elongated instrument being positioned within the lumen of the cannula; and
   a shield coupled with each of the cannula hub and the elongated instrument while in an unlocked state, the shield comprising a resilient arm that is maintained by the elongated instrument in a deflected orientation in which the resilient arm engages the cannula hub when the shield is in the unlocked state, the shield being configured to:
      remain coupled with the cannula hub and the elongated instrument in the unlocked state as the cannula assembly is rotated by the rotational driver and the cannula is introduced into the bone;
      while in the unlocked state, remain coupled with the cannula hub while permitting the elongated instrument to translate proximally relative to the shield as the elongated instrument is retracted from the lumen of the cannula; and automatically transition from the unlocked state to a locked state when the elongated instrument is further retracted from the lumen of the cannula to a position at which the resilient arm enters the recess of the elongated instrument while simultaneously disengaging from the cannula hub, wherein the shield attaches to a distal end of the elongated instrument to restrict access to the distal tip of the elongated instrument when in the locked state, wherein the shield further comprises a collar at a distal end of the shield that encompasses the elongated instrument, wherein a distal end of the resilient arm is connected to the collar, and wherein a proximal end of the resilient arm is laterally movable relative to the elongated instrument.

2. The system of claim 1, further comprising a coupling hub attached to the elongated instrument, wherein the coupling hub is configured to couple with the cannula hub in a manner that causes the coupling hub and the elongated instrument to rotate in unison with the cannula hub.

3. The system of claim 2, wherein the coupling hub comprises a coupling interface that is configured to be coupled with the rotational driver.

4. The system of claim 3, wherein the coupling hub further comprises an additional coupling interface that couples the cannula hub with the coupling hub in a fixed angular orientation.

5. The system of claim 2, wherein the cannula comprises a needle and the elongated instrument comprises an obturator configured to inhibit or prevent material from entering the needle.

6. The system of claim 1, further comprising the rotational driver.

7. The system of claim 6, wherein the rotational driver comprises a manual driver.

8. The system of claim 6, wherein the rotational driver comprises an automated driver.

9. The system of claim 8, wherein the automated driver is configured to rotate the cannula assembly at speeds greater than can be achieved by manual rotation of the cannula assembly.

10. The system of claim 1, wherein when the shield is in the locked state, at least a portion of a contact region of the resilient arm is positioned within the recess of the elongated instrument and a distal tip of the shield is positioned distally relative to the distal tip of the elongated instrument to restrict access to the distal tip of the elongated instrument.

11. The system of claim 10, wherein the resilient arm is flexed when the shield is in the unlocked state, and wherein the resilient arm automatically relaxes to a less flexed condition to transition the shield to the locked state.

12. The system of claim 1, wherein the resilient arm comprises an intrinsic bias when in the unlocked state that tends to urge the resilient arm toward the locked state.

13. The system of claim 1, wherein a proximal portion of the elongated instrument that is adjacent to the recess defines a first diameter, and wherein the recess comprises a grooved region that defines a second diameter that is smaller than the first diameter.

14. The system of claim 13, wherein the resilient arm defines an opening that comprises:

a passageway portion that defines a third diameter that is larger than the first diameter to permit passage of the proximal portion of the elongated instrument therethrough; and a receptacle portion into which the grooved region is received, an entryway to the receptacle portion defining a fourth diameter that is smaller than the first diameter and larger than the second diameter.

15. The system of claim 1, wherein the resilient arm comprises a lateral extension that fully encompasses the elongated instrument.

16. The system of claim 15, further comprising an additional arm that covers a portion of the lateral extension when the shield is in the locked state, the additional arm maintaining the shield in the locked state by inhibiting application of force to the covered portion of the lateral extension in a direction that would move the resilient arm out of the recess.

17. The system of claim 1, wherein the collar defines an opening through which the elongated instrument extends when the shield is in the unlocked state, and wherein the opening is configured to remain open when the distal tip of the elongated instrument is drawn into the shield and the shield is transitioned to the locked state.

18. A system comprising:

a hub that defines a first contact surface;

an elongated instrument extending through the hub, the elongated instrument comprising a distal tip, a proximal portion that defines a second contact surface, and a recess that is laterally recessed relative to the second contact surface; and a shield that comprises a distal end positioned in the hub and an arm that extends proximally from the distal end, the arm comprising a laterally movable extension that is positioned outside of and proximal to a proximal end of the hub, the extension defining a first contact region and the arm defining a second contact region, the arm being in a deflected state and, while in the deflected state, being subjected to a continuous bias to move to a contracted state, the shield being positioned over the elongated instrument such that the first contact region of the extension interfaces with the second contact surface of the elongated instrument to maintain the arm in the deflected state, the second contact region of the arm interfacing with the first contact surface of the hub to couple the shield with the hub while the arm is in the deflected state, wherein proximal movement of the elongated instrument relative to the shield repositions the recess of the elongated instrument such that the first contact region of the extension discontinues interfacing with the second contact surface of the elongated instrument to permit the arm to automatically move from the deflected state to the contracted state under the influence of the bias, and wherein, when the arm is moved to the contracted state, a portion of the extension moves laterally to enter the recess of the elongated instrument to secure the shield in a position that covers the distal tip of the elongated instrument and the second contact region of the arm discontinues interfacing with the first contact surface of the hub to decouple the shield from the hub.

* * * * *